US012569438B2

(12) United States Patent
Dahlman et al.

(10) Patent No.: US 12,569,438 B2
(45) Date of Patent: Mar. 10, 2026

(54) NANOMATERIALS CONTAINING CONSTRAINED LIPIDS AND USES THEREOF

(71) Applicant: GEORGIA TECH RESEARCH CORPORATION, Atlanta, GA (US)

(72) Inventors: James Everett Dahlman, Atlanta, GA (US); Cory Dane Sago, Atlanta, GA (US); Zubao Gan, Avondale, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 865 days.

(21) Appl. No.: 17/630,861

(22) PCT Filed: Jul. 24, 2020

(86) PCT No.: PCT/US2020/043512
§ 371 (c)(1),
(2) Date: Jan. 27, 2022

(87) PCT Pub. No.: WO2021/021634
PCT Pub. Date: Feb. 4, 2021

(65) Prior Publication Data

US 2022/0273566 A1 Sep. 1, 2022

Related U.S. Application Data

(60) Provisional application No. 62/879,731, filed on Jul. 29, 2019.

(51) Int. Cl.

| | |
|---|---|
| ***A61K 9/1271*** | (2025.01) |
| ***A61K 9/51*** | (2006.01) |
| ***A61K 31/713*** | (2006.01) |
| ***A61K 47/14*** | (2017.01) |
| ***A61K 47/18*** | (2017.01) |
| ***A61K 48/00*** | (2006.01) |
| ***A61P 37/02*** | (2006.01) |
| ***B82Y 5/00*** | (2011.01) |

(52) U.S. Cl.
CPC .......... *A61K 9/1271* (2013.01); *A61K 9/5123* (2013.01); *A61K 9/5146* (2013.01); *A61K 31/713* (2013.01); *A61K 47/14* (2013.01); *A61K 47/18* (2013.01); *A61K 48/0033* (2013.01); *A61P 37/02* (2018.01); *B82Y 5/00* (2013.01)

(58) Field of Classification Search
CPC .. A61K 9/1271; A61K 9/5123; A61K 9/5146; A61K 31/713; A61K 47/14; A61K 47/18; A61K 48/0033; A61P 37/02; B82Y 5/00
See application file for complete search history.

(56) References Cited

U.S. PATENT DOCUMENTS

| | | | |
|---|---|---|---|
| 3,686,238 | A | 8/1972 | Zaffaroni et al. |
| 8,058,069 | B2 | 11/2011 | Yaworski et al. |
| 9,364,435 | B2 | 6/2016 | Yaworski et al. |
| 9,840,699 | B2 | 12/2017 | Liu et al. |
| 10,113,163 | B2 | 10/2018 | Liu et al. |
| 10,124,065 | B2 | 11/2018 | Baryza et al. |
| 10,167,457 | B2 | 1/2019 | Liu et al. |
| 2003/0083272 | A1 | 5/2003 | Wiederholt et al. |
| 2016/0311759 | A1 | 10/2016 | Brito et al. |
| 2017/0210698 | A1 | 7/2017 | Benenato et al. |
| 2018/0147166 | A1 | 5/2018 | Dong et al. |
| 2018/0290965 | A1 | 10/2018 | Brito et al. |
| 2019/0002393 | A1 | 1/2019 | Beckwith et al. |
| 2019/0076462 | A1 | 3/2019 | Dong et al. |
| 2019/0358170 | A1 | 11/2019 | Brito et al. |
| 2021/0130805 | A1 | 5/2021 | Gaudelli et al. |
| 2021/0169804 | A1 | 6/2021 | Patwardham et al. |
| 2021/0230112 | A1 | 7/2021 | Hamilton et al. |
| 2022/0096381 | A1 | 3/2022 | Endo et al. |
| 2022/0249694 | A1 | 8/2022 | Shehata et al. |
| 2022/0273566 | A1 | 9/2022 | Dahlman et al. |

FOREIGN PATENT DOCUMENTS

| | | | |
|---|---|---|---|
| AU | 2020369940 | A1 | 5/2022 |
| CN | 108368028 | A | 8/2018 |
| CN | 110520409 | A | 11/2019 |
| EP | 1164125 | A1 | 12/2001 |
| EP | 3733211 | A1 | 11/2020 |

(Continued)

OTHER PUBLICATIONS

Google Search; Is adamantyl cycloalkyl? (Year: 2025).*
Google Search; Why is adamantyl group on an ionizable lipid? (Year: 2025).*
Kanasty et al.; Delivery materials for siRNA therapeutics; Nature Materials | vol. 12 | Nov. 2013 | www.nature.com/naturematerials (Year: 2013).*
SciFinder hits; ionizable lipid (Year: 2025).*
Adams et al., Jul. 5, 2018, Patisiran, an RNAi therapeutics, for hereditary transthyretin amyloidosis, N Engl J Med, 379(1):11-21.

(Continued)

*Primary Examiner* — Robert A Wax
*Assistant Examiner* — John W Lippert, III
(74) *Attorney, Agent, or Firm* — Karen A. LeCuyer; DeWitt LLP

(57) ABSTRACT

Compositions for delivering nucleic acids to cells or tissue microenvironments are provided. In one embodiment, the compositions are lipid nanoparticle compositions formulated to have reduced splenic and hepatic clearance. It has been discovered that the chemical composition of lipid nanoparticles significantly influences the natural trafficking of the lipid nanoparticles. More specifically, it has been discovered that conformationally constrained ionizable lipids can modify the tropism and clearance profile of lipid nanoparticles without the need of a targeting ligand. It has also been discovered that tropism of the disclosed lipid nanoparticles is size-independent.

26 Claims, 22 Drawing Sheets

Specification includes a Sequence Listing.

(56) References Cited

FOREIGN PATENT DOCUMENTS

| | | | | |
|---|---|---|---|---|
| EP | 3842538 | A1 | 6/2021 | |
| EP | 4069675 | A1 | 10/2022 | |
| GB | 968849 | | 9/1964 | |
| JP | 2005181734 | A | 7/2005 | |
| WO | WO 02/44321 | | 6/2002 | |
| WO | 2003101952 | A2 | 12/2003 | |
| WO | WO 08/155141 | | 12/2008 | |
| WO | 2011153493 | A2 | 12/2011 | |
| WO | 2013086354 | A1 | 6/2013 | |
| WO | 2014136086 | A1 | 9/2014 | |
| WO | 2015095346 | A1 | 6/2015 | |
| WO | WO 15/095340 | | 6/2015 | |
| WO | WO-2015095340 | A1 * | 6/2015 | ......... A61K 31/7105 |
| WO | 2016187531 | A1 | 11/2016 | |
| WO | WO 17/173054 | | 10/2017 | |
| WO | WO-2017173054 | A1 * | 10/2017 | ................ A61P 1/16 |
| WO | WO-2018011799 | A1 * | 1/2018 | ............. A61K 38/36 |
| WO | 2018220553 | A1 | 12/2018 | |
| WO | 2019008441 | A1 | 1/2019 | |
| WO | 2019099501 | A1 | 5/2019 | |
| WO | WO 19/089561 | | 5/2019 | |
| WO | WO 19/126378 | | 6/2019 | |
| WO | WO 20/028787 | | 2/2020 | |
| WO | 2020072605 | A1 | 4/2020 | |
| WO | 2020118041 | A1 | 6/2020 | |
| WO | 2020150320 | A1 | 7/2020 | |
| WO | 2020152037 | A1 | 7/2020 | |
| WO | WO 20/176856 | | 9/2020 | |
| WO | WO 20/176859 | | 9/2020 | |
| WO | WO 20/176868 | | 9/2020 | |
| WO | 2020219876 | A1 | 10/2020 | |
| WO | 2020246581 | A1 | 12/2020 | |
| WO | 2020247382 | A1 | 12/2020 | |
| WO | 2021021636 | A1 | 2/2021 | |
| WO | WO 21/021634 | | 2/2021 | |
| WO | 2021080847 | A1 | 4/2021 | |
| WO | 2021113365 | A1 | 6/2021 | |
| WO | 2021141969 | A1 | 7/2021 | |
| WO | 2022140238 | A1 | 6/2022 | |
| WO | 2022140239 | A1 | 6/2022 | |
| WO | 2022140252 | A1 | 6/2022 | |
| WO | 2022159421 | A1 | 7/2022 | |
| WO | 2022159463 | A1 | 7/2022 | |
| WO | 2022159472 | A1 | 7/2022 | |
| WO | 2022159475 | A1 | 7/2022 | |
| WO | 2022251665 | A1 | 12/2022 | |
| WO | 2023056917 | A1 | 4/2023 | |
| WO | 2023121971 | A1 | 6/2023 | |
| WO | 2023121975 | A1 | 6/2023 | |
| WO | 2024019936 | A1 | 1/2024 | |

OTHER PUBLICATIONS

Augustin et al., Aug. 25, 2017, Organotypic vasculature: from descriptive heterogeneity to functional pathophysiology, Science, 357:eeal2379, 13 pp.

Belliveau et al., "Microfluidic Synthesis of Highly Potent Limit-size Lipid Nanoparticles for In Vivo Delivery of siRNA", *Molecular Therapy—Nucleic Acids*, vol. 1, 2012, in 9 pages.

CAS Registry No. 751440-44-5, STN Entry Date Sep. 24, 2004; 3-octyl-6-[7-oxo-7-[2-[(1-oxooctadecyl)oxyl]-1-[[(1-oxooctadecyul)oxy]methyl]ethoxy]heptyl]-4-Cyclohexene-1,2-dicarboxylic acid.

Chen, et al., Rapid Discovery of Potent siRNA-Containing Lipid Nanoparticles Enabled by Controlled Microfluidic Formulation:, *J Am Chem Soc*, 2012, 134, pp. 6948-6951.

Cheng et al., Nov. 16, 2012, Multifunctional nanoparticles; cost versus benefit of adding targeting and imaging capabilities, Science, 338(6109):903-910.

Cullis et al., Jul. 7, 2017, Lipid nanoparticle systems for enabling gene therapies, Molecular Therapy, 25(7):1467-1475.

Dahlman et al., Aug. 2014, In vivo endothelial siRNA delivery using polymeric nanoparticles with low molecular weight, Nat Nano, 9(8):648-655.

Dang et al., Aug. 2017, Drugging the 'undruggable' cancer targets, Nature Reviews Cancer, 17(8):502-508.

Dixon et al., Dec. 2009, Identifying druggable disease-modifying gene products, Curr Opin Chem Biol, 13(5-6):549-555.

Elbashir et al., May 24, 2001, Duplexes of 21-nucleotide RNAs mediate RNA interference in cultured mammalian cells, Nature, 411:494 498.

Gelsema et al., 1996, Benzoolysis of diacylgylcerophosphocholines: dephosphorylation and sequential formation of isomeric reaction products, Journal of Lipid Research, 73(6):1224-1233.

Jenkins et al., 2018, Mechanisms of resistance to immune checkpoint inhibitors, BJC, 118:9-16.

Kedmi et al., 2018, A modular platform for targeted RNAi therapeutics, Nat Nanotechnol, 13:214-219.

Khalil et al., May 2016, The future of cancer treatment: immunomodulation, CARs and combination immunotherapy, Nat Rev Clin Oncol, 13(5):273-290.

Kumar et al., Aug. 22, 2008, T cell-specific siRNA delivery suppresses HIV-1 infection in humanized mice, Cell, 134:577-586.

Leung et al., 2012, Lipid nanoparticles containing siRNA synthesized by microfluidic mixing exhibit and electron-dense nanostructure core, J Phys Chem, 116:18440-18450.

Lokugamage et al., Aug. 29, 2019, Constrained nanoparticles deliver siRNA and sgRNA to T cells in vivo without targeting ligands, Advanced Materials, 31(41):1902251.

Lokugamage et al., Sep. 2018, Testing thousands of nanoparticles in vivo using DNA barcodes, Current Opinion in Biomedical Engineering, 7:1-8.

Lorenzer et al., 2015, Going beyond the liver: progress and challenges of targeted delivery of siRNA therapeutics, J Control Release, 203:1-15.

MacParland et al., 2017, Phenotype determines nanoparticle uptake by human macrophages from liver and blood, ACS Nano, 11:2428-2443.

Mathiowitz et al., "Novel microcapsules for delivery systems", *Reactive Polymers, Ion Exchangers, Sorbents*, vol. 6, No. 2-3, Oct. 1987, pp. 275-283.

Mathiowitz et al., "Polyanhydride microspheres as drug carriers I. Hot-melt microencapsulation", *Journal of Controlled Release*, vol. 5, No. 1, Jun. 1987, pp. 13-22.

Mathiowitz et al., "Polyanhydride microspheres as drug carriers. II. Microencapsulation by solvent removal", *Journal of Applied Polymer Science*, vol. 35, No. 3, Feb. 1988, pp. 755-774.

Paunovska et al., Aug. 28, 2018, Analyzing 2,000 in vivo drug delivery data points reveals cholesterol structure impacts nanoparticle delivery, ACS Nano, 12(8):8341-8349.

Paunovska et al., Mar. 14, 2018, A direct comparison of in vitro and in vivo nucleic acid delivery mediated by hundreds of nanoparticles reveals a weak correlation, Nano Lett, 18(3):2148-2157.

Platt et al., Oct. 9, 2014, CRISPR-Cas9 knockin mice for genome editing and cancer modeling, Cell, 159:440-445.

Pollastri et al., 2000, Synthesis, structure, and thermal properties of 1,2-diopalmitoylgalloylglycerol (DPGG), a novel self-adhering lipid, Chemistry and Physics of Lipids, 104(1):67-74.

Ramishetti et al., 2015, Systemic gene silencing in primary T lymphocytes using targeted lipid nanoparticles, ACS Nano, 9(7):6706-6716.

Sago et al., Dec. 12, 2018, Modifying a commonly expressed endocytic receptor retargets nanoparticles in vivo, Nano Lett, 18(12)7590-7600.

Sharma et al., Apr. 3, 2015, The future of immune checkpoint therapy, Science, 348(6230):56-61.

Tavares et al., Dec. 5, 2017, Effect of removing Kupffer cells on nanoparticle tumor delivery, PNAS, 114:E10871-e10880.

Tsol et al., Nov. 2016, Mechanism of hard nanomaterial clearance by the liver, Nat Mater, 15:1212-1221.

Ui-Tei et al., 2000, Sensitive assay of RNA interference in *Drosophila* and Chinese hamster cultured cells using firefly luciferase gene as target, FEBS Lett, 479:79-82.

International Search Report and Written Opinion dated Sep. 23, 2020 in application No. PCT/US2020/043512.

International Search Report for PCT/US2020/062893 dated Jun. 10, 2023 (7 pages).

(56) References Cited

OTHER PUBLICATIONS

International Search Report for PCT/US2021/012282 dated Mar. 3, 2021 (5 pages).
International Search Report for PCT/US2022/012867 dated Jun. 8, 2022 (5 pages).
International Search Report for PCT/US2022/053193 dated Jun. 29, 2023 (4 pages).
International Search Report for PCT/US2022/053193 dated May 3, 2023 (4 pages).
International Search Report for PCT/US2022/053209 dated Mar. 24, 2023 (5 pages).
International Search Report for PCT/US2023/027741 dated Oct. 13, 2023 (3 pages).
International Search Report for PCT/US22/12951 dated May 23, 2022 (5 pages).
"SID 402741750", PubChem, National Center for Biotechnology Information, SID 402741750, Jan. 23, 2020, retrieved Mar. 21, 2022 from URL: https://pubchem.ncbi.nlm.nih.gov/substance/402741750, (5 pages).
"SID 46481541", PubChem, National Center for Biotechnology Information, SID 46481541, Dec. 12, 2007, retrieved May 10, 2022 from URL: https://pubchem.ncbi.nlm.nih.gov/substance/46481541, (5 pages).
"Tris(deoxycholic acid)1,3,5-benzenetriyltris(methylene) ester", PubChem, National Center for Biotechnology Information, SID 274013917, Dec. 18, 2015, retrieved Mar. 21, 2022 from URL: https://pubchem.ncbi.nlm.nih.gov/substance/274013917, (2 pages).
Brown, William H., et al., "Organic Chemistry", Second Edition, Saunders College Publishing, 1995, pp. 169 (3 pages).
Chenthamara, et al., "Therapeutic efficacy of nanoparticles and routes of administration", Biomaterials Research, vol. 23, No. 20, Nov. 21, 2019, DOI:10.1186/s40824-019-0166-x (29 pages).
Diab, Hadeer M., et al., "ZnO-Nanoparticles-Catalyzed Synthesis of Poly(tetrahydrobenzimidazo[2,1-b]quinazolin-1(2H)-ones) as Novel Multi-armed Molecules", Synlett, vol. 29, No. 12, 2018, pp. 1627-1633, DOI: 10.1055/s-0037-1609967, (7 pages).
Epand, et al., "Role of the position of unsaturation on the phase behavior and intrinsic curvature of phosphatidylethanolamines", Biophysical Journal, vol. 71, No. 4, pp. 1806-1810, Oct. 1996, DOI:10.1016/S0006-3495(96)79381-5 (5 pages).
Fenton, et al., "Synthesis and Biological Evaluation of Ionizable Lipid Materials for the In Vivo Delivery of Messenger RNA to B Lymphocytes", Advanced materials (Deerfield Beach, Fla.), vol. 29, No. 33, Sep. 2017, DOI:10.1002/adma.201606944 (7 pages).
Funakoshi, Yuka , et al., "Effect of Alkyl Chain Length and Unsaturation of the Phospholipid on the Physicochemical Properties of Lipid Nanoparticles", Chem. Pharm. Bull., vol. 63, No. 9, 2015, pp. 731-736 (6 pages).
Heidenreich, Olaf , et al., "High Activity and Stability of Hammerhead Ribozymes Containing 2'-Modified Pyrimidine Nucleosides and Phosphorothioates", The Journal of Biological Chemistry, vol. 269, Jan. 21, 1994, pp. 2131-2138 (8 pages).
Junquera, Elena , et al., "Recent progress in gene therapy to deliver nucleic acids with multivalent cationic vectors", Advances in Colloid and Interface Science, vol. 233, 2016, pp. 161-175, (15 pages).
Karikó, Katalin , et al., "Incorporation of Pseudouridine Into mRNA Yields Superior Nonimmunogenic Vector With Increased Translational Capacity and Biological Stability", Molecular Therapy, vol. 16, No. 11, Nov. 2008, pp. 1833-1840, DOI:10.1038/mt.2008.200 (8 pages).
Kozak, Marilyn , "An analysis of 5'-noncoding sequences from 699 vertebrate messenger RNAs", Nucleic Acids Research, vol. 15, No. 20, 1987, pp. 8125-8148 (24 pages).
Lokugamage, Melissa P., et al., "Constrained Nanoparticles Deliver siRNA and sgRNA to T Cells In Vivo without Targeting Ligands", Advanced Materials, vol. 31, Issue 41, No. 1902251, Aug. 29, 2019, DOI: 10.1002/adma.201902251, Supporting Information (32 pages).
Makarova, Kira M., et al., "An updated evolutionary classification of CRISPR-Cas systems", Nature Reviews Microbiology, vol. 13, 2015, pp. 722-736, DOI: 10.1038/nrmicro3569, (15 pages).
Reichmuth, et al., "mRNA vaccine delivery using lipid nanoparticles", Therapeutic Delivery, vol. 7, No. 5, pp. 319-334, 2016, DOI:10.4155/tde-2016-0006 (16 pages).
Sago, Cory D., et al., "High-throughput in vivo screen of functional mRNA delivery identifies nanoparticles for endothelial cell gene editing", PNAS, vol. 115, No. 43, 2018, pp. E9944-E9952, DOI: 10.1073/pnas.1811276115, (9 pages).
Sago, Cory D., et al., "Nanoparticles That Deliver RNA to Bone Marrow Identified by in Vivo Directed Evolution", Journal of the American Chemical Society, vol. 140, No. 49, 2018, pp. 17095-17105, DOI: 10.1021/jacs.8b08976, Author Manuscript (23 pages).
Scheidt, et al., "The interaction of small molecules with phospholipid membranes studied by 1H NOESY NMR under magic-angle spinning", Acta Pharmacologica Sinica, vol. 29, No. 1, 2008, pp. 35-49, DOI:10.1111/j.1745-7254.2008.00726.x (15 pages).
Shmakov, Sergey, et al., "Discovery and Functional Characterization of Diverse Class 2 CRISPR-Cas Systems", Molecular Cell, vol. 60, No. 3, 2015, pp. 385-397, DOI: 10.1016/j.molcel.2015.10.008, (14 pages).
Wang, et al., "Effects of various numbers and positions of cis double bonds in the sn-2 acyl chain of phosphatidylethanolamine on the chain-melting temperature", The Journal of Biological Chemistry, vol. 274, No. 18, pp. 12289-12299. Apr. 30, 1999, DOI:10.1074/jbc.274.18.12289 (11 pages).
Yokoe, Hiroko, et al., "Spatial dynamics of GFP-tagged proteins investigated by local fluorescence enhancement", Nature Biotechnology, vol. 14, Oct. 1996, pp. 1252-1256 (5 pages).
Zetsche, Bernd, et al., "Cpf1 Is a Single RNA-Guided Endonuclease of a Class 2 CRISPR-Cas System", Cell, vol. 163, No. 3, 2015, pp. 759-771, DOI: 10.1016/j.cell.2015.09.038, (15 pages).
Gan Z, Lokugamage MP, Hatit MZC, et al. Nanoparticles containing constrained phospholipids deliver mRNA to liver immune cells in vivo without targeting ligands. Bioeng Transl Med. 2020;5:e10161. pp. 1-11. https://doi.org/10.1002/btm2.10161.

* cited by examiner

Ionizable Lipid $R_1$: Tail Variations

L

S

A $R_2$: Head Group Variations 1 2 3 4 5 6 7 8 9 10 11

11-A gsgsgsCGAsGsGfsAfsGfsCfUGfUfUCAfCfCGgUUUUA (SEQ ID NO:1)
GagcuagaaauagcaaGUUaAaAuAaggcuaGUccGUUAu
cAAcsusus gsasasasasasgugGscascscsgsasgsuscgsg susgscsusususususu A, G, U, C: RNA nucleotide
Nf: 2'-Fluoro nucleotide
a, g, u, c: 2'-O-Methyl nucleotide
s: phosphorothioate

NANOMATERIALS CONTAINING CONSTRAINED LIPIDS AND USES THEREOF

INCORPORATION BY REFERENCE TO ANY PRIORITY APPLICATIONS

This application is a U.S. National Phase of International Application No. PCT/US2020/043512, filed on Jul. 24, 2020, which claims the benefit of U.S. Provisional Application No. 62/879,731 filed Jul. 29, 2019, entitled, "NANOMATERIALS CONTAINING CONSTRAINED LIPIDS AND USES THEREOF", both of which are incorporated herein by reference in their entireties.

FIELD

The subject matter described herein is generally related to drug delivery systems and methods of their use.

REFERENCE TO SEQUENCE LISTING

The present application is being filed along with an Electronic Sequence Listing. The Electronic Sequence Listing is provided as a file entitled GUIDE005WO.txt, created and last modified on Jul. 4, 2020, which is 6,977 bytes in size. The information in the electronic format of the Electronic Sequence Listing is incorporated herein by reference in its entirety.

BACKGROUND

T lymphocytes regulate immune responses making them important drug targets for developing new medicines. For example, antibody therapies that block cytotoxic T lymphocyte associated antigen 4 (CTLA4), programmed cell death protein 1 (PD1), or PD1 ligand 1 (PDL1)) signaling have driven potent anti-tumor responses (Khalil, D. N., et al., *Nat Rev Clin Oncol,* 13:273-290 (2016); Sharma, P. & Allison, J. P., *Science,* 348:56-61 (2015)). However, a large number of patients do not respond to these agents, and many of those who do respond eventually relapse (Jenkins, T, et al., *BJC,* 118:9-16 (2018)). Additionally, antibody therapies can only inhibit the activity of 'druggable' proteins, which are thought to constitute ~15% of the total protein coding genome (Dixon, S. and Stockwell, B., *Curr Opin Chem Biol,* 13(5-6):549-555 (2009)).

Some proteins that play important roles in disease pathology are "undruggable." The term 'undruggable' was coined to describe proteins that could not be targeted pharmacologically (Cang, C. V., et al., *Nature Reviews Cancer,* 17:502-508 (2017)). Today, there are many cancer targets that are considered undruggable (Cang, C. V., et al., *Nature Reviews Cancer,* 17:502-508 (2017)). Examples of undruggable proteins include intracellular proteins and proteins that lack domains that are readily bound by small molecule drugs.

Antibody therapies are limited to druggable proteins because the antibody must be able to bind to the protein to exert its therapeutic effect. siRNA can be used to inhibit the translation of any gene including genes that encode an undruggable protein. Several undruggable protein targets have been identified in T cell activity. Thus, siRNA can be useful to treat a large number of diseases caused by 'undruggable' proteins including diseases involving T cells. Unfortunately, clinically relevant siRNA delivery to cells other than hepatocytes (Adams, D., et al., *N Engl J Med,* 379:11-21 (2018)) has remained challenging (Lorenzar, C., et al., *J Control Release,* 203:1-15 (2015)). Although several advances have been made in T cell siRNA delivery, several obstacles remain. For example, siRNA was delivered to T cells using a single chain antibody linked to a positively charged peptide; this led to target gene silencing at 5 mg/kg, a high dosage (Kumar, P., et al., *Cell,* 134:577-586 (2008)). In a second example, nanoparticles were coated with anti-CD4 antibodies, leading to 20% in vivo target gene silencing at 1 mg/kg doses (Ramishetti, S., et al., *ACS Nano,* 9:6706-6716 (2015)). More recently, lipid nanoparticles (LNPs) that target hepatocytes were re-targeted to T cells by coating them with CD4 antibodies, leading to 50% in vivo T cell gene silencing at 6 mg/kg doses (Kedmi, R., et al., *Nat Nanotechnol,* 13:214-219 (2018)). All these therapies share two important commonalities. First, they require more than 1 mg/kg siRNA to achieve 50% gene silencing, which is above the current siRNA dose approved for human use (Adams, D., et al., *N Engl J Med,* 379:11-21 (2018)). Second, they achieve T cell delivery using peptide-, protein-, or aptamer-based targeting ligands.

Nanomedicines are often trafficked to cell using targeting ligands (Cheng, S., et al., *Science,* 338:903-910 (2012)). However, the only FDA approved RNA nanoparticle therapy utilizes a simple mixture of lipids that are naturally trafficked to hepatic cells (Adams, D., et al., *N Engl J Med,* 379:11-21 (2018)). Natural trafficking has not been shown to promote nanoparticle delivery to immune cells. Because the current options for nanoparticle delivery to T cells require high doses of nucleic acid to achieve gene silencing and rely on targeting ligands for cell delivery, there is a need for improved nanoparticle compositions for delivery to T cells.

It is therefore an object of the invention to provide delivery vehicles that can deliver nucleic acids to immune cells and methods of their use.

It is another object of the invention to provide methods of modulating immune cell function.

SUMMARY

Compositions for delivering nucleic acids to specific cells or tissue microenvironments are provided. In one embodiment, the compositions are lipid nanoparticle compositions formulated to have reduced splenic and hepatic clearance. It has been discovered that the chemical composition of lipid nanoparticles significantly influences the natural trafficking of the lipid nanoparticles. More specifically, it has been discovered that conformationally constrained ionizable lipids can modify the tropism and clearance profile of lipid nanoparticles without the need of a targeting ligand. It has also been discovered that tropism of the disclosed lipid nanoparticles is size-independent.

One embodiment provides an ionizable lipid nanoparticle having a conformationally constrained ionizable lipid, a phospholipid, a polyethylene glycol-lipid; a cholesterol, and optionally a nucleic acid. In one embodiment, the constrained ionizable lipid has a structure according to Formula I:

Formula I

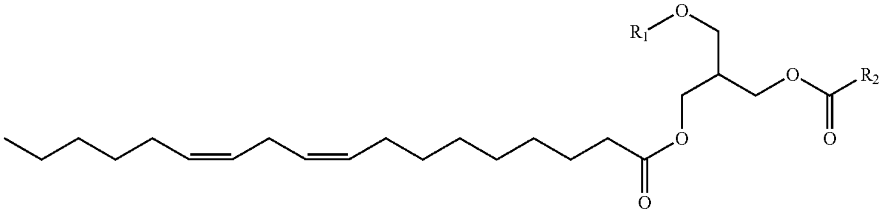

wherein:

$R_1$ is

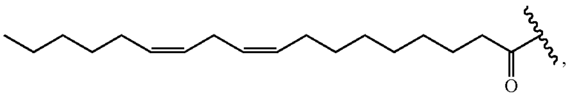,

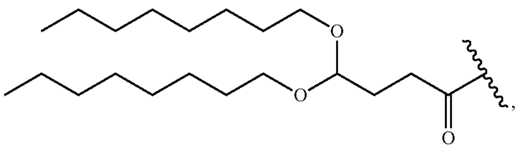, or

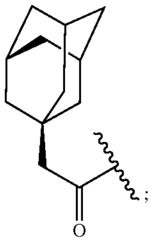;

and $R_2$ is

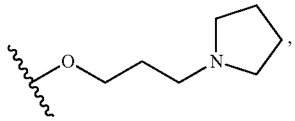,

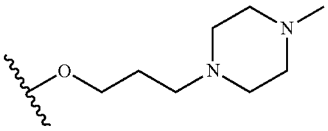, 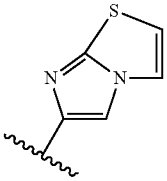,

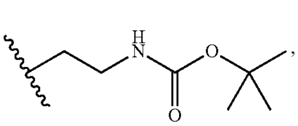, 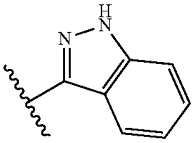,

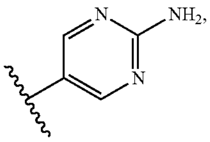 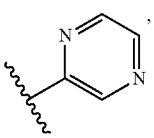, 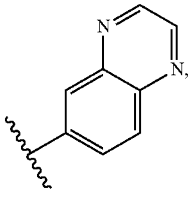

-continued

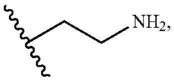 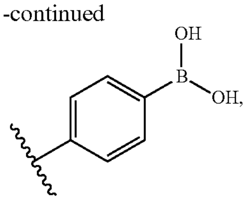 or

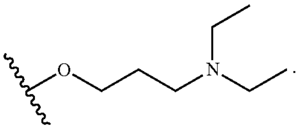.

In another embodiment the constrained ionizable lipid contains an adamantane tail. In some embodiments the constrained ionizable lipid is 3-[(1-Adamantanyl)acetoxy]-2-{[3-(diethylamino)propoxycarbonyloxy]methyl}propyl (9Z,12Z)-9,12-octadecadienoate. In some embodiments, the phosphlipid is 1-2-distearoyl-sn-glycero-3-phosphocholine (DSPC) or 1-2-dioleoyl-sn-glycero-3-phosphoethanolamine (DOPE). In some embodiments, the PEG-lipid is $C_{14}PEG_{2000}$ or $C_{18}PEG_{2000}$. In some embodiments, lipid nanoparticles contain a sterol. In some embodiments, the sterol is cholesterol. The nucleic acid can be RNA, DNA, single-stranded RNA, single-stranded DNA, double-stranded RNA, double stranded DNA, triple-stranded DNA, siRNA, shRNA, sgRNA, mRNA, miRNA, antisense DNA, or a combination thereof.

In some embodiments, the nucleic acid encodes an RNA-guided DNA endonuclease, including but not limited to Cas9, CasX, CasY, Cas13, or Cpf1.

In one embodiment the lipid nanoparticles contain about 30 mol % to about 70 mol % conformationally constrained ionizable lipid, about 5 mol % to about 25 mol % phospholipid, about 25 mol % to about 45 mol % cholesterol, and about 0.1 mol % to about 5 mol % PEG-lipid. In other embodiments, the conformationally constrained ionizable lipid can be present at 35, 45, 50, or 65 mole percent.

In some embodiments, the nanoparticle has a hydrodynamic diameter from about 30 nm to about 170 nm. In another embodiment, the lipid nanoparticles have an average diameter of 50 nm to 100 nm.

The disclosed lipid nanoparticles can be formulated as a pharmaceutical composition optionally containing a pharmaceutically acceptable excipient or pharmaceutically acceptable carrier.

One embodiment provides lipid nanoparticles in which $C_{14}PEG_{2000}$ is present at 2.0 to 3.0 mole percent, DSPC is present at 15 to 17 mole percent, cholesterol is present at 45 to 47 mole percent, and the constrained lipid is present at 33 to 36 mole percent.

Still another embodiment provides a method of delivering a therapeutic or prophylactic agent to a subject in need thereof, by administering to the subject one or more of the disclosed lipid nanoparticle compositions loaded with a therapeutic nucleic acid, for example a nucleic acid encoding a therapeutic protein, or an inhibitory or enzymatic nucleic acid. The method can further include administering a second therapeutic agent. In one embodiment, the nanoparticles preferentially deliver cargo to immune cells. The immune cells can be T cells, such as CD8+ T cells, CD4+ T cells, or T regulatory cells. The immune cells can also be macrophages or dendritic cells.

One embodiment provides a method for reducing splenic or hepatic clearance of a nanoparticle composition by formulating the nanoparticles with an effective amount of conformationally constrained ionizable lipid to reduce or inhibit splenic or hepatic clearance of the nanoparticles.

Another embodiment provides a method of delivering a nucleic acid to an immune cell in a subject in need thereof by administering to the subject a lipid nanoparticle consisting of 3-[(1-Adamantanyl)acetoxy]-2-{[3-(diethylamino) propoxycarbonyloxy]methyl}propyl (9Z,12Z)-9,12-octadecadienoate, DSPC, a polyethylene glycol-lipid, a cholesterol, and the nucleic acid, wherein the lipid nanoparticle composition delivers the nucleic acid to the immune cell in the subject, optionally in the absence of a targeting ligand. In one embodiment the T cell is a CD8+ T cell.

Yet another embodiment provides a method for reducing gene expression in an immune cell in a subject in need thereof by administering to the subject a lipid nanoparticle composition consisting of 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and an inhibitory nucleic acid, wherein the lipid nanoparticle composition delivers the inhibitory nucleic acid to the immune cell in the subject.

Another embodiment provides a method for editing a gene in an immune cell in a subject in need thereof by administering to the subject a lipid nanoparticle composition comprising a first and second population of lipid nanoparticles, wherein the first population of lipid nanoparticles consist of 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and sgRNA specific for a the gene, and wherein the second population of lipid nanoparticles consist of 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and mRNA encoding an RNA guided DNA endonuclease.

DETAILED DESCRIPTION

I. Definitions

Figure 1A:
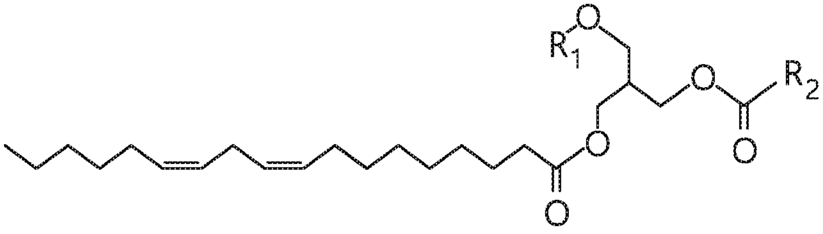
FIG. 1A is the structure of an ionizable lipid scaffold to which tail variants (structure shown in FIG. 1B) and head group variants (structures shown in FIG. 1C) were added.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms “a,” “an,” “the,” and similar referents in the context of describing the presently claimed invention (especially in the context of the claims) are to be construed to cover both the singular and the plural, unless otherwise indicated herein or clearly contradicted by context.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Recitation of ranges of values herein are merely intended to serve as a shorthand method of referring individually to each separate value falling within the range, unless otherwise indicated herein, and each separate value is incorporated into the specification as if it were individually recited herein.

Use of the term “about” is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2/o; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

As used herein, an “RNA” refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide. RNAs may be selected from the nonlimiting group consisting of small interfering RNA (siRNA), microRNA (miRNA), Dicer-substrate RNA (dsRNA), small hairpin RNA (shRNA), mRNA, single-guide RNA (sgRNA), cas9 mRNA, and mixtures thereof.

The terms “polypeptide”, “peptide”, and “protein”, may be used interchangeably to refer a string of at least three amino acids linked together by peptide bonds. Peptide may refer to an individual peptide or a collection of peptides. Peptides can contain natural amino acids, non-natural amino acids (i.e., compounds that do not occur in nature but that can be incorporated into a polypeptide chain), and/or amino acid analogs. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. Modifications may include cyclization of the peptide, the incorporation of D-amino acids, etc.

As used herein, the terms “treat,” “treating,” “treatment” and “therapeutic use” refer to the elimination, reduction or amelioration of one or more symptoms of a disease or disorder. As used herein, a “therapeutically effective amount” refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term “prophylactic agent” refers to an agent that can be used in the prevention of a disorder or disease prior to the detection of any symptoms of such disorder or disease. A “prophylactically effective” amount is the amount of prophylactic agent sufficient to mediate such protection. A prophylactically effective amount may also refer to the amount of the prophylactic agent that provides a prophylactic benefit in the prevention of disease.

As used herein, the terms “individual,” “host,” “subject,” and “patient” are used interchangeably herein, and refer to a mammal, including, but not limited to, humans, rodents, such as mice and rats, and other laboratory animals.

As used herein, the term “pharmaceutically acceptable carrier” encompasses any of the standard pharmaceutical carriers, such as a phosphate buffered saline solution, water and emulsions such as an oil/water or water/oil emulsion, and various types of wetting agents.

As used herein, the term “conformationally constrained lipid” refers to a lipid whose molecular structure is predominantly in one architecture, such as an adamantane, whose shape resembles an ‘armchair’.

The term “PEG-lipid” refers to a lipid modified with polyethylene glycol. Exemplary PEG-lipids, include but are not limited to $C_{14}PEG_{350}$, $C_{14}PEG_{1000}$, $C_{14}PEG_{2000}$, $C_{14}PEG_{3000}$, and $C_{18}PEG_{2000}$.

The term “oligonucleotide” refers to short DNA, RNA, or DNA-RNA molecules or oligomers containing a relatively small number of nucleotides.

Some embodiments described herein related to a compound of Formula (I):

(I)
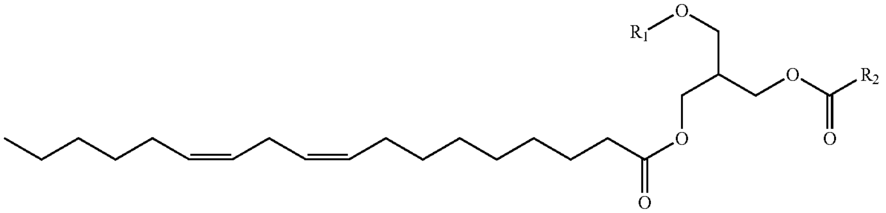
in which $R_1$ is:
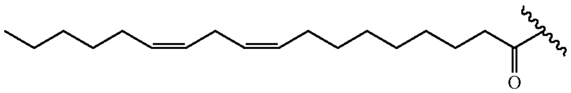,
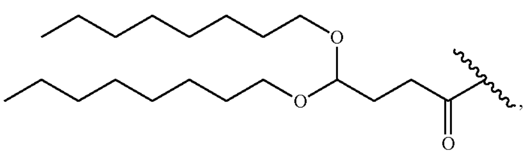,
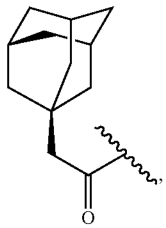, or 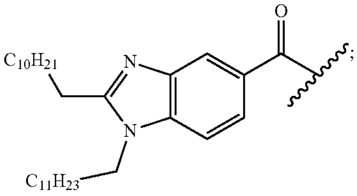;
$R_2$ is:
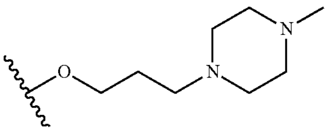,
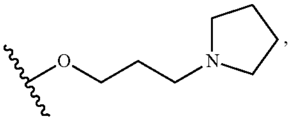,
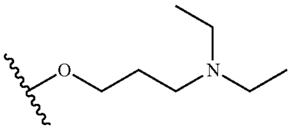, 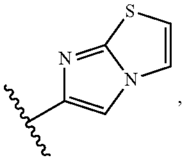,
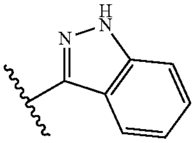, 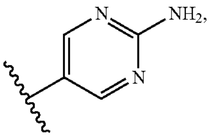
-continued
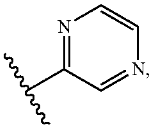 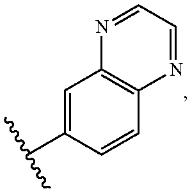,
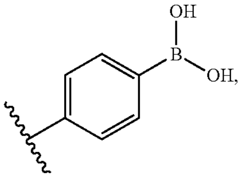 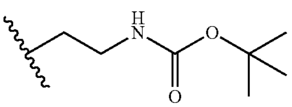,
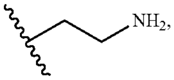 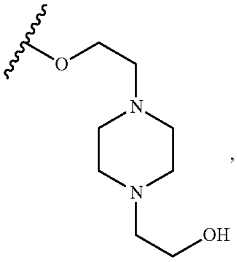,
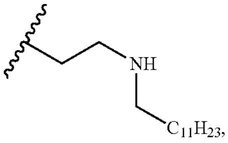 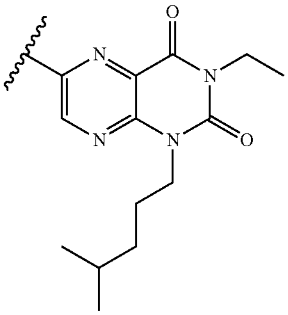, or
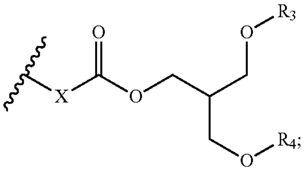
in which X is
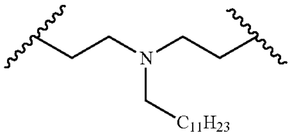
or -continued

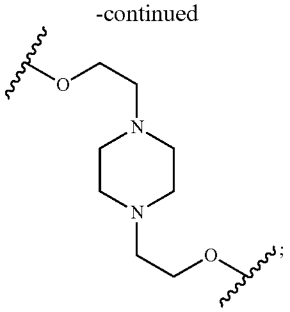

and $R_3$ and $R_4$ are each independently

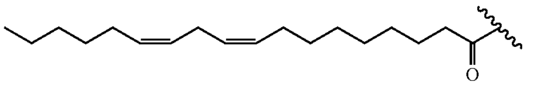

or

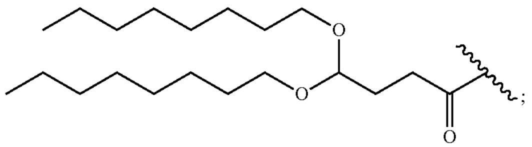

Some embodiments relate to a compound of Formula (III):

(III)

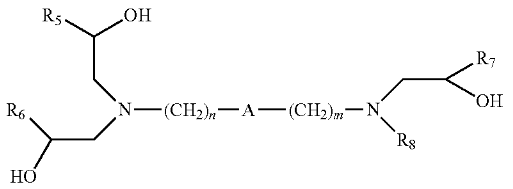

in which:

$R_8$ is —H or

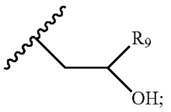

$R_5$, $R_6$, $R_7$, and $R_9$ are each independently: —$C_8H_{17}$, —$C_{10}H_{21}$, —$C_{12}H_{25}$, —$C_{13}H_{27}$, —$C_{14}H_{29}$, $C_{16}H_{33}$, or adamantanyl, m and n are each independently 0, 1, 2, 3, or 4;

A is

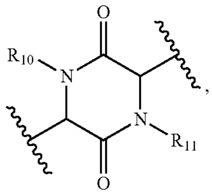

,

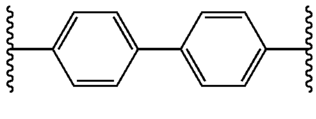

,

-continued

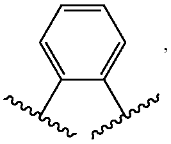

, —O—,

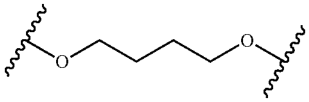

,

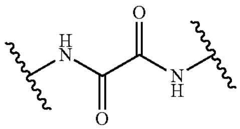

,

—S—,

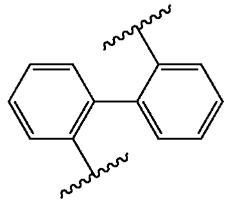

,

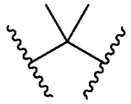

,

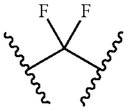

,

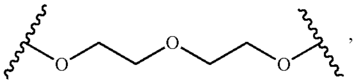

, or

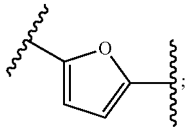

$R_{10}$ and $R_{11}$ are each independently —H or

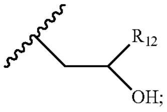

and $R_{12}$ is —$C_{10}H_{21}$.

Some embodiments relate to a compound in which $R_2$ is

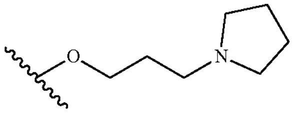

or

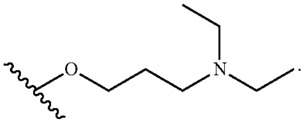

Some embodiments relate to a lipid nanoparticle composition comprising: a conformationally constrained ionizable lipid; a phospholipid; a polyethylene glycol-lipid; a cholesterol; and optionally a nucleic acid. Some embodiments relate to a lipid nanoparticle in which the conformationally constrained ionizable lipid comprises a structure according to a structure described herein. Some embodiments relate to a lipid nanoparticle composition in which the amount of conformationally constrained ionizable lipid present is in the range of about 35 to about 65 mole percent, based on total moles.

Some embodiments relate to a lipid nanoparticle composition in which the conformationally constrained ionizable lipid has a structure according to

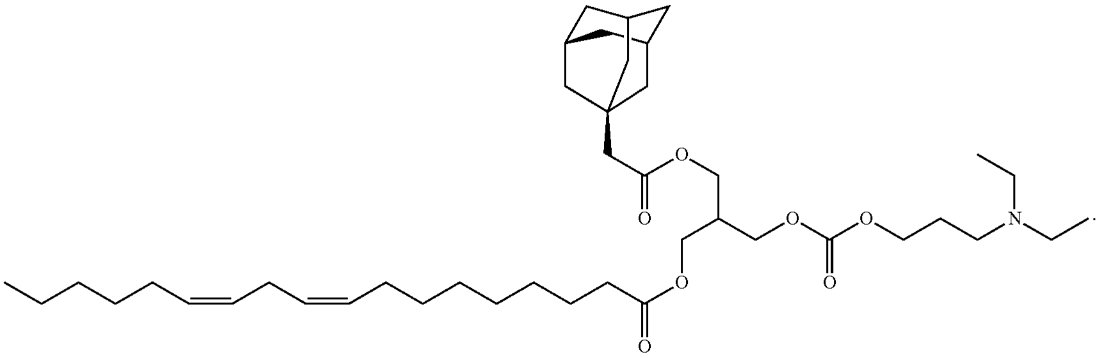 [SMILES: CCCCC/C=C\C/C=C\CCCCCCCC(=O)OCC(COC(=O)C[C@]12CC3CC(C[C@@H](C3)C1)C2)COC(=O)OCCCN(CC)CC]

Some embodiments relate to a lipid nanoparticle composition in which the conformationally constrained ionizable lipid has a structure according to

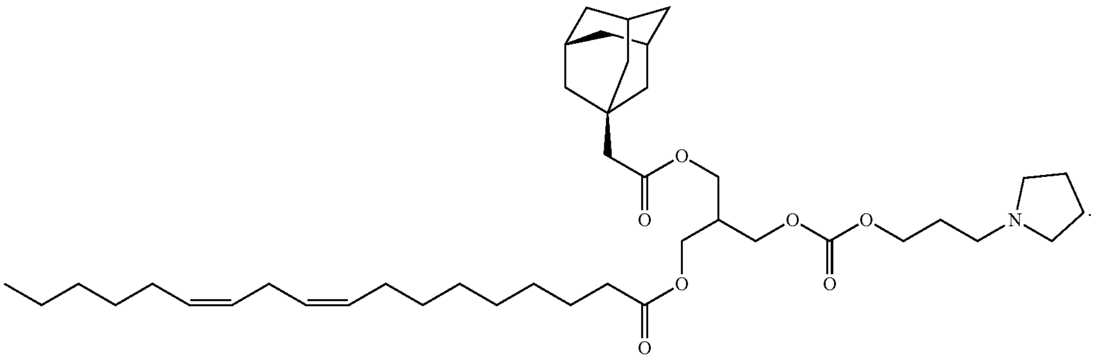 [SMILES: CCCCC/C=C\C/C=C\CCCCCCCC(=O)OCC(COC(=O)C[C@]12CC3CC(C[C@@H](C3)C1)C2)COC(=O)OCCCN1CCCC1]

Some embodiments relate to a lipid nanoparticle composition in which the phospholipid is 1-2-distearoyl-sn-glycero-3-phosphocholine (DSPC). Some embodiments relate to a lipid nanoparticle composition in which the polyethylene glycol-lipid is $C_{14}PEG_{2000}$ or $C_{18}PEG_{2000}$.

Some embodiments relate to a lipid nanoparticle composition in which the composition comprises about 30 mol % to about 70 mol % conformationally constrained ionizable lipid, about 5 mol % to about 25 mol % phospholipid, about 25 mol % to about 45 mol % cholesterol, and about 0.1 mol % to about 5 mol % polyethylene glycol-lipid.

Some embodiments relate to a lipid nanoparticle composition in which the nucleic acid comprises RNA, DNA, single-stranded RNA, single-stranded DNA, double-stranded RNA, double stranded DNA, triple-stranded DNA, siRNA, shRNA, sgRNA, mRNA, miRNA, antisense DNA, or a combination thereof. In some embodiments, the lipid nanoparticle composition is one in which the nucleic acid encodes a protein. In some embodiments, the lipid nanoparticle composition is one in which the nucleic acid encodes an RNA-guided DNA endonuclease. In some embodiments, the lipid nanoparticle composition is one in which the RNA-guided DNA endonuclease is Cas9, CasX, CasY, Cas13, or Cpf1.

In some embodiments, the nanoparticle composition is one in which the lipid nanoparticle has a hydrodynamic diameter in the range of from about 30 nm to about 170 nm.

In some embodiments, the lipid nanoparticle composition comprises: a conformationally constrained ionizable lipid comprising an adamantane tail; 1-2-distearoyl-sn-glycero-3-phosphocholine (DSPC); $C_{14}PEG_{2000}$; cholesterol; and siRNA. In some embodiments of the lipid nanoparticle, the conformationally constrained ionizable lipid is 3-[(1-Adamantanyl)acetoxy]-2-{[3-(diethylamino)propoxycarbonyloxy]methyl}propyl (9Z,12Z)-9,12-octadecadienoate.

In some embodiments of the lipid nanoparticle, $C_{14}PEG_{2000}$ is present at about 2.0 to about 3.0 mole percent, DSPC is present at about 15 to about 17 mole percent, cholesterol is present at about 45 to about 47 mole percent, the conformationally constrained ionizable lipid is present at about 33 to about 36 mole percent, and the siRNA is present at 5 to 20 mass ratio of total lipid to siRNA. In some embodiments, $C_{14}PEG_{2000}$ is present at about 2.5 mole percent, DSPC is present at about 16 mole percent, cholesterol is present at about 46.5 mole percent, and the conformationally constrained ionizable lipid is present at about 35 mole percent.

Some embodiments relate to a pharmaceutical composition comprising a lipid nanoparticle composition as described herein and a pharmaceutically acceptable excipient.

Some embodiments relate to a method of delivering a nucleic acid to a subject in need thereof, comprising, administering to the subject a lipid nanoparticle composition or a pharmaceutical composition as described herein. Some embodiments further comprise administering a second therapeutic agent to the subject.

Some embodiments relate to a method of delivering a nucleic acid to an immune cell in a subject in need thereof, comprising: administering to the subject a lipid nanoparticle composition consisting of 3-[(1-Adamantanyl)acetoxy]-2-{[3-(diethylamino)propoxycarbonyloxy]methyl}propyl (9Z, 12Z)-9,12-octadecadienoate; DSPC; a polyethylene glycol-lipid; a cholesterol; and a nucleic acid, in which the lipid nanoparticle composition delivers the nucleic acid to the immune cell in the subject. In some embodiments, the lipid nanoparticle composition does not contain a targeting ligand that targets the lipid nanoparticle composition to the immune cell. In some embodiments, the immune cell is a T cell. In some embodiments, the T cell is a CD8+ T cell. In some embodiments, the T cell is a T regulatory cell. In some embodiments, the T cell is CD4+. In some embodiments, the immune cell is a macrophage, dendritic cell, or liver immune cell.

Some embodiments relate to a method for reducing splenic or hepatic clearance of a nanoparticle composition comprising formulating the nanoparticle composition with an amount of a conformationally constrained ionizable lipid that is effective to reduce or inhibit splenic or hepatic clearance of the nanoparticle composition when administered to a subject. In some embodiments, the conformationally constrained ionizable lipid comprises a structure as described herein.

Some embodiments relate to a method for increasing delivery of a nanoparticle composition to non-hepatocyte cells in a subject comprising formulating the nanoparticle composition to comprise an amount of a conformationally constrained ionizable lipid that is effective to increase delivery of the nanoparticle composition to non-hepatocyte cells when administered to the subject. In some embodiments, the conformationally constrained ionizable lipid comprises a structure as described herein. In some embodiments, the nanoparticle composition is a lipid nanoparticle pharmaceutical composition. In some embodiments, the lipid nanoparticle pharmaceutical composition comprises a phospholipid, a polyethylene glycol-lipid, a cholesterol, and optionally a first nucleic acid. In some embodiments, the non-hepatocyte cells are at least one of splenic B cells, splenic T cells, lung endothelial cells, and liver immune cells. In some embodiments, the nanoparticle composition further comprises a second nucleic acid that is delivered to the subject in an amount in the range of about 0.5 mg/kg to about 2.0 mg/kg. In some embodiments, the amount of the second nucleic acid delivered to the subject is less than about 1.0 mg/kg.

Some embodiments relate to a method for reducing gene expression in an immune cell in a subject in need thereof, comprising: administering to the subject a lipid nanoparticle composition consisting of 3-[(1-Adamantanyl)acetoxy]-2-{[3-(diethylamino)propoxycarbonyloxy]methyl}propyl (9Z,12Z)-9,12-octadecadienoate; DSPC; a polyethylene glycol-lipid; cholesterol; and an inhibitory nucleic acid, in which the lipid nanoparticle composition delivers the inhibitory nucleic acid to the immune cell in the subject. In some embodiments, the inhibitory nucleic acid is siRNA. In some embodiments, the amount of the inhibitory nucleic acid administered to the subject is less than about 1.0 mg/kg. In some embodiments, the amount of inhibitory nucleic acid administered to the subject is about 0.5 mg/kg.

Some embodiments relate to a method for editing a gene in an immune cell in a subject in need thereof, comprising: administering to the subject a lipid nanoparticle composition comprising a first and second population of lipid nanoparticles, in which the first population of lipid nanoparticles consists of 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and sgRNA specific for the gene, and in which the second population of lipid nanoparticles consists of 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and mRNA encoding an RNA guided DNA endonuclease. In some embodiments, the RNA guided DNA endonuclease is selected from the group consisting of Cas9, CasX, CasY, Cas13, and Cpf1. In some embodiments, the amount of one or both of the sgRNA and mRNA administered to the subject is less than about 1.0 mg/kg. In some embodiments, the amount of one or both of the sgRNA and mRNA administered to the subject is about 0.5 mg/kg.

II. Lipid Nanoparticles

Effective, targeted delivery of biologically active substances such as small molecule drugs, proteins, and nucleic acids is a continuing challenge in the field of medicine. The delivery of nucleic acids specifically is made difficult by the relative instability and low cell permeability of nucleic acids. It has been discovered that lipid nanoparticles having constrained lipids can more effectively deliver nucleic acids to specific tissues in the body. In one embodiment, lipid nanoparticles can be formulated by mixing nucleic acids with conformationally constrained ionizable lipids, PEG-lipids, phospholipids, cholesterol, and optionally a nucleic acid. An exemplary lipid nanoparticle formulation includes the conformationally constrained ionizable lipid 3-[(1-Adamantanyl)acetoxy]-2-{[3-(diethylamino)propoxycarbonyloxy]methyl}propyl (9Z,12Z)-9,12-octadecadienoate, a PEG-lipid, 1,2-Distearoyl-sn-glycero-3-phosphocholine (DSPC), and cholesterol. In some embodiments, the lipid nanoparticles do not contain a targeting ligand. In some embodiments, the disclosed lipid nanoparticles preferentially target T cells over hepatocytes in the absence of a targeting ligand.

Lipid nanoparticle sizes vary. In one embodiment, the lipid nanoparticles can have a hydroscopic diameter from between about 30 to about 170 nm. The lipid nanoparticles can have a diameter that is about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, or 170 nm. In another embodiment the nanoparticles have a diameter from between 50 nm to 100 nm.

A. Ionizable Lipids

In one embodiment, the disclosed lipid nanoparticles include an ionizable lipid. The ionizable lipid typically includes an amine-containing on the head group. In one embodiment, the ionizable lipid is a conformationally constrained ionizable lipid. In some embodiments, the conformationally constrained lipid is present at 35, 45, 50, or 65 mole percent. In another embodiment, the conformationally constrained lipid is present at about 33 mol % to about 36 mol %. In yet another embodiment, the conformationally constrained lipid is present at 35 mol %. One embodiment provides a LNP containing a lipid having a structure according to Formula I:

Formula I
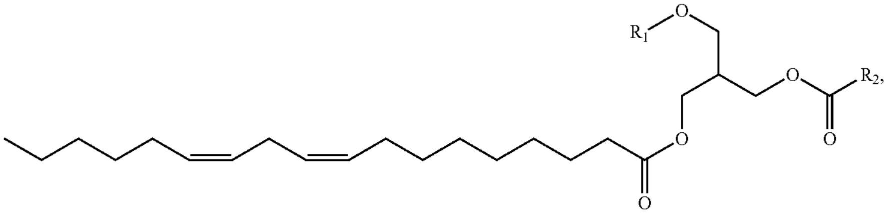
wherein $R_1$ is a lipid tail selected from the group consisting of;
L
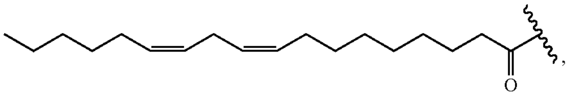
S
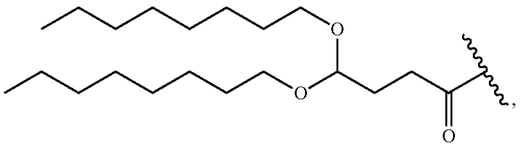
or
A
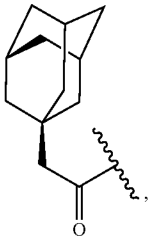
and
$R_2$ is a head group selected from the group consisting of:
(1)
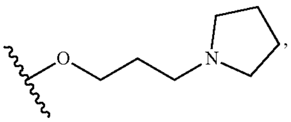
(2)
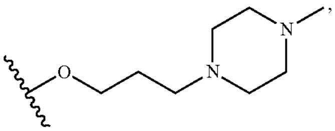
(3)
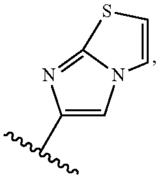
-continued
(4)
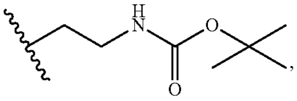
(5)
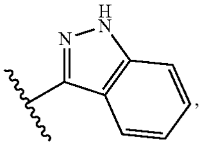
(6)
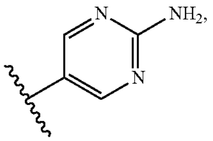
(7)
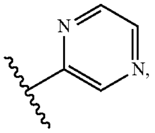
(8)
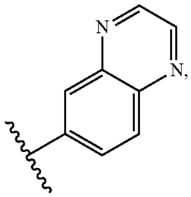
(9)
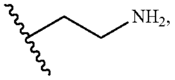
(10)
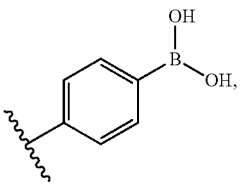
or
(11)
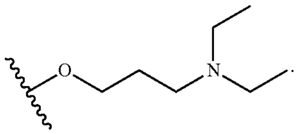
Another embodiment provides an ionizable lipid having a structure according to Formula II:

Formula II

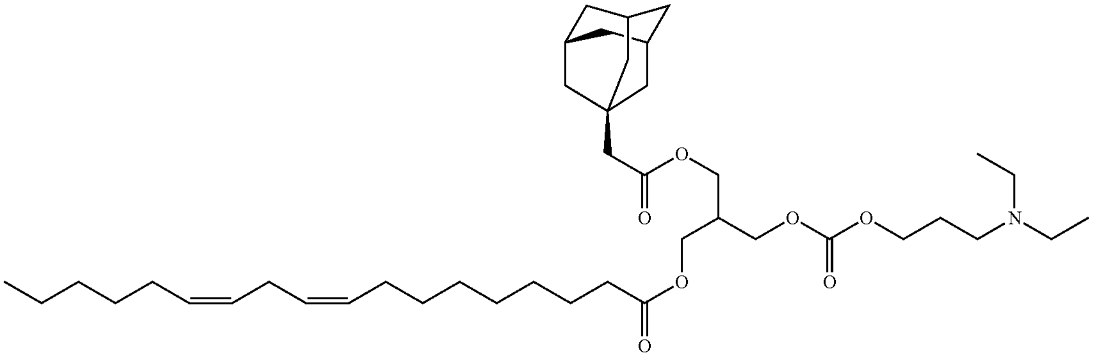

3-[(1-Adamantanyl)acetoxy]-2-{[3-(diethylamino)propoxycarbonyloxy]methyl}propyl (9Z,12Z)-9,12-octadecadienoate or an LNP containing the ionizable lipid of Formula II.

Another embodiment provides an ionizable lipid according to Formula I, wherein $R_1$ is tail L, and $R_2$ is compound (1) or an LNP containing said ionizable lipid.

Still another embodiment provides an ionizable lipid according to Formula I, wherein $R_1$ is tail L, and $R_2$ is compound (2) or an LNP containing said ionizable lipid.

One embodiment provides an ionizable lipid according to the following structure:

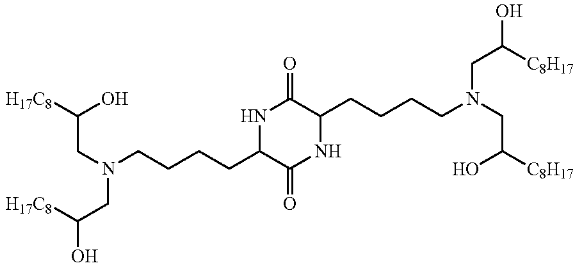

or an LNP containing said ionizable lipid.

One embodiment provides an ionizable lipid according to the following structure:

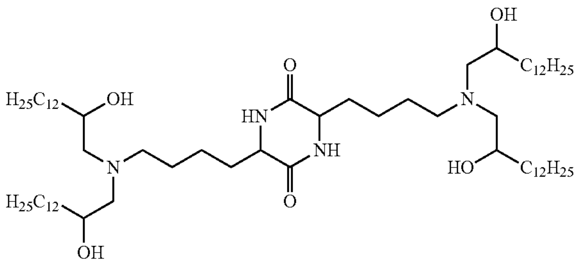

or an LNP containing said ionizable lipid.

One embodiment provides an ionizable lipid according to the following structure:

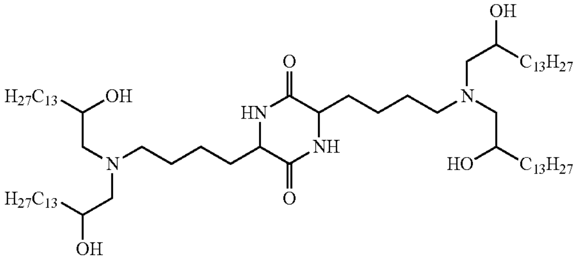

or an LNP containing said ionizable lipid.

One embodiment provides an ionizable lipid according to the following structure:

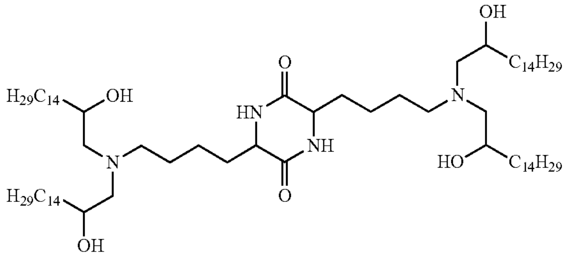

or an LNP containing said ionizable lipid.

One embodiment provides an ionizable lipid according to the following structure:

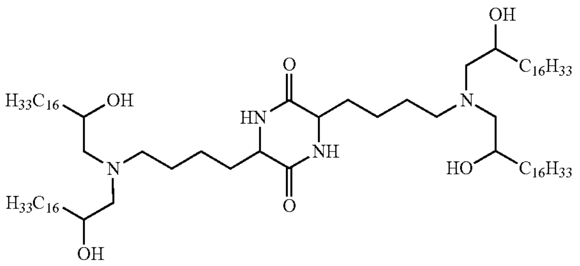

or an LNP containing said ionizable lipid.

One embodiment provides an ionizable lipid according to the following structure:

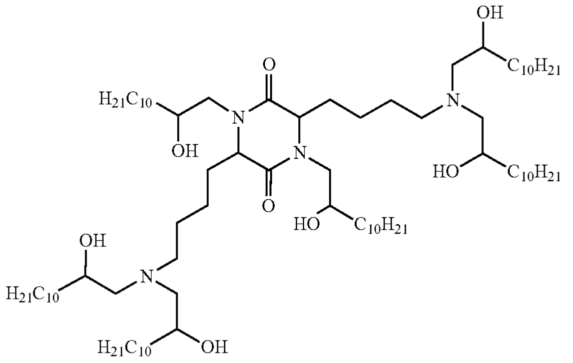

or an LNP containing said ionizable lipid.

One embodiment provides an ionizable lipid according to the following structure:

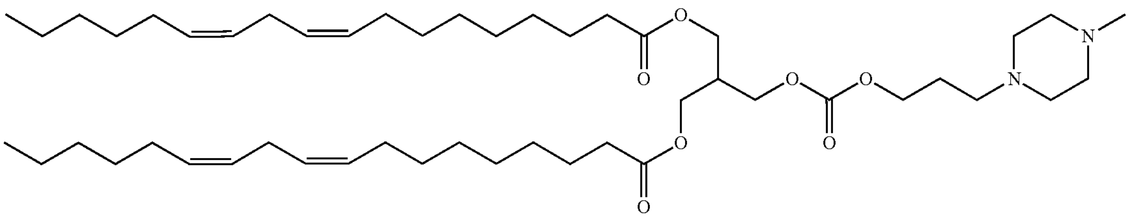 [SMILES: CCCCC/C=C\C/C=C\CCCCCCCC(=O)OCC(COC(=O)CCCCCCC/C=C\C/C=C\CCCCC)COC(=O)OCCCN1CCN(C)CC1]

or an LNP containing said ionizable lipid.

One embodiment an ionizable lipid according to the following structure:

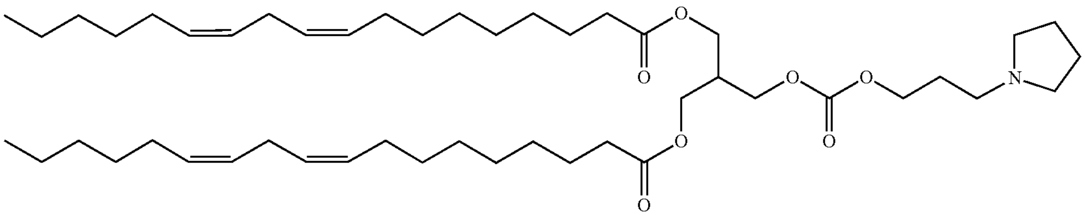 [SMILES: CCCCC/C=C\C/C=C\CCCCCCCC(=O)OCC(COC(=O)CCCCCCC/C=C\C/C=C\CCCCC)COC(=O)OCCCN1CCCC1]

or an LNP containing said ionizable lipid.

One embodiment provides an ionizable lipid according to the following structure:

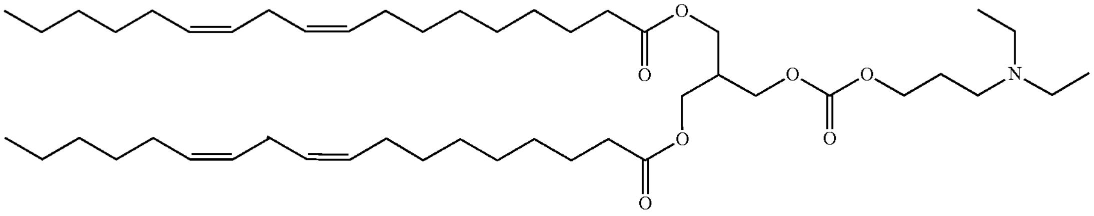 [SMILES: CCCCC/C=C\C/C=C\CCCCCCCC(=O)OCC(COC(=O)CCCCCCC/C=C\C(C)/C=C\CCCCC)COC(=O)OCCCN(CC)CC]

or an LNP containing said ionizable lipid.

One embodiment provides an ionizable lipid according to the following structure:

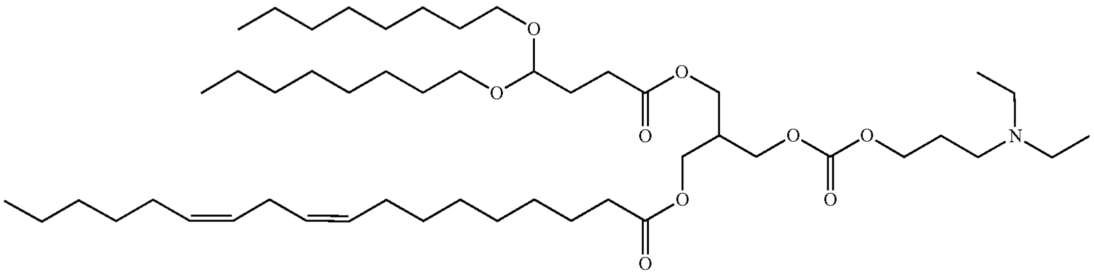 [SMILES: CCCCC/C=C\C/C=C\CCCCCCCC(=O)OCC(COC(=O)CCC(OCCCCCCCC)OCCCCCCCC)COC(=O)OCCCN(CC)CC]

or an LNP containing said ionizable lipid.

One embodiment provides an ionizable lipid according to the following structure:

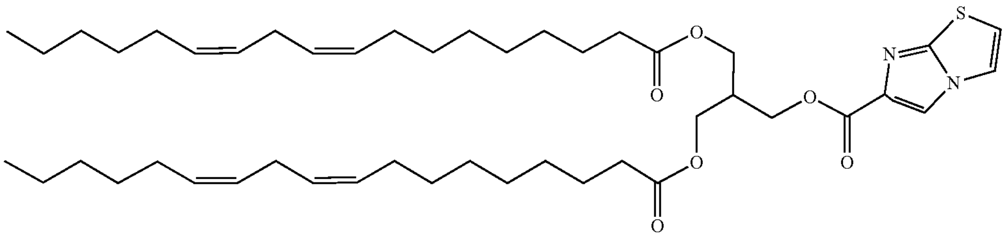 [SMILES: CCCCC/C=C\C/C=C\CCCCCCCC(=O)OCC(COC(=O)CCCCCCC/C=C\C/C=C\CCCCC)COC(=O)C1C=CN2C=CSC2=N1]

or an LNP containing said ionizable lipid.

One embodiment provides an ionizable lipid according to the following structure:

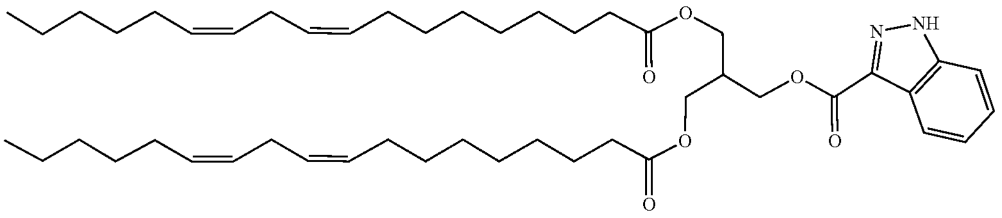 [SMILES: CCCCC/C=C\C/C=C\CCCCCCCC(=O)OCC(COC(=O)CCCCCCC/C=C\C/C=C\CCCCC)COC(=O)c1n[nH]c2ccccc12]

or an LNP containing said ionizable lipid.

One embodiment provides an ionizable lipid according to the following structure:

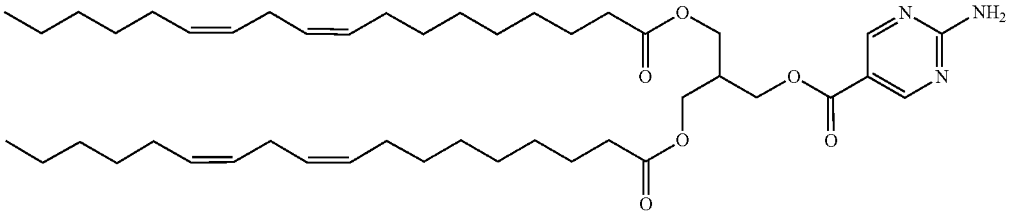 [SMILES: CCCCC/C=C\C/C=C\CCCCCCCC(=O)OCC(COC(=O)CCCCCCC/C=C\C/C=C\CCCCC)COC(=O)c1cnc(N)nc1]

or an LNP containing said ionizable lipid.

One embodiment provides an ionizable lipid according to the following structure:

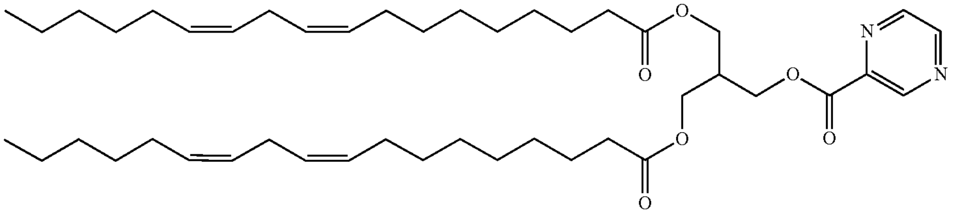 [SMILES: CCCCC/C=C\C/C=C\CCCCCCCC(=O)OCC(COC(=O)CCCCCCC/C=C\C/C=C\CCCCC)COC(=O)c1cnccn1]

or an LNP containing said ionizable lipid.

One embodiment provides an ionizable lipid according to the following structure:

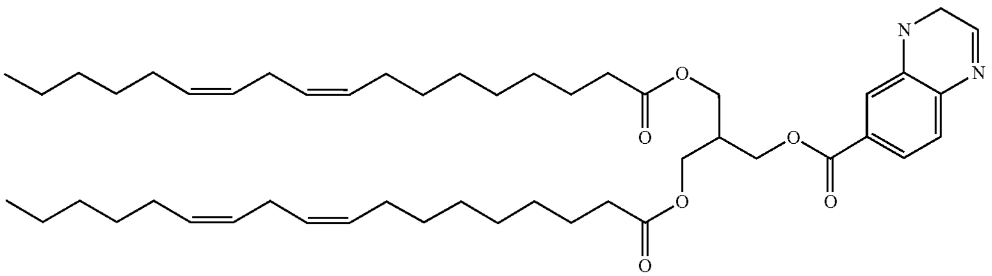 [SMILES: CCCCC/C=C\C/C=C\CCCCCCCC(=O)OCC(COC(=O)CCCCCCC/C=C\C/C=C\CCCCC)COC(=O)c1ccc2c(c1)NCC=N2]

or an LNP containing said ionizable lipid.

One embodiment provides an ionizable lipid according to the following structure:

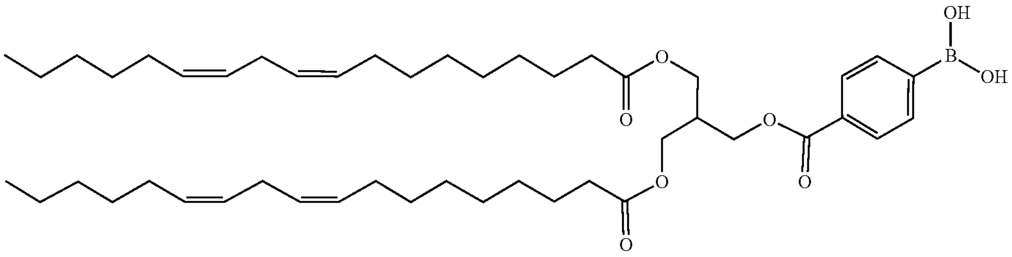 [SMILES: CCCCC/C=C\C/C=C\CCCCCCCC(=O)OCC(COC(=O)CCCCCCC/C=C\C/C=C\CCCCC)COC(=O)c1ccc(B(O)O)cc1]

or an LNP containing said ionizable lipid.

One embodiment provides an ionizable lipid according to the following structure:

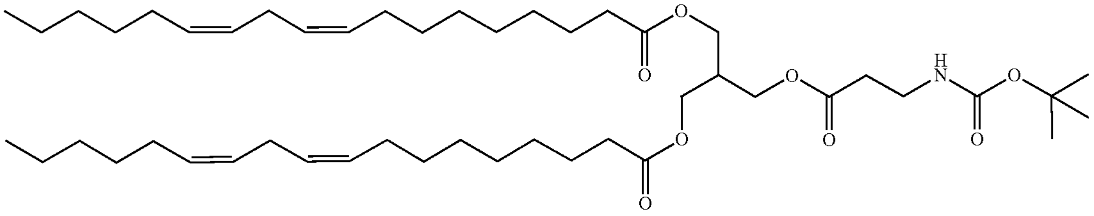 [SMILES: CCCCC/C=C\C/C=C\CCCCCCCC(=O)OCC(COC(=O)CCCCCCC/C=C\C/C=C\CCCCC)COC(=O)CCNC(=O)OC(C)(C)C]

or an LNP containing said ionizable lipid.

One embodiment provides an ionizable lipid according to the following structure:

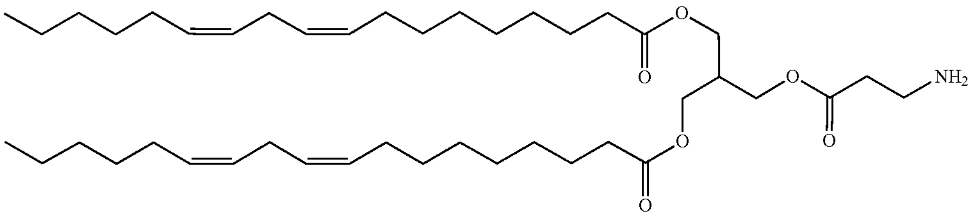 [SMILES: CCCCC/C=C\C/C=C\CCCCCCCC(=O)OCC(COC(=O)CCN)COC(=O)CCCCCCC/C=C\C/C=C\CCCCC]

or an LNP containing said ionizable lipid.

One embodiment provides an ionizable lipid according to the following structure:

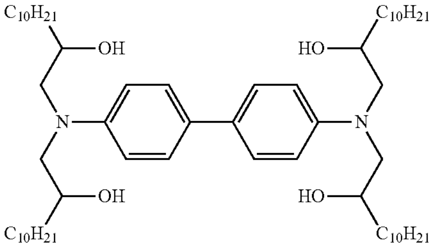

or an LNP containing said ionizable lipid.

One embodiment provides an ionizable lipid according to the following structure:

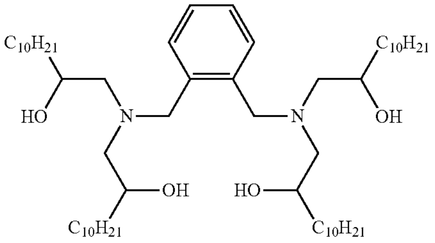

or an LNP containing said ionizable lipid.

One embodiment provides an ionizable lipid according to the following structure:

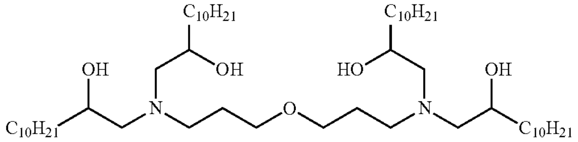

or an LNP containing said ionizable lipid.

One embodiment provides an ionizable lipid according to the following structure:

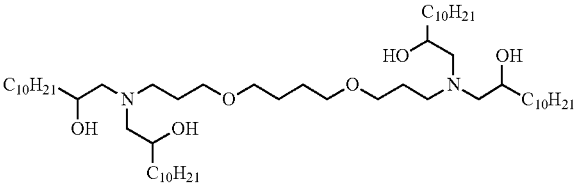

or an LNP containing said ionizable lipid.

One embodiment provides an ionizable lipid according to the following structure:

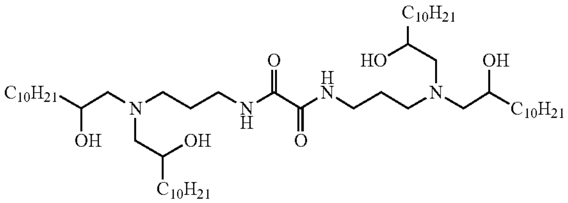

or an LNP containing said ionizable lipid.

One embodiment provides an ionizable lipid according to the following structure:

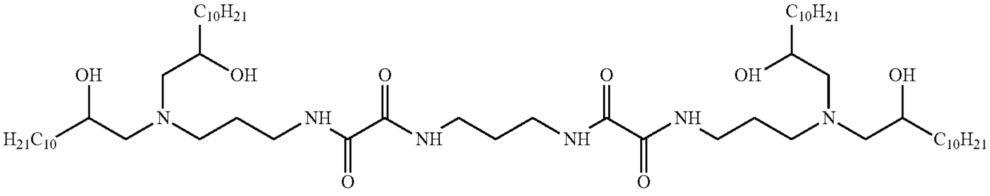

or an LNP containing said ionizable lipid.

One embodiment provides an ionizable lipid according to the following structure:

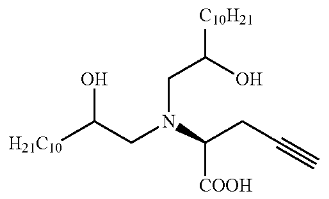

or an LNP containing said ionizable lipid.

One embodiment provides an ionizable lipid according to the following structure:

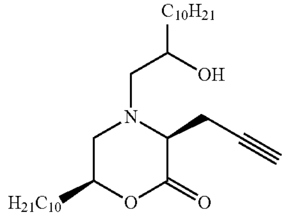

or an LNP containing said ionizable lipid.

One embodiment provides an ionizable lipid according to the following structure:

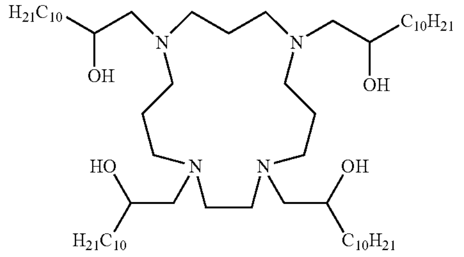

or an LNP containing said ionizable lipid.

One embodiment provides an ionizable lipid according to the following structure:

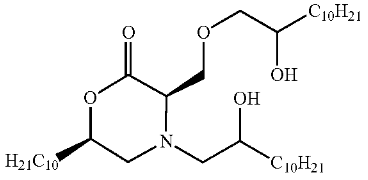

or an LNP containing said ionizable lipid.

One embodiment provides an ionizable lipid according to the following structure:

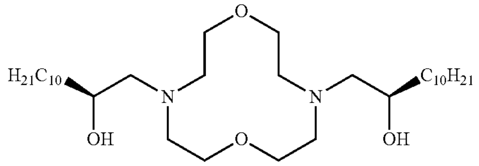

or an LNP containing said ionizable lipid.

One embodiment provides an ionizable lipid according to the following structure:

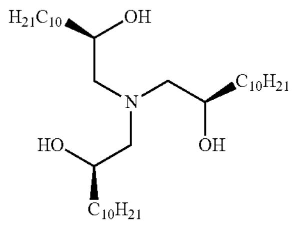

or an LNP containing said ionizable lipid.

One embodiment provides an ionizable lipid according to the following structure:

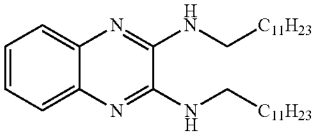

or an LNP containing said ionizable lipid.

One embodiment an ionizable lipid according to the following structure:

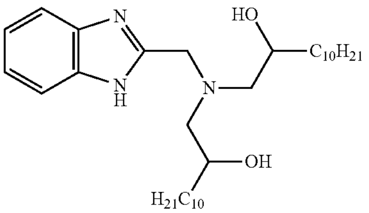

or an LNP containing said ionizable lipid.

One embodiment provides an ionizable lipid according to the following structure:

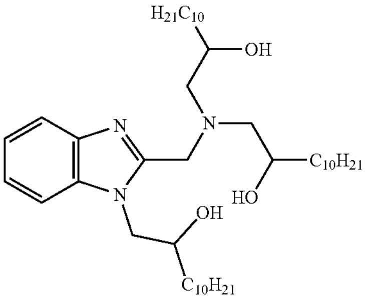

or an LNP containing said ionizable lipid.

One embodiment provides an ionizable lipid according to the following structure:

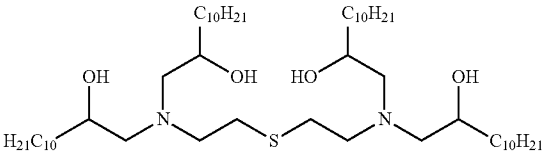

or an LNP containing said ionizable lipid.

One embodiment provides an ionizable lipid according to the following structure:

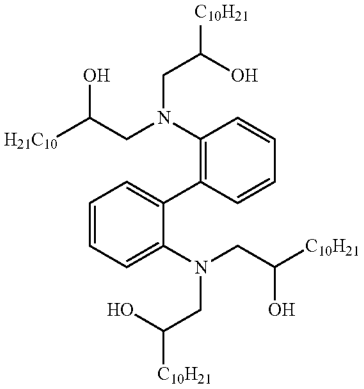

or an LNP containing said ionizable lipid.

One embodiment provides an ionizable lipid according to the following structure:

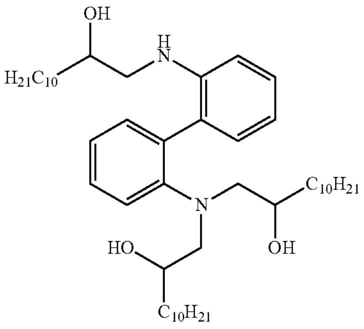

or an LNP containing said ionizable lipid.

One embodiment provides an ionizable lipid according to the following structure:

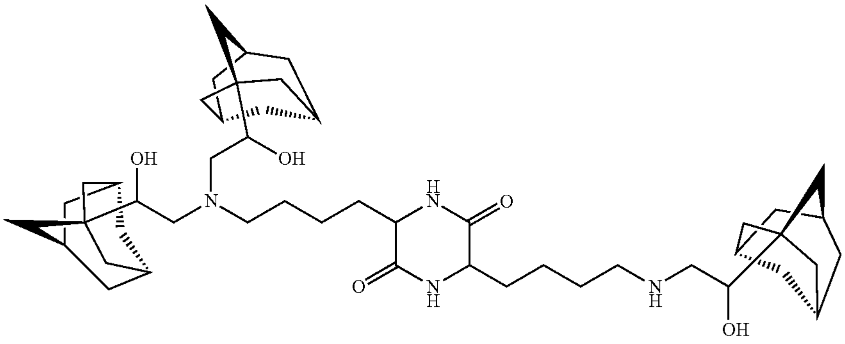 [SMILES: O=C1NC(CCCCN(CC(O)[C@]23C[C@H]4C[C@@H](C[C@H](C4)C2)C3)CC(O)[C@]23C[C@H]4C[C@@H](C[C@H](C4)C2)C3)C(=O)NC1CCCCNCC(O)[C@]12C[C@H]3C[C@@H](C[C@H](C3)C1)C2]

or an LNP containing said ionizable lipid.

One embodiment provides an ionizable lipid according to the following structure:

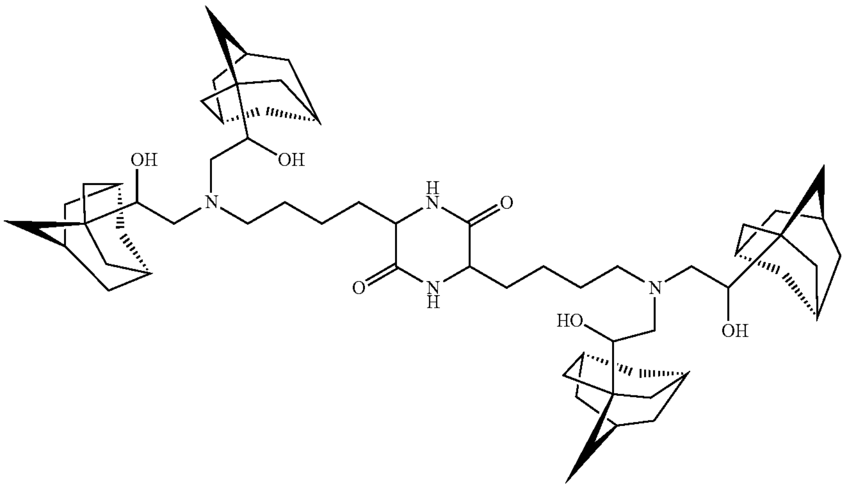 [SMILES: O=C1NC(CCCCN(CC(O)[C@]23C[C@H]4C[C@@H](C[C@H](C4)C2)C3)CC(O)[C@]23C[C@H]4C[C@@H](C[C@H](C4)C2)C3)C(=O)NC1CCCCN(CC(O)[C@]12C[C@H]3C[C@@H](C[C@H](C3)C1)C2)CC(O)[C@]12C[C@H]3C[C@@H](C[C@H](C3)C1)C2]

or an LNP containing said ionizable lipid.

One embodiment provides an ionizable lipid according to the following structure:

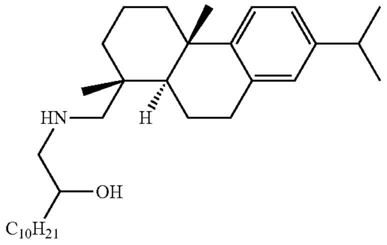

or an LNP containing said ionizable lipid.

One embodiment provides an ionizable lipid according to the following structure:

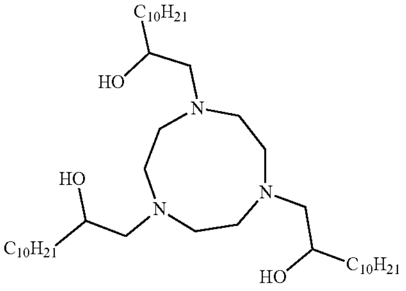

or an LNP containing said ionizable lipid.

One embodiment provides an ionizable lipid according to the following structure:

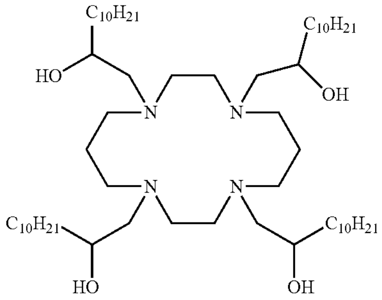

or an LNP containing said ionizable lipid.

One embodiment provides an ionizable lipid according to the following structure:

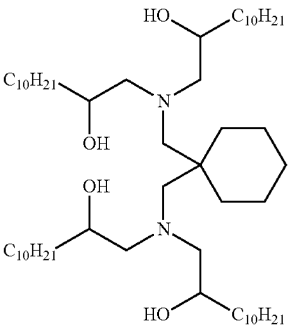

or an LNP containing said ionizable lipid.

One embodiment provides an ionizable lipid according to the following structure:

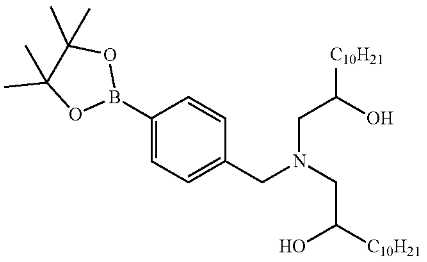

or an LNP containing said ionizable lipid.

One embodiment provides an ionizable lipid according to the following structure:

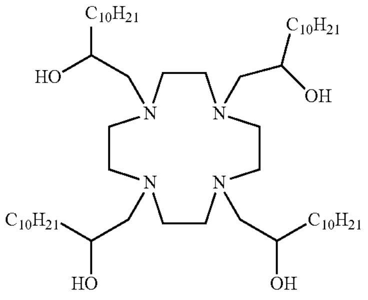

or an LNP containing said ionizable lipid.

One embodiment provides an ionizable lipid according to the following structure:

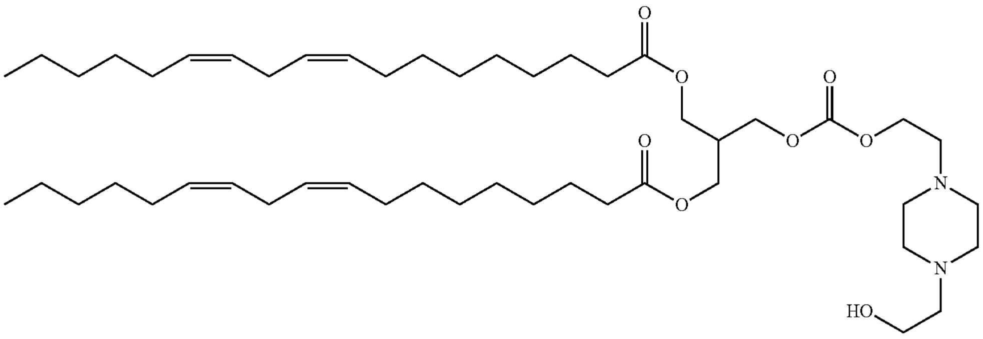 [SMILES: CCCCC/C=C\C/C=C\CCCCCCCC(=O)OCC(COC(=O)CCCCCCC/C=C\C/C=C\CCCCC)COC(=O)OCCN1CCN(CCO)CC1]

or an LNP containing said ionizable lipid.

One embodiment provides an ionizable lipid according to the following structure:

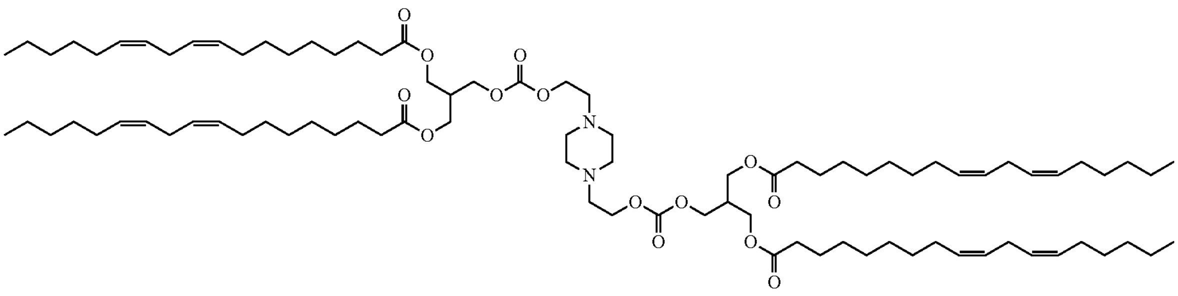 [SMILES: CCCCC/C=C\C/C=C\CCCCCCCC(=O)OCC(COC(=O)CCCCCCC/C=C\C/C=C\CCCCC)COC(=O)OCCN1CCN(CCOC(=O)OCC(COC(=O)CCCCCCC/C=C\C/C=C\CCCCC)COC(=O)CCCCCCC/C=C\C/C=C\CCCCC)CC1]

or an LNP containing said ionizable lipid.

One embodiment provides an ionizable lipid according to the following structure:

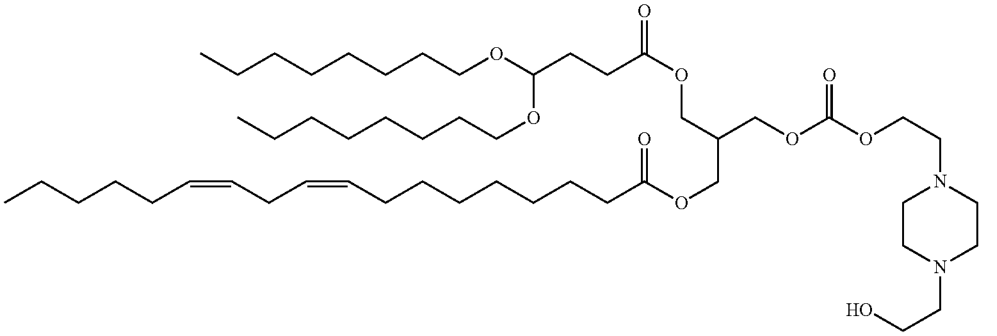 [SMILES: CCCCC/C=C\C/C=C\CCCCCCCC(=O)OCC(COC(=O)CCC(OCCCCCCCC)OCCCCCCCC)COC(=O)OCCN1CCN(CCO)CC1]

or an LNP containing said ionizable lipid.

One embodiment provides an ionizable lipid according to the following structure:

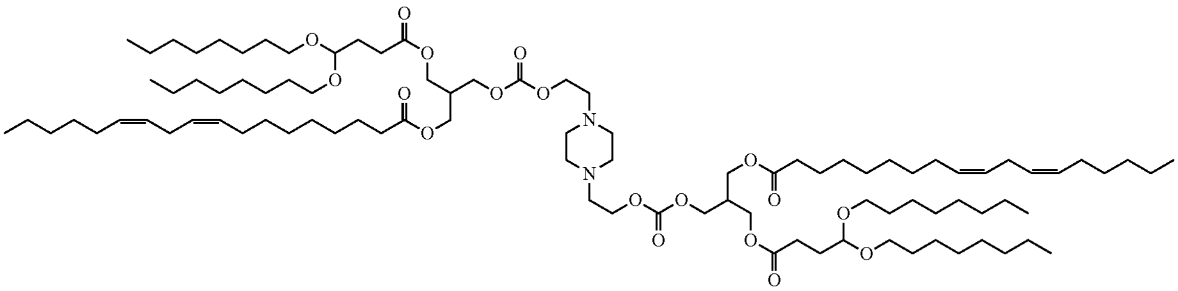 [SMILES: CCCCC/C=C\C/C=C\CCCCCCCC(=O)OCC(COC(=O)CCC(OCCCCCCCC)OCCCCCCCC)COC(=O)OCCN1CCN(CCOC(=O)OCC(COC(=O)CCCCCCC/C=C\C/C=C\CCCCC)COC(=O)CCC(OCCCCCCCC)OCCCCCCCC)CC1]

or an LNP containing said ionizable lipid.

One embodiment provides an ionizable lipid according to the following structure:

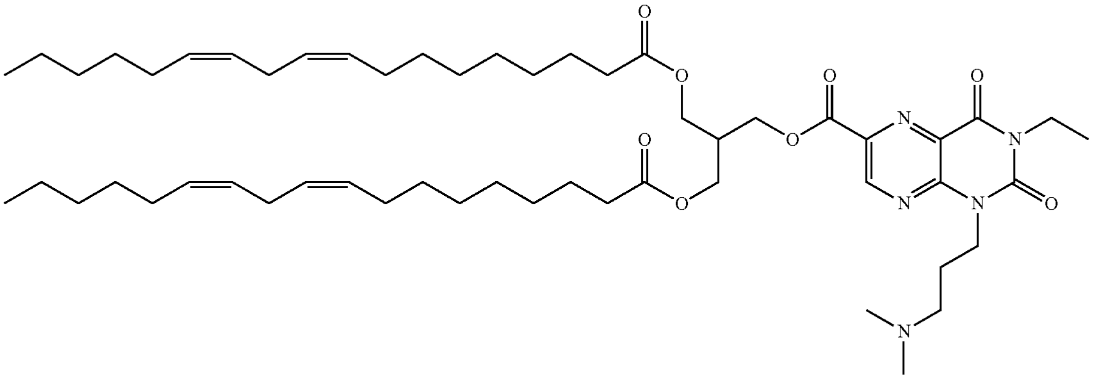 [SMILES: CCCCC/C=C\C/C=C\CCCCCCCC(=O)OCC(COC(=O)CCCCCCC/C=C\C/C=C\CCCCC)COC(=O)c1cnc2c(n1)c(=O)n(CC)c(=O)n2CCCN(C)C]

or an LNP containing said ionizable lipid.

One embodiment provides an ionizable lipid according to the following structure:

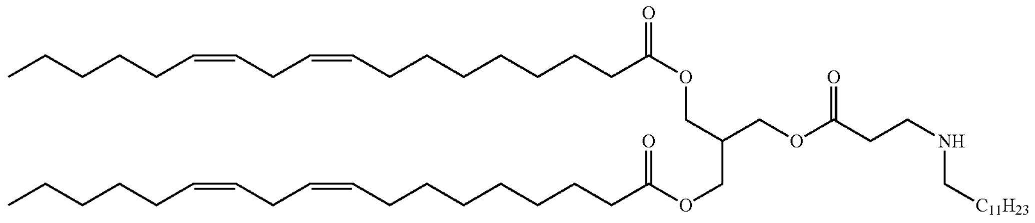

or an LNP containing said ionizable lipid.

One embodiment provides an ionizable lipid according to the following structure:

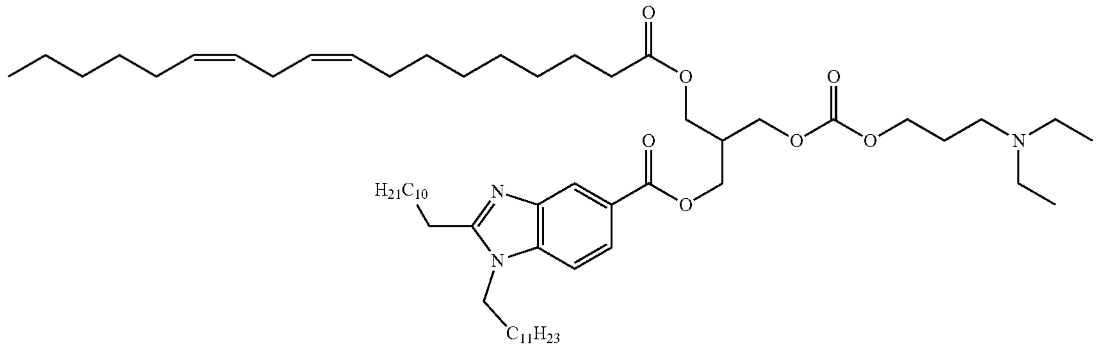

or an LNP containing said ionizable lipid.

One embodiment provides an ionizable lipid according to the following structure:

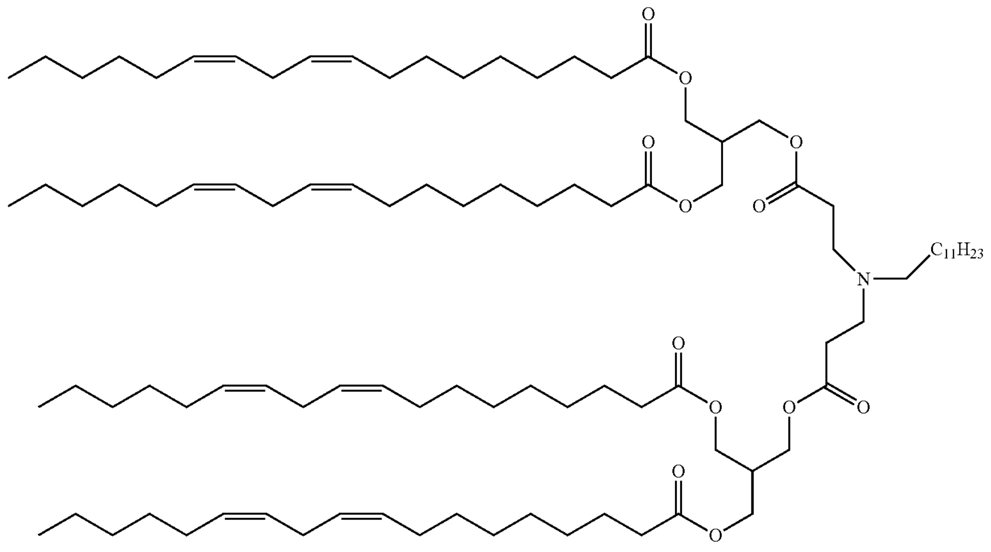

or an LNP containing said ionizable lipid.

One embodiment provides an ionizable lipid according to the following structure:

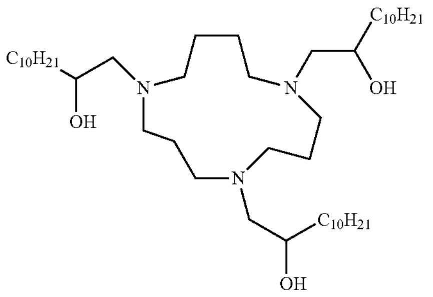

or an LNP containing said ionizable lipid.

One embodiment provides an ionizable lipid according to the following structure:

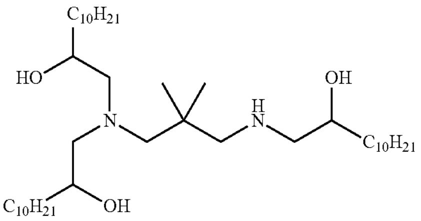

or an LNP containing said ionizable lipid.

One embodiment provides an ionizable lipid according to the following structure:

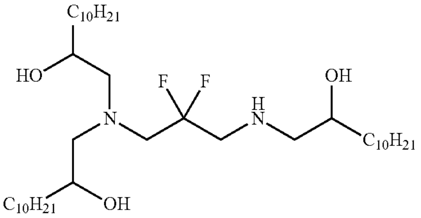

or an LNP containing said ionizable lipid.

One embodiment provides an ionizable lipid according to the following structure:

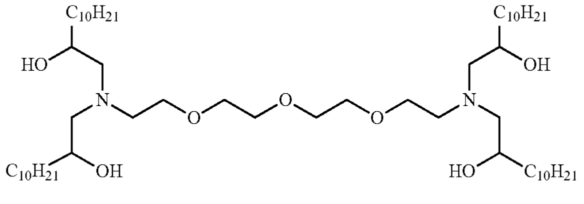

or an LNP containing said ionizable lipid.

One embodiment provides an ionizable lipid according to the following structure:

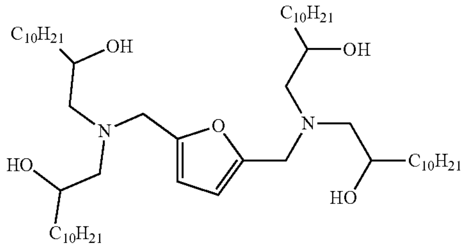

or an LNP containing said ionizable lipid.

One embodiment provides an ionizable lipid according to the following structure:

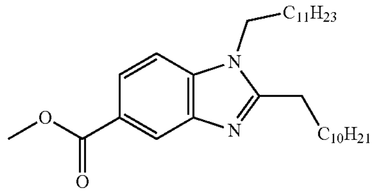

or an LNP containing said ionizable lipid.

One embodiment provides an ionizable lipid according to the following structure:

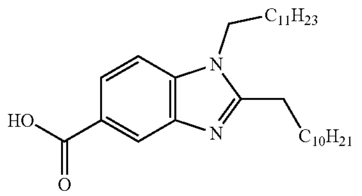

or an LNP containing said ionizable lipid.

One embodiment provides an ionizable lipid according to the following structure:

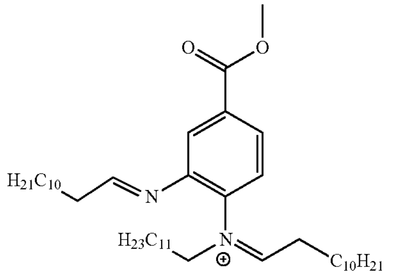

or an LNP containing said ionizable lipid.

B. Sterols

In some embodiments, the disclosed lipid nanoparticles include one or more sterols. In one embodiment, the sterol is cholesterol, or a variant or derivative thereof. In some embodiments, the cholesterol is modified, for example oxidized. Unmodified cholesterol can be acted upon by enzymes to form variants that are side-chain or ring oxidized. The cholesterol can be oxidized on the beta-ring structure or on the hydrocarbon tail structure. Exemplary cholesterols that are considered for use in the disclosed lipid nanoparticles include but are not limited to 25-hydroxycholesterol (25-OH), 20α-hydroxycholesterol (20α-OH), 27-hydroxycholesterol, 6-keto-5α-hydroxycholesterol, 7-ketocholesterol, 7β-hydroxycholesterol, 7α-hydroxycholesterol, 7β-25-dihydroxycholesterol, beta-sitosterol, stigmasterol or combinations thereof. In one embodiment, side-chain oxidized cholesterol can enhance cargo delivery relative to other cholesterol variants. In one embodiment, the cholesterol is an unmodified cholesterol.

C. PEG-Lipids

In some embodiments, the disclosed nanoparticle compositions also include one or more PEG or PEG-modified lipids. Such species may be alternately referred to as PEGylated lipids or PEG-lipids. Inclusion of a PEGylating lipid can be used to enhance lipid nanoparticle colloidal stability in vitro and circulation time in vivo. In some embodiments, the PEGylation is reversible in that the PEG moiety is gradually released in blood circulation. Exemplary PEG-lipids include but are not limited to PEG conjugated to saturated or unsaturated alkyl chains having a length of $C_6$-$C_{20}$. PEG-modified phosphatidylethanolamines, PEG-modified phosphatidic acids, PEG-modified ceramides (PEG-CER), PEG-modified dialkylamines, PEG-modified diacylglycerols (PEG-DAG), PEG-modified dialkylglycerols, and mixtures thereof. For example, a PEG lipid may be PEG-c-DOMG, PEG-DMG, PEG-DLPE, PEG-DMPE, PEG-DPPE, PEG-DSG or a PEG-DSPE lipid.

In a one embodiment, the PEG lipid is DMPE-$PEG_{2000}$ or DSPE-$PEG_{2000}$.

D. Phospholipids

The phospholipid component of the nanoparticle may include one or more phospholipids, such as one or more (poly)unsaturated lipids. The phospholipids may assemble into one or more lipid bilayers. In some embodiments, the phospholipids may include a phospholipid moiety and one or more fatty acid moieties.

In some embodiments, the phospholipid moiety includes but is not limited to phosphatidyl choline, phosphatidyl ethanolamine, phosphatidyl glycerol, phosphatidyl serine, phosphatidic acid, 2-lysophosphatidyl choline, and sphingomyelin. In some embodiments, the fatty acid moiety includes but is not limited to lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. Nonnatural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Exemplary phospholipids include but are not limited to 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoy 1-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidy ethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE). In a preferred embodiment, the phospholipid is DSPC.

E. Cargo

In one embodiment, the disclosed lipid nanoparticle compositions include a therapeutic or prophylactic agent to a subject. In some embodiments, the therapeutic or prophylactic agent is encapsulated by the lipid nanoparticle. In one embodiment, the lipid nanoparticles are loaded with one or more nucleic acids.

Representative nucleic acids include but are not limited to deoxyribonucleic acid (DNA), ribonucleic acid (RNA) RNA, DNA, single-stranded RNA, single-stranded DNA, double-stranded RNA, double stranded DNA, triple-stranded DNA, siRNA, shRNA, sgRNA, mRNA, miRNA, and antisense DNA.

CRISPR (Clustered Regularly Interspaced Short Palindromic Repeats) based gene editing requires two components: a guide-RNA and a CRISPR-associated endonuclease protein (Cas). The guide RNA directs the Cas nuclease to the specific target DNA sequence. Cas then creates a double-strand break in the DNA at that site. In one embodiment, the disclosed lipid nanoparticles can be used to carry the components required for CRISPR-based gene editing. In one lipid nanoparticle, the nucleic acid cargo is a guide-RNA. In such an embodiment, a second lipid nanoparticle can contain nucleic acid cargo that encodes an RNA-guided endonuclease. The two lipid nanoparticles can be administered together. Exemplary RNA-guided endonucleases include but are not limited to Cas9, CasX, CasY, Cas13, or Cpf1.

In one embodiment, the cargo is siRNA. Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82.

In one embodiment, the lipid nanoparticle contains less than 1.0 mg/kg inhibitory nucleic acid. The nanoparticle can contain 1.0, 0.9, 0.8, 0.7, 0.6, or 0.5 mg/kg inhibitory nucleic acid. In another embodiment, the lipid nanoparticle contains 0.5 mg/kg inhibitory nucleic acid. This is an advantage over current technology in which nanoparticles require high doses of nucleic acid (>1 mg/kg) to achieve gene silencing, doses of which are not approve for human delivery. The disclosed technology can achieve gene silencing using 0.5 mg/kg inhibitory nucleic acid in a lipid nanoparticle that does not include targeting ligands.

In some embodiments, the nucleic acids, including but not limited to oligonucleotides, are modified or include one more modified nucleotides to increase stability, half-life, and nuclease sensitivity. To limit nuclease sensitivity, the native phosphodiester oligodeoxyribonucleotide, native phosphodiester oligoribonucleotide, ribonucleotide polymers, and deoxyribonucleotide polymers can include one more different modifications. Exemplary modifications, include but are not limited to phosphorothioate (PS) bonds, 2"-O Methyl (2'OMe), 2' Fluor bases, inverted dT and ddT, phosphorylation of the 3' end of oligonucleotides, locked nucleic acids, and including a phosphoramidite C3 Spacer.

The phosphorothioate bond substitutes a sulfur atom for a non-bridging oxygen in the phosphate backbone of an oligonucleotide. Approximately 50% of the time (due to the 2 resulting stereoisomers that can form), PS modification renders the internucleotide linkage more resistant to nuclease degradation. In some embodiments, the nucleic acids include one or more PS bonds, for example at least 3 PS bonds at the 5' and 3' oligonucleotide ends to inhibit exonuclease degradation. Some nucleic acid include PS bonds throughout the entire oligonucleotide to help reduce attack by endonucleases as well.

A naturally occurring post-transcriptional modification of RNA, 2'OMe is found in tRNA and other small RNAs. In some embodiments, the nucleic acids or oligonucleotides are directly synthesized to contain 2'OMe. This modification increases the Tm of RNA:RNA duplexes, but results in only small changes in RNA:DNA stability. It prevents attack by single-stranded endonucleases, but not exonuclease digestion. In some embodiment, these nucleic acids or oligonucleotides are also end blocked. DNA oligonucleotides that include this modification are typically 5- to 10-fold less susceptible to DNases than unmodified DNA. The 2'OMe modification is commonly used in antisense oligonucleotides as a means to increase stability and binding affinity to target transcripts.

2'-fluoro bases have a fluorine-modified ribose which increases binding affinity (Tm) and also confers some relative nuclease resistance compared to native RNA. In some embodiments, the nucleic acids or oligonucleotides include 2' fluoro bases in conjunction with PS-modified bonds.

Inverted dT can be incorporated at the 3' end of an oligonucleotide, leading to a 3'-3' linkage that will inhibit degradation by 3' exonucleases and extension by DNA polymerases. In addition, placing an inverted, 2',3' dideoxy-dT base (5' Inverted ddT) at the 5' end of an oligonucleotide prevents spurious ligations and may protect against some forms of enzymatic degradation.

Some embodiments provide nucleic acids or oligonucleotides that include a phosphoramidite C3 Spacer. The phosphoramidite C3 Spacer can be incorporated internally, or at either end of an oligo to introduce a long hydrophilic spacer arm for the attachment of fluorophores or other pendent groups. The C3 spacer also can be used to inhibit degradation by 3' exonucleases.

In some embodiments, the nucleic acids or oligonucleotides include locked nucleic acids. Locked nucleic acids include modified RNA nucleotides in which the 2'-O and 4'-C atoms of the ribose are joined through a methylene bridge. This additional bridge limits the flexibility normally associated with the ring, essentially locking the structure into a rigid conformation.

LNAs can be inserted into both RNA and DNA oligonucleotides.

Other types of cargo that can be delivered via the disclosed nanoparticles include but are not limited to chemotherapeutic agents, cytotoxic agents, radioactive ions, small molecules, proteins, polynucleotides, and nucleic acids.

Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

F. Exemplary Lipid Nanoparticle Formulations

In one embodiment, the lipid nanoparticle formulation includes about 30 mol % to about 70 mol % conformationally constrained ionizable lipid, about 5 mol % to about 25 mol % phospholipid, about 25 mol % to about 45 mol % cholesterol, and about 0 mol % to about 5 mol % PEG-lipid. In another embodiment, the lipid nanoparticle formulation include about 35 mol % conformationally constrained ionizable lipid, about 16 mol % phospholipid, about 46.5 mol % cholesterol, and about 2.5 mol % PEG-lipid. In another embodiment, the lipid nanoparticle formulation include about 50 mol % conformationally constrained ionizable lipid, about 10 mol % phospholipid, about 38.5 mol % cholesterol, and about 1.5 mol % PEG-lipid.

One embodiment provides a lipid nanoparticle formulation including about 33 mol % to about 36 mol % conformationally constrained ionizable lipid with an adamantane tail, about 15 mol % to about 17 mol % 1-2-distearoyl-sn-glycero-3-phosphocholine, about 2 mol % to about 3 mol % $C_{14}PEG_{2000}$, and about 45 mol % to about 47 mol % cholesterol, based on the total moles of these four ingredients.

Another embodiment provides a lipid nanoparticle formulation including 35 mol % conformationally constrained ionizable lipid with an adamantane tail, 16 mol % 1-2-distearoyl-sn-glycero-3-phosphocholine, and 2.5 mol % $C_{14}PEG_{2000}$, 46 mol % cholesterol, based on the total moles of these four ingredients.

Another embodiment provides a lipid nanoparticle formulation in which the mass ratio of (ionizable lipid, cholesterol, lipid-PEG, and phospholipid):siRNA is between about 2:1 and 20:1.

In yet another embodiment the lipid nanoparticle formulation includes 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and an inhibitory nucleic acid.

One embodiment provides a lipid nanoparticles composition containing 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and sgRNA specific for a gene. Another embodiment provides a lipid nanoparticle including 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and mRNA encoding an RNA guided DNA endonuclease.

G. Pharmaceutical Compositions

Pharmaceutical compositions including the disclosed lipid nanoparticles are provided. The lipid nanoparticle compositions can be formulated in whole or in part as pharmaceutical compositions. Pharmaceutical compositions may include one or more nanoparticle compositions. For example, a pharmaceutical composition may include one or more nanoparticle compositions including one or more different therapeutic and/or prophylactics including but not limited to one or more nucleic acids of different types or encode different agents. In some embodiments the pharmaceutical compositions include one or more pharmaceutically acceptable excipients or accessory ingredients including but not limited to a pharmaceutically acceptable carrier.

Pharmaceutical compositions containing the nanoparticles can be formulated for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the nanoparticle compositions disclosed herein are administered to a subject in a therapeutically effective amount. As used herein the term “effective amount” or “therapeutically effective amount” means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed nanoparticles, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed nanoparticles, generally dosage levels of 0.001 mg to 5 mg of nucleic acid per kg of body weight daily are administered to mammals. More specifically, a preferential dose for the disclosed nanoparticles is 0.01 mg/kg to 0.25 mg/kg. For the disclosed nanoparticles, generally dosage levels of 0.2 mg to 100 mg of the four components (ionizable lipid, cholesterol, PEG-lipid, and phospholipid)/kg of body weight are administered to mammals. More specifically, a preferential dose of the disclosed nanoparticles is 0.05 mg/kg to 0.5 mg/kg of the four components/kg of body weight.

In certain embodiments, the lipid nanoparticle composition is administered locally, for example by injection directly into a site to be treated. Typically, the injection causes an increased localized concentration of the lipid nanoparticle composition which is greater than that which can be achieved by systemic administration. The lipid nanoparticle compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, the nanoparticle compositions disclosed herein, including those containing lipid nanoparticles, are administered in an aqueous solution, by parenteral injection. The formulation may also be in the form of a suspension or emulsion. In general, pharmaceutical compositions are provided including effective amounts of a lipid nanoparticle, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Controlled Delivery Polymeric Matrices

The lipid nanoparticles disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of lipid nanoparticles, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases, linear release may be most useful, although in others a pulse release or “bulk release” may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl. Polymer Sci., 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Manufacturing Lipid Nanoparticles

Methods of manufacturing lipid nanoparticles are known in the art. In one embodiment, the disclosed lipid nanoparticles are manufactured using microfluidics. For exemplary methods of using microfluidics to form lipid nanoparticles, see Leung, A. K. K, et al., *J Phys Chem,* 116:18440-18450 (2012), Chen, D., et al., *J Am Chem Soc,* 134:6947-6951 (2012), and Belliveau, N. M., et al., *Molecular Therapy-Nucleic Acids,* 1: e37 (2012). Briefly, the cargo, such as an oligonucleotide or siRNA, is prepared in one buffer. The other lipid nanoparticle components (ionizable lipid, PEG-lipid, cholesterol, and DSPC) are prepared in another buffer. A syringe pump introduces the two solutions into a microfluidic device. The two solutions come into contact within the microfluidic device to form lipid nanoparticles encapsulating the cargo.

Methods of screening the disclosed lipid nanoparticles are discussed in International Patent Application No. PCT/US/2018/058171, which is incorporated by reference in its entirety. The screening methods characterizes vehicle delivery formulations to identify formulations with a desired tropism and that deliver functional cargo to the cytoplasm of specific cells. The screening method uses a reporter that has a functionality that can be detected when delivered to the cell. Detecting the function of the reporter in the cell indicates that the formulation of the delivery vehicle will deliver functional cargo to the cell. A chemical composition identifier is included in each different delivery vehicle formulation to keep track of the chemical composition specific for each different delivery vehicle formulation. In one embodiment, the chemical composition identifier is a nucleic acid barcode. The sequence of the nucleic acid bar code is paired to the chemical components used to formulate the delivery vehicle in which it is loaded so that when the nucleic acid bar code is sequenced, the chemical composition of the delivery vehicle that delivered the barcode is identified. Representative reporters include, but are not limited to siRNA, mRNA, nuclease protein, nuclease mRNA, small molecules, epigenetic modifiers, and phenotypic modifiers.

IV. Methods of Use

Methods of using the disclosed lipid nanoparticles to deliver cargo, for example nucleic acids, to specific cells or organs are disclosed herein. In some embodiments, the nanoparticles deliver therapeutic or prophylactic agents to specific cells or organs in a subject in need thereof in the absence of a targeting ligand. In another embodiment, the disclosed lipid nanoparticles are useful to treat or prevent diseases in a subject in need thereof.

In some embodiments, the disclosed nanoparticles are delivered directly to the subject. In other embodiments, the lipid nanoparticles are contacted with cells ex vivo, and the treated cells are administered to the subject. The cells can be autologous cells, for example immune cells including but not limited to T cells or cells that differentiate into T cells. In some embodiments, the disclosed lipid nanoparticles may be used as vehicles for adoptive cell transfer.

A. Methods of Delivering Cargo to Cells

Methods of delivering a therapeutic and/or prophylactic nucleic acids to a subject in need thereof are provided herein.

In some embodiments, the disclosed lipid nanoparticle composition targets a particular type or class of cells (e.g., cells of a particular organ or system thereof). For example, a nanoparticle composition including a therapeutic and/or prophylactic of interest may be specifically delivered to immune cells in the subject. Exemplary immune cells include but are not limited to CD8+, CD4+, or CD8+CD4+ cells. In other embodiments, the lipid nanoparticles can be formulated to be delivered in the absence of a targeting ligand to a mammalian liver immune cells, spleen T cells, or lung endothelial cells. Specific delivery to a particular class or type of cells indicates that a higher proportion of lipid nanoparticles are delivered to target type or class of cells. In some embodiments, specific delivery may result in a greater than 2 fold, 5 fold, 10 fold, 15 fold, or 20 fold increase in the amount of therapeutic and/or prophylactic per 1 g of tissue of the targeted destination.

B. Methods of Gene Regulation

Methods of using the disclosed lipid nanoparticles for gene regulation are provided herein. In one embodiment, the lipid nanoparticles can be used for reducing gene expression in a target cell in a subject in need thereof. In such an embodiment, a subject is administered a lipid nanoparticle composition consisting of 3-[(1-Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and an inhibitory nucleic acid. The lipid nanoparticle can deliver the inhibitory nucleic acid to the target cell in the subject without a targeting ligand. The inhibitory nucleic acid can be siRNA.

Another embodiment provides methods of using the disclosed lipid nanoparticles for editing a gene in a cell in a subject in need thereof. In such an embodiment, the subject is administered two populations of lipid nanoparticles. The first population includes lipid nanoparticles having a formulation including Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and sgRNA specific for the gene that is being targeted. The second population of lipid nanoparticles includes lipid nanoparticles having a formulation including Adamantanyl)acetoxy]-2-{[3-(diethylamino)propoxycarbonyloxy]methyl}propyl (9Z,12Z)-9,12-octadecadienoate, DSPC, a polyethylene glycol-lipid, cholesterol, and mRNA encoding an RNA-guided DNA endonuclease. The RNA-guided DNA endonuclease can be Cas9, CasX, CasY, Cas13, or Cpf1.

In one embodiment, the cell that is targeted for gene regulation is an immune cell. The immune cell can be a T cell, such as CD8+ T cell, CD4+ T cell, or T regulatory cell.

Other exemplary immune cells for gene editing include but are not limited to macrophages, dendritic cells, or liver immune cells.

Exemplary genes that can be targeted include but are not limited to T cell receptors, B cell receptors, CTLA4, PD1, FOXO1, FOXO3, AKTs, CCR5, CXCR4, LAG3, TIM3, Killer immunoglobulin-like receptors, GITR, BTLA, LFA-4, T4, LFA-1, Bp35, CD27L receptor, TNFRSF8, TNFRSF5, CD47, CD52, ICAM-1, LFA-3, L-selectin, Ki-24, MB1, B7, B70, M-CSFR, TNFR-II, IL-7R, OX-40, CD137, CD137L, CD30L, CD40L, FasL, TRAIL, CD257, LIGHT, TRAIL-R1, TRAILR2, TRAIL-R4, TWEAK-R, TNFR, BCMA, B7DC, BTLA, B7-H1, B7-H2, B7-H3, ICOS, VEGFR2, NKG2D, JAG1, GITR, CD4, CCR5, GATA-3, MTORC1, MTORC2, RAPTOR, GATOR, FOXP3, NFAT, IL2R, and IL7.

Exemplary tumor-associated antigens that can be recognized by T cells and are contemplated for targeting, include but are not limited to MAGE1, MAGE3, MAGE6, BAGE, GAGE, NYESO-1, MART1/Melan A, MC1R, GP100, tyrosinase, TRP-1, TRP-2, PSA, CEA, Cyp-B, Her2/Neu, hTERT, MUC1, PRAME, WT1, RAS, CDK-4, MUM-1, KRAS, MSLN and β-catenin.

C. Subjects to be Treated

In some embodiments, the subjects treated are mammals experiencing cancer, autoimmune disease, infections disease, organ transplant, organ failure, or a combination thereof. In some embodiments, the methods described herein may cause T cells to present specific antigens for the treatment of cancer or autoimmune disease. In some embodiments, the methods described herein may be used for T cell priming. In some embodiments, the methods described herein may be used to deliver DNA or mRNA that cause T cells to present MHC-peptide complexes. In some embodiments, the methods described herein may be used to deliver one or more of DNA, siRNA, or mRNA to a T cell to avoid anergy.

EXAMPLES

Example 1. Preparation of a Constrained Lipid

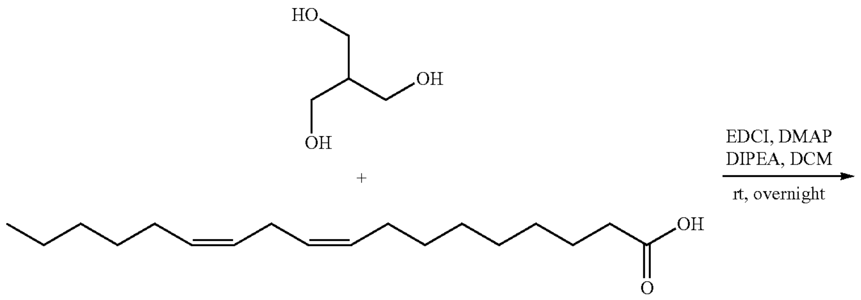

1

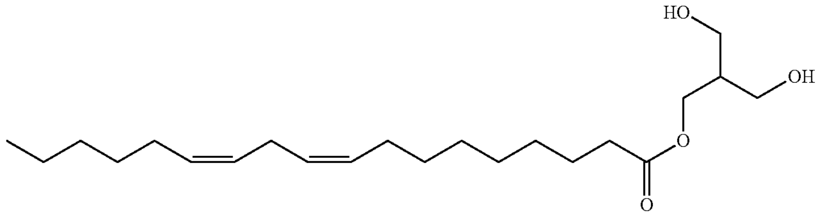

2

+

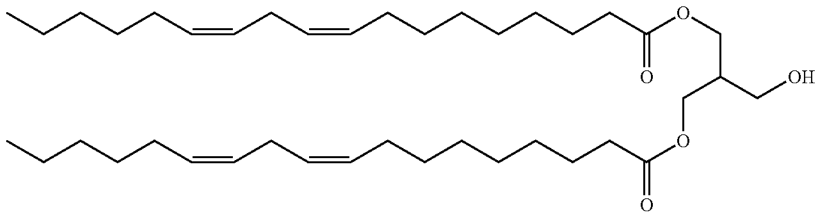

3

-continued

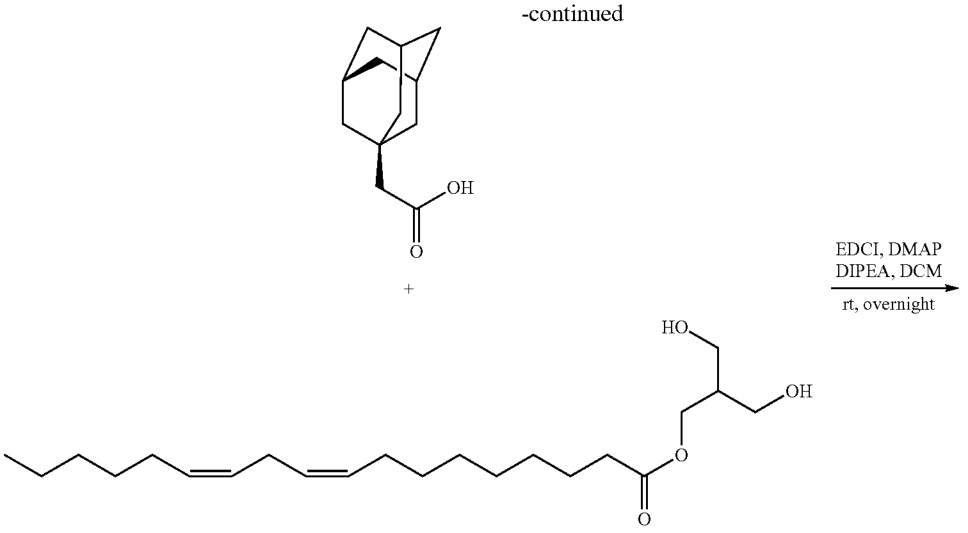

2

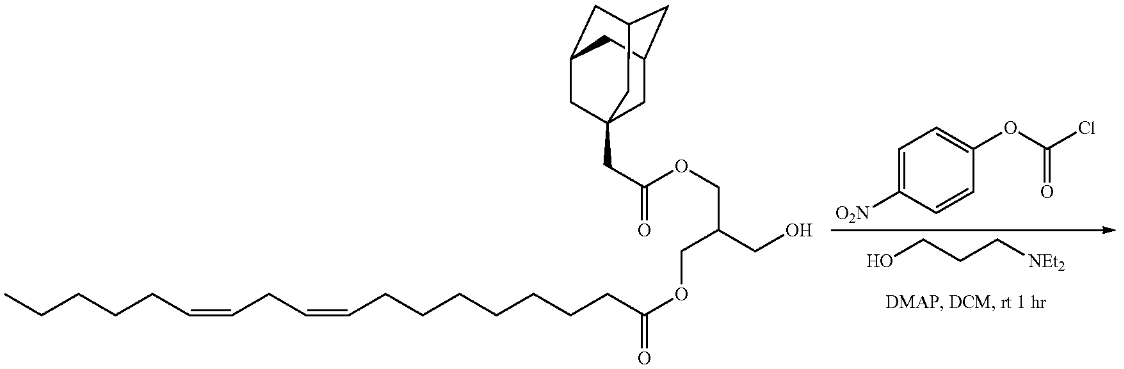

4

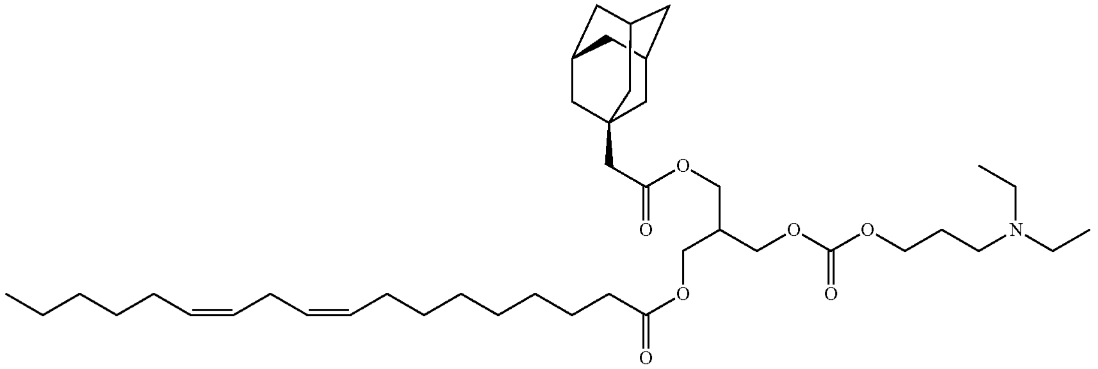

1-1

To a solution of linoleic acid 1 (4.0 g, 14.2 mmol), 4-dimethylaminopyridine (DMAP) (0.4 g, 2.9 mmol), N,N-diisopropylethylamine (DIPEA) (3.7 mL, 20.5 mmol) and 2-(hydroxymethyl)propane-1,3-diol (1.5 g, 14.2 mmol) in anhydrous $CH_2Cl_2$ (40 mL) under nitrogen atmosphere was added N-(3-dimethylaminopropyl)-N'-ethylcarbodiimide hydrochloride (EDCI) (4.1 g, 20.5 mmol) at 25° C. The reaction mixture was stirred at room temperature overnight and linoleic acid 1 was consumed completely as monitored by TLC. Then the reaction mixture was directly concentrated under reduced pressure. Purification of the crude residue via silica gel flash column chromatography (gradient eluent: 1-30% of EtOAc/hexane) afforded compound 2 (2.3 g, 44% yield) and compound 3 (1.7 g, 30% yield) as colorless oil.

To a solution of compound 2 (150 mg, 0.41 mmol), DMAP (10 mg, 0.1 mmol), DIPEA (0.1 mL, 0.6 mmol) and adamantane (79 mg, 0.41 mmol) in anhydrous $CH_2Cl_2$ (2 mL) under nitrogen atmosphere was added EDCI (114 mg, 0.6 mmol). The reaction mixture was stirred at room temperature overnight, and compound 2 was consumed completely as monitored by TLC. Then the reaction mixture was directly concentrated under reduced pressure. Purification of the crude residue via silica gel flash column chromatography (gradient eluent: 0-20% of EtOAc/hexane) afforded compound 4 (103 mg, 53% yield) as a colorless oil.

To a solution of compound 4 (76 mg, 0.16 mmol) and DMAP (45 mg, 0.37 mmol) in anhydrous $CH_2Cl_2$ (2 mL). Under nitrogen atmosphere was added 4-nitrophenylchloroformate (65 mg, 0.32 mmol). After stirring at room temperature for 1 hour, 3-diethylamino-1-propanol (0.44 mL, 0.96 mmol) was added into the reaction mixture and then stirred at room temperature for 1 hour. The reaction mixture was directly concentrated under reduced pressure. Purification of the crude residue via silica gel flash column chromatography (gradient eluent: 0-4% of MeOH/DCM) afforded compound 1-1 (32 mg, 29% yield) as a colorless oil. HRMS (ESI, m/z) calculated for $C_{42}H_{72}NO_7$ $[M+H]^+$: 702.5303, found 702.5277.

Other lipids were prepared by methods similar to the steps described in this example.

Example 2. Lipid Nanoparticles Containing a Conformationally Constrained Lipid can Form Stable LNPs Materials and Methods:

Nanoparticle Formulation. Nanoparticles were formulated using a microfluidic device as previously described. Briefly, nucleic acids (siRNA and DNA barcodes) were diluted in citrate buffer while lipid-amine compounds, alkyl tailed PEG, cholesterol, and DSPC were diluted in ethanol. PEG, cholesterol, and DSPC was purchased from Avanti Lipids. Citrate and ethanol phases were combined in a microfluidic device by syringe pumps.

Nanoparticle Characterization. LNP hydrodynamic diameter was measured using a plate reader formatted dynamic light scattering machine (Wyatt). LNPs were diluted in sterile 1×PBS to a concentration of ~0.06 μg/mL and analyzed. LNPs were only included if they formed monodisperse populations with diameter between 20 and 200 nm. Particles that met these criteria were dialyzed with 1× phosphate buffered saline (PBS, Invitrogen), and were sterile filtered with a 0.22 μm filter.

Figure 1B:
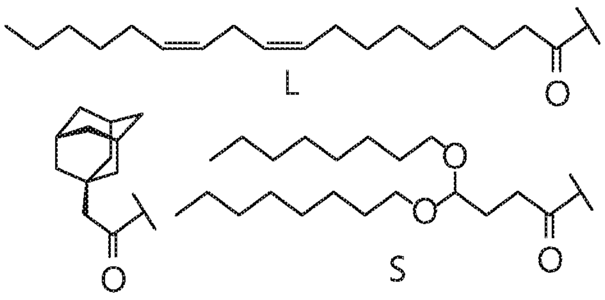
FIG. 1D is a schematic showing 4 molar ratios of ionizable lipid, cholesterol, lipid-PEG, and either DSPC or DOPE used to formulate 104 distinct LNPs.
FIG. 1E is a dot plot showing hydrodynamic diameter (nm) of all formulated LNPs, measured individually.
FIG. 1F is a dot plot showing polydispersity index of all formulated LNPs, measured individually.
FIGS. 1G-1I are bar graphs showing hydrodynamic diameter of LNPs plotted as a function of ionizable lipid type (FIG. 1G), molar percent of ionizable lipid (FIG. 1H), and phospholipid type (FIG. 1I).

Results:

13 chemically diverse lipids containing amines were synthesized. The library was constructed to investigate whether the structure of the (i) amine and (ii) lipid tail affected delivery. A 'scaffold' lipid containing the unsaturated lipid linoleate and two ester bonds was purified (FIG. 1A). This scaffold did not have any amines. Amine variants were attached to the reactive sites, in order to create chemical diversity (FIG. 1A). At reactive site 1, 3 lipid tails with diverse structures (FIG. 1B) were added via esterification. The control tail, L, was linoleate which created a construct with two identical lipid tails. Lipid S contained two lipid tails, bringing the total number of tails to 3. Finally, tail A contained adamantane, a constrained lipid with a defined 'armchair' structure. At reactive site 2, 11 amine-containing head groups were added via esterification, resulting in head groups linked by ester or carbonate linkages, respectively. Head groups were chose based on previous reports that small molecules with similar structures have biological activity. After synthesis, the chemical structure of all 13 lipids was confirmed using high resolution mass spectroscopy or 1H-NMR. For clarity, each ionizable lipid was named with the nomenclature, head group number—tail letter (e.g. 1-L, 11-A).

Figure 1C:
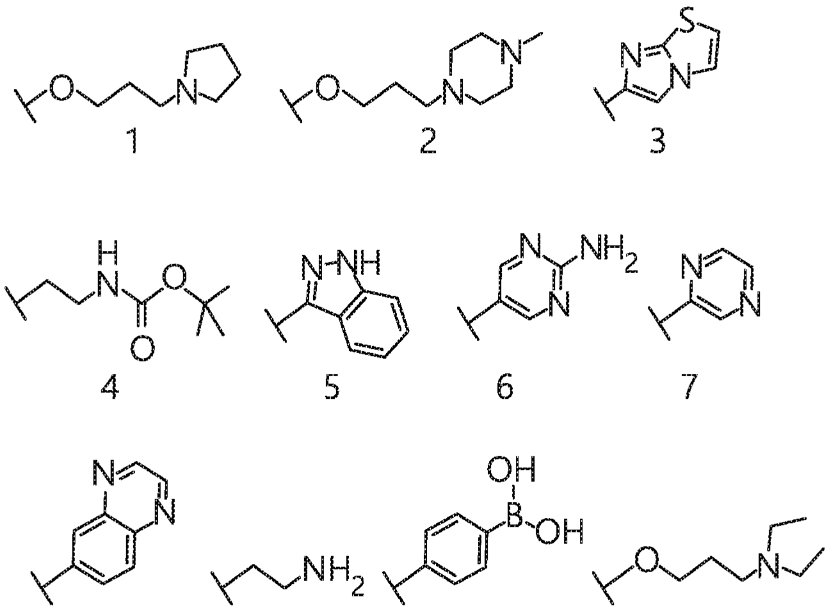
Figure 1D:
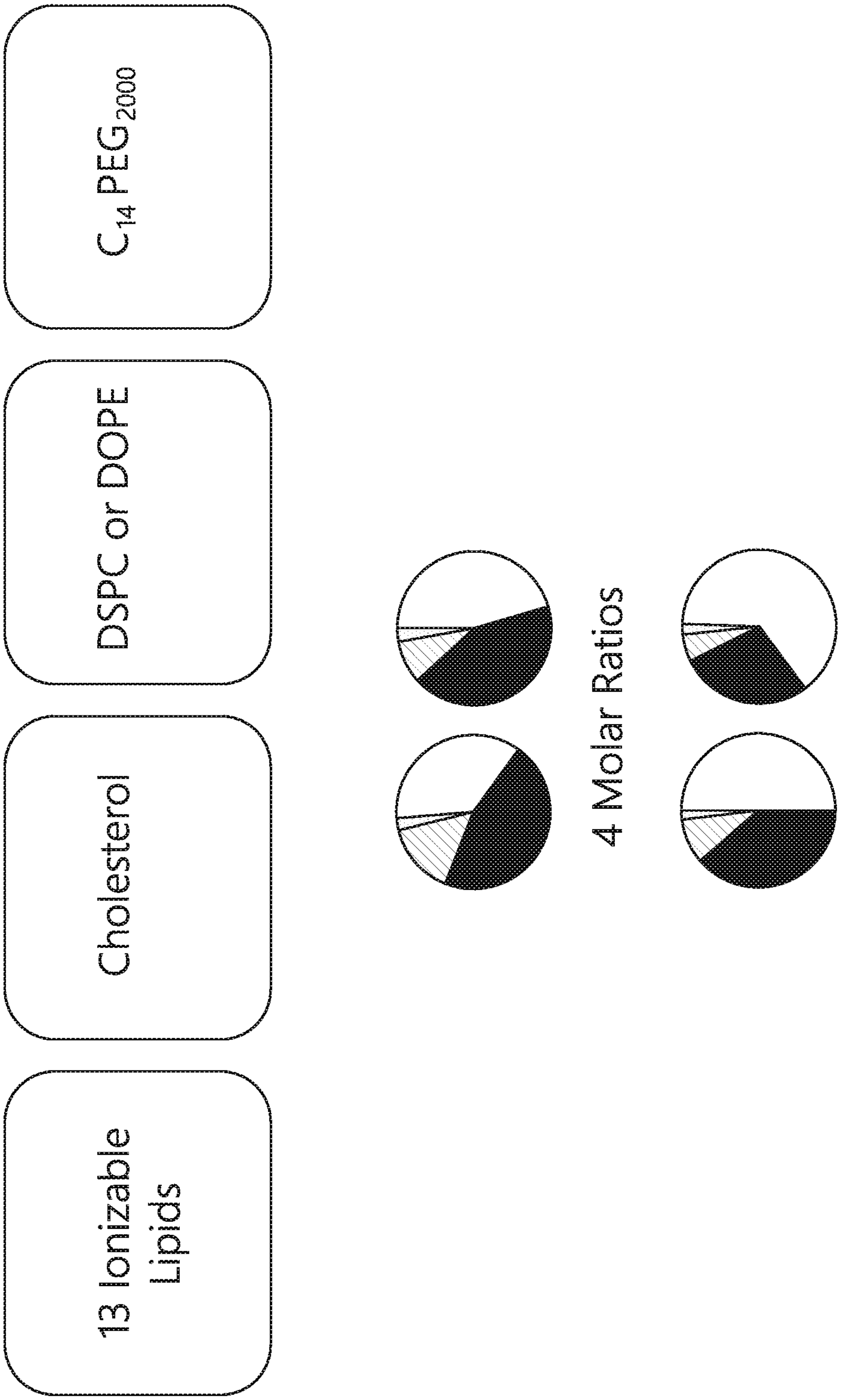
Figure 1E:
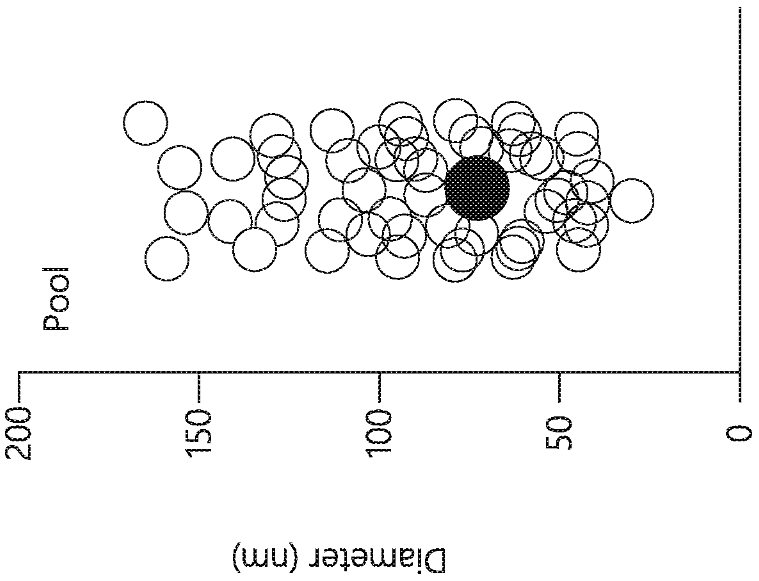
Figure 1F:
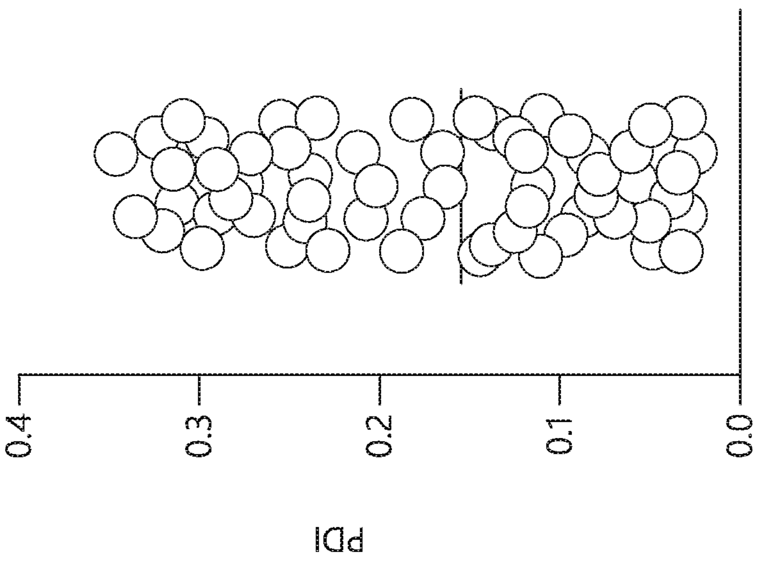
Figure 1G:
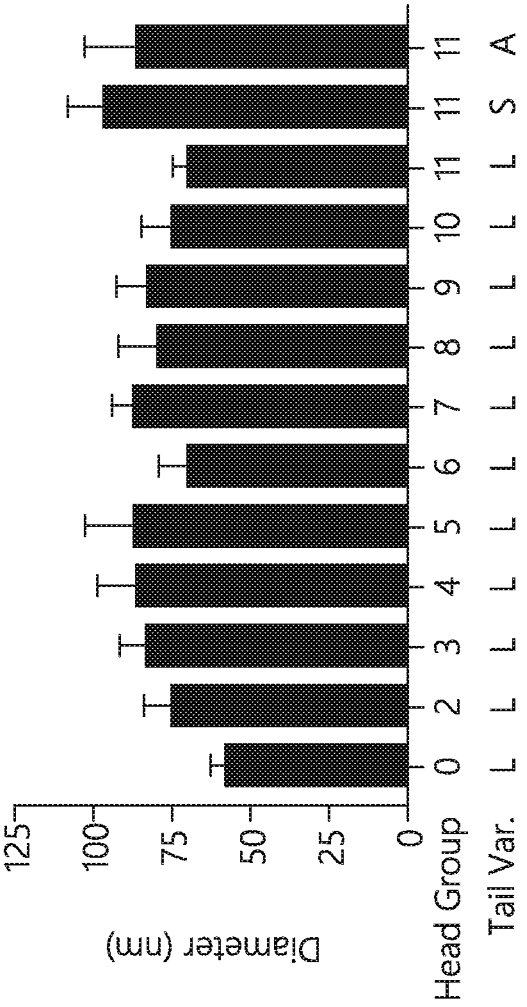
Figure 1H:
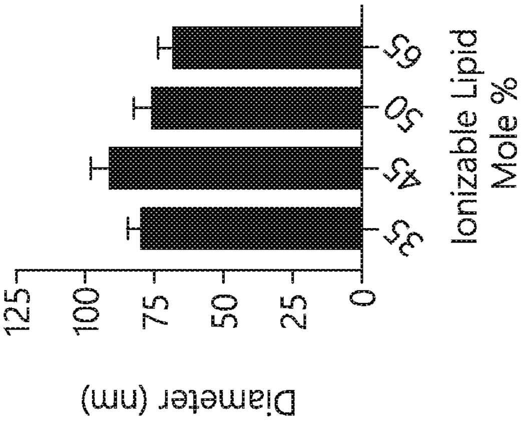
Figure 1I:
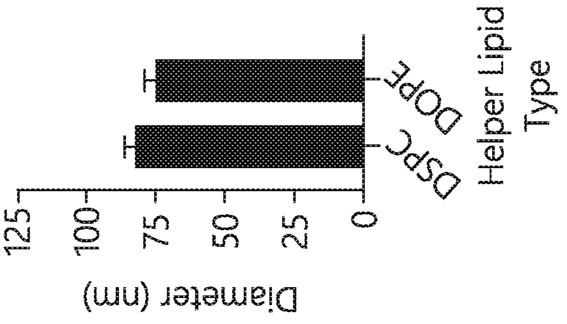

The ability of the 13 ionizable lipids (FIG. 1A-C) to form stable LNPs was investigated. The hydrodynamic diameter of LNPs carrying a chemically modified siRNA targeting GFP (siGFP) (Paunovska, et al., *ACS Nano,* 12:8341-8349 (2018)) as well as a DNA barcode (Sago et al., *Nano Lett*, (2018)) was measured. The LNPs were formulated using microfluidics (Chen, D., et al., *J Am Chem Soc,* 134:6948-6951 (2012)). Previously validated compounds were added to reduce the chance the results were affected by other constituents added to the LNP. The previously validated compounds were C14PEG2000, unmodified cholesterol, and either 1-2-distearoyl-sn-glycero-3-phosphocholine (DSPC) or 1-2-dioleoyl-sn-glycero-3-phosphoethanolamine (DOPE) (FIG. 1D). As a control to ensure the results were not affected by the molar ratio of the 4 components, each lipid was formulated with 2 phospholipids and 4 molar ratios, for a total of 104 LNPs (FIG. 1D). Notably, 100 of the LNPs formed small, monodisperse populations, as evidenced both by hydrodynamic diameter and polydispersity index. The diameter for individual LNPs varied between 30 and 170 nm, with an average of 76 nm (FIG. 1E) and an average PDI of 0.15 (FIG. 1F). The hydrodynamic diameter was analyzed as a function of ionizable lipid (FIG. 1G), molar ratio of the four constituents (FIG. 1H), and the type of phospholipid (DSPC/DOPE) added to the formulation (FIG. 1I). In all cases, the average diameter varied between 50 and 100 nm. These data show that non-traditional lipids formed LNPs with hydrodynamic diameters similar to lipoproteins and natural viruses.

Example 3. A High Throughput siRNA Screen for In Vivo Activity Reveals LNPs with Constrained Lipids have Biological Activity in T Cells Materials and Methods:

DNA Barcoding. Each chemically distinct LNP was formulated to carry its own unique DNA barcode and siRNA. For example, LNP1 carried DNA barcode 1 and siICAM2, while the chemically distinct LNP2 carried DNA barcode 2 and siGFP. Single stranded DNA sequences were purchased from Integrated DNA Technologies (IDT). To ensure equal amplification of each sequence, we included universal forward and reverse primer regions. Each barcode was distinguished using a unique 8 nucleotide sequence. An 8 nucleotide sequence can generate 65,536 distinct barcodes. 156 distinct sequences designed to prevent sequence 'bleaching' on the Illumina MiniSeq sequencing machine were used.

Animal Experiments. All animal experiments were performed in accordance with the Georgia Institute of Technology's IACUC. C57BL/6J (#000664), GFP (#003291), and constitutive SpCas9 (#026179) mice were purchased from The Jackson Laboratory and used between 5-12 weeks of age. In all experiments, N=3-5 mice/group were used. Mice were injected intravenously via the lateral tail vein. The nanoparticle concentration was determined using NanoDrop (Thermo Scientific).

Cell Isolation & Staining. Cells were isolated 72 hours (for screens) or 120 hours (for in vivo gene editing) hours after injection with LNPs unless otherwise noted. Mice were perfused with 20 mL of 1×PBS through the right atrium. As previously described (Dahlman, et al., *Nat Nano,* 9:648-655 (2014); Paunovska, K., et al., *Nano Lett,* 18:2148-2157 (2018)), tissues were cut and placed in a digestive enzyme solution with Collagenase Type I (Sigma Aldrich), Collagenase XI (Sigma Aldrich) and Hyaluronidase (Sigma Aldrich) at 37° C. for 45 minutes. The digestive enzyme for heart included Collagenase IX. Cell suspension was filtered through 70 μm mesh and red blood cells were lysed. Cells were stained to identify populations and sorted using the BD FacsFusion in the Georgia Institute of Technology Cellular Analysis Core for in vivo experiments. The antibody clones used were: anti-CD31 (390, BioLegend), anti-CD45.2 (104, BioLegend), anti-CD19 (6D5, Biolegend), anti-CD3 (17A2, Biolegend), anti-CD8a (53-6.7, Biolegend), and anti-CD4 (GK1.5, Biolegend).

PCR Amplification for Illumina Sequencing. All samples were amplified and prepared for sequencing using nested PCR. 2 μL of primers were added to 5 μL of Kapa HiFi 2× master mix, and 3 μL template DNA/water. The second PCR, added Nextera XT chemistry, indices and i5/i7 adapter regions. Dual-indexed samples were run on a 2% agarose gel to ensure that PCR reaction occurred before being pooled and gel purified.

Deep Sequencing. Illumina sequencing was conducted in Georgia Institute of Technology's Molecular Evolution core. Runs were performed on an Illumina Miniseq. Primers were designed based on Nextera XT adapter sequences.

Barcode Sequencing Normalization. Counts for each particle, per cell type, were normalized to the barcoded LNP mixture applied to cells or injected into the mouse.

TNS Assay. The pKa of 7C1 and BM1 was measured as previously described (Dahlman, J. E., et al., *Nat Nano,* 9:648-655 (2014)). Briefly, a stock solution of 10 mM HEPES (Sigma), 10 mM MES (Sigma), 10 mM sodium acetate (Sigma), and 140 nM sodium chloride (Sigma) was prepared and pH adjusted with hydrogen chloride and sodium hydroxide to a range of pH between 4 and 10. Using 4 replicates for each nanoparticle at each pH, 140 μL pH-adjusted buffer was added to a 96-well plate, followed by the addition 5 μL of 2-(p-toluidino)-6-napthalene sulfonic acid (60 μg/mL). 5 μL of each nanoparticle was added to each well. After 5 minutes of incubation under gentle shaking, fluorescence absorbance was measured using excitation wavelengths of 325 nm and emission wavelength of 435 nm.

RNA interference. siRNAs were chemically modified at the 2' position to increase stability and negate immunostimulation. 72 hours after injection, tissues were isolated and protein expression was determined via flow cytometry. GFP mean fluorescent intensity in PBS-treated mice was normalized to 100 percent.

In vivo Cas9 Editing. Mice constitutively expressing SpCas9 were injected with cLNP carrying 2 mg/kg of sgGFP. 5 days after injection, cells were isolated via FACS. Indels were measured by TIDES.

Figure 2A:
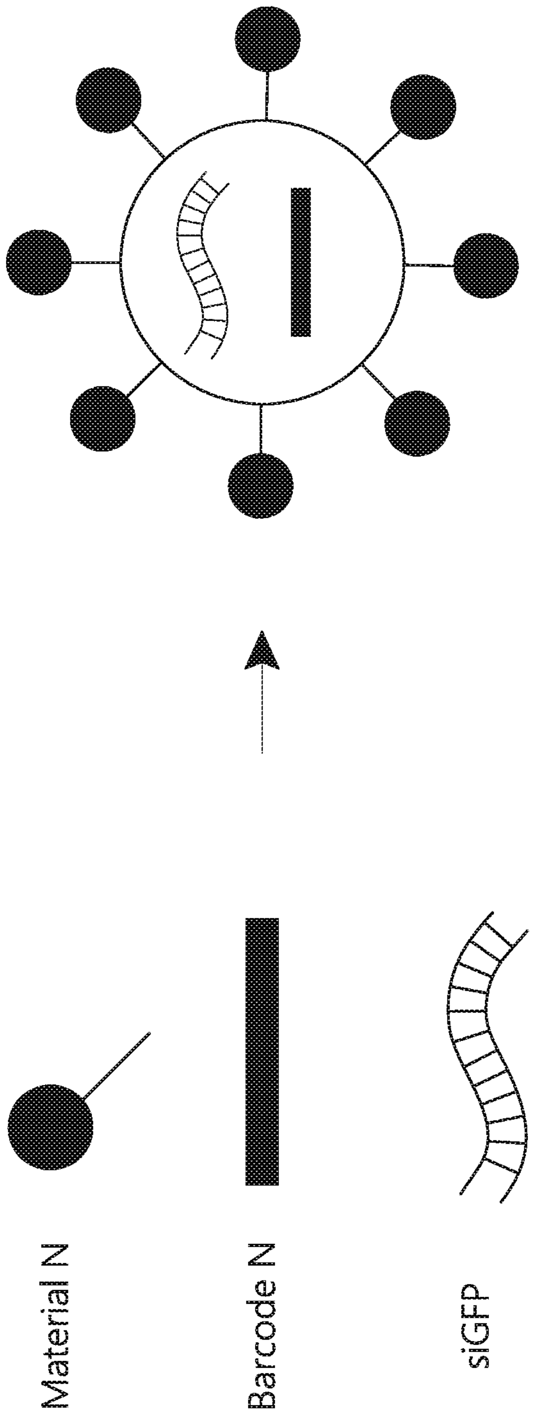
FIG. 2A is a schematic showing the nanoparticles formulated to carry a distinct DNA barcode and siGFP.
Figure 2B:
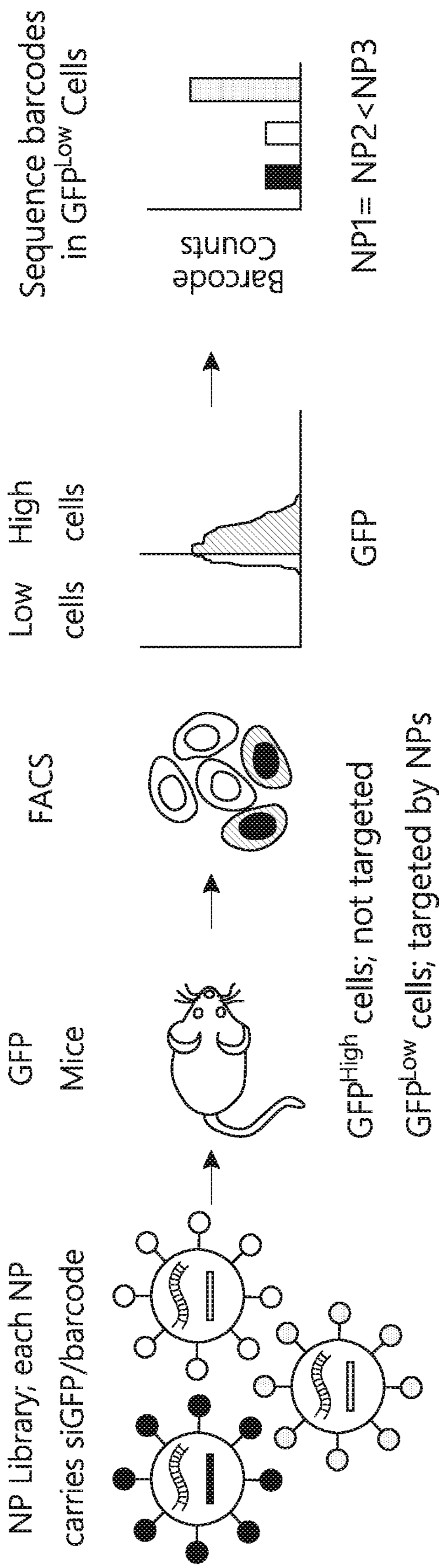
FIG. 2B is a schematic showing an experimental workflow including steps of pooling 100 stable LNPs together, administering them to mice expressing GFP, isolating $GFP^{Low}$ cells after 3 days, and sequencing the DNA barcodes within that population.

Results:

LNP delivery of siRNA to target cells (in this case, T lymphocytes) as well as 8 off-target cell types in vivo was evaluated. siGFP chemically modified to reduce immunostimulation and enhance on-target silencing via preferential antisense RISC loading (FIG. S2A) was used. Studying 1 LNP per group, and using 5 mice/group, this screen would require >500 mice and significant time/flow cytometry resources. Therefore a DNA barcode-based screen was developed to evaluate how over 100 LNPs functionally delivered siGFP, in any combination of target cells, in a single mouse (FIG. 2A). LNP-1, with chemical structure 1, was formulated to carry siGFP and DNA barcode 1. LNP-N, with chemical structure N, was separately formulated to carry siGFP and DNA barcode N. Naked barcodes were also included as an experimental control (Paunovska, K., et al., *Nano Lett,* 18:2148-2157 (2018)), since DNA does not readily cross the cell bilayer. The LNPs were pooled together, and intravenously injected into mice that constitutively express GFP under a CAG promoter (FIG. 2B). The GFP acted as the functional delivery readout. It was hypothesized that LNPs which functionally delivered siGFP into the cytoplasm would have lower GFP protein expression. Thus, 3 days after injecting mice, $GFP^{Low}$ cells were isolated using fluorescence activated cell sorting (FACS), and deep sequenced to quantify the efficiency with which all N LNPs delivered barcodes into the cells. Normalized delivery, i.e., the number of barcodes for each individual barcode, normalized by the total number of barcode counts within that sample, was used. Normalized delivery can be used to analyze barcoded LNP datasets and is analogous to counts per million in RNAseq experiments (Lokugamage, M. P., et al., *Current Opinion in Biomedical Engineering,* 7:1-8 (2018)). Since GFP is expressed in all cell types, this assay can (i) compare GFP knockdown in any combination of on-/off-target cells and (ii) quickly identify LNPs that co-localized in GFPLow cells, all in a single animal.

Figure 2C:
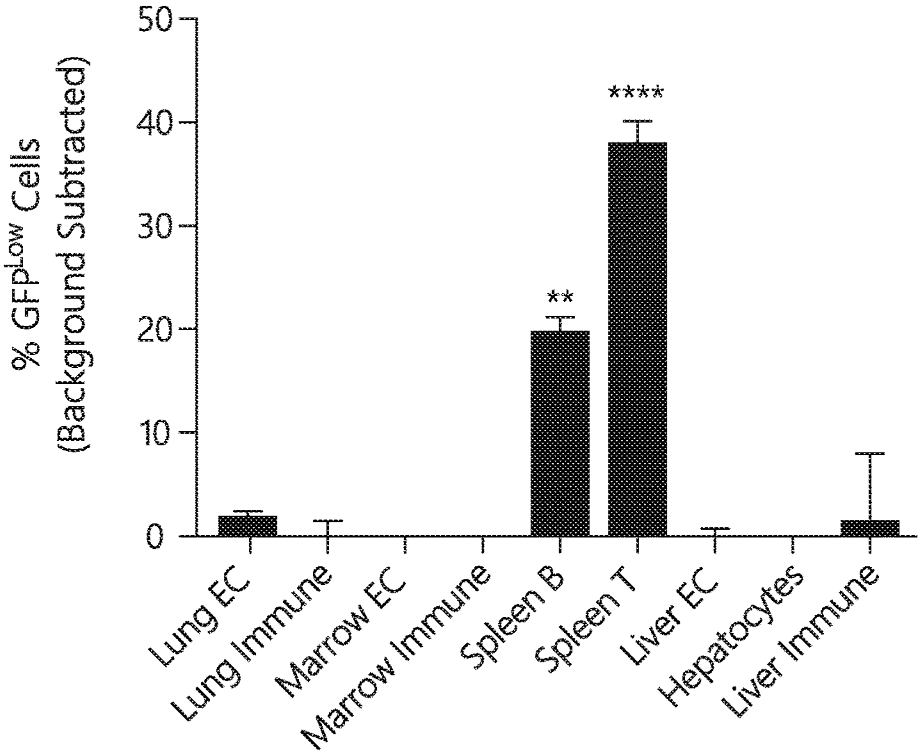
FIG. 2C is a bar graph showing the percent $GFP^{Low}$ cells in 9 cell types.
Figure 2D:
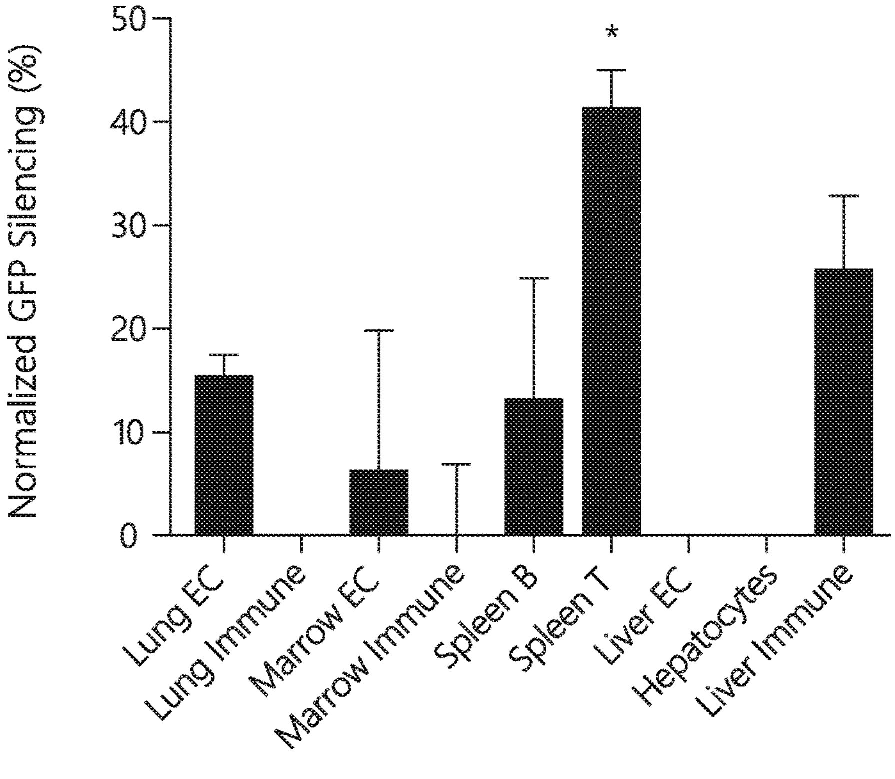
FIG. 2D is a bar graph showing the percent GFP MFI in 9 cell types.
Figure 2E:
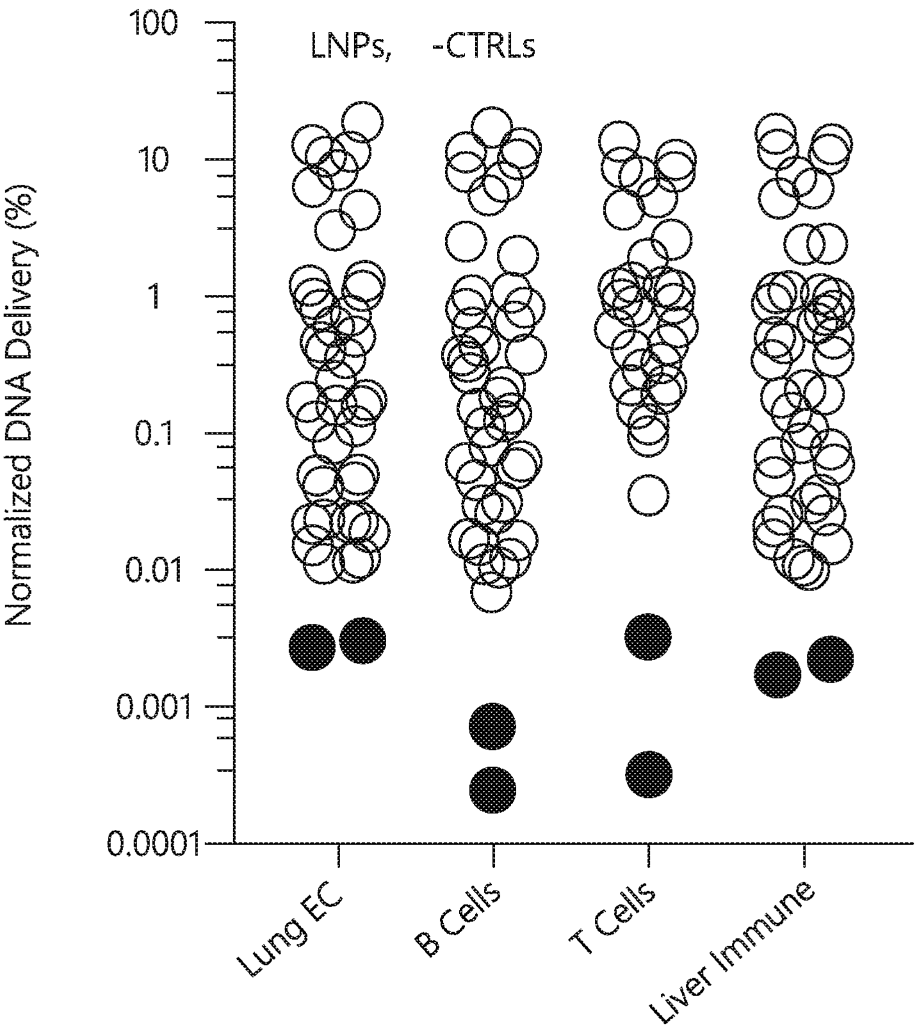
FIG. 2E is a dot plot showing normalized DNA delivery in lung endothelial cells, splenic B and T cells, as well as liver immune cells.

Three days after injecting a total dose of 1.5 mg/kg into mice (100 distinct LNPs, 0.015 mg/kg/particle on average), GFP silencing was quantified in 9 cell types. Compared to PBS treated mice, there was an increased number of $GFP^{Low}$ splenic B cells and splenic T cells (FIG. 2C). The average GFP protein silencing, quantified by mean fluorescent intensity, was highest in splenic T cells, followed by liver immune cells, splenic B cells, and lung endothelial cells (FIG. 2D). Surprisingly, no evidence of silencing was found in hepatocytes, a cell type that is preferentially targeted 12-15 by most LNPs (FIG. 2C,D). To check the quality of this dataset, the $GFP^{Low}$ lung splenic T cells were sequenced, and as a further check, lung endothelial cells, splenic B cells, and liver immune cells were also sequenced. In all 4 cell types, the normalized delivery of both negative controls (naked barcodes) was lower than barcodes delivered by LNPs, as expected (FIG. 2E).

Figure 2F:
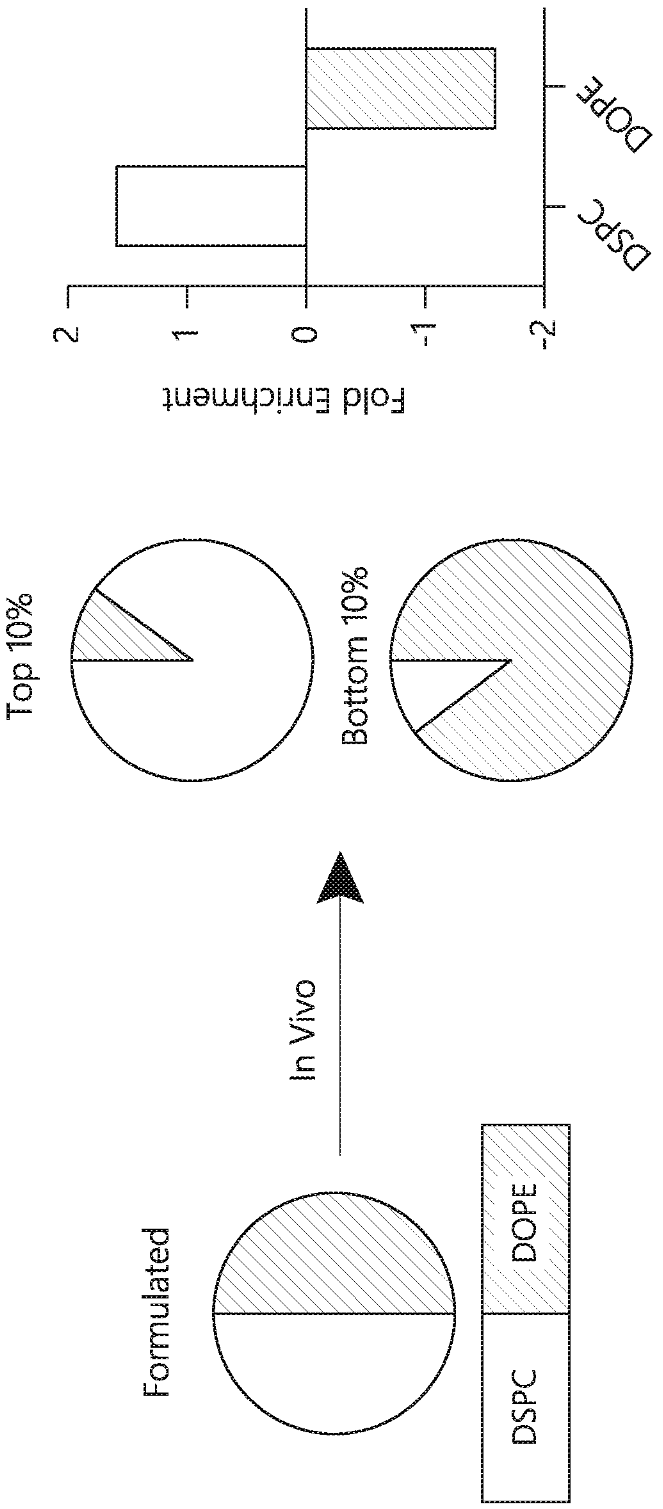
FIG. 2F is a schematic showing the enrichment of DSPC-containing LNPs in splenic T cells.
Figure 2H:
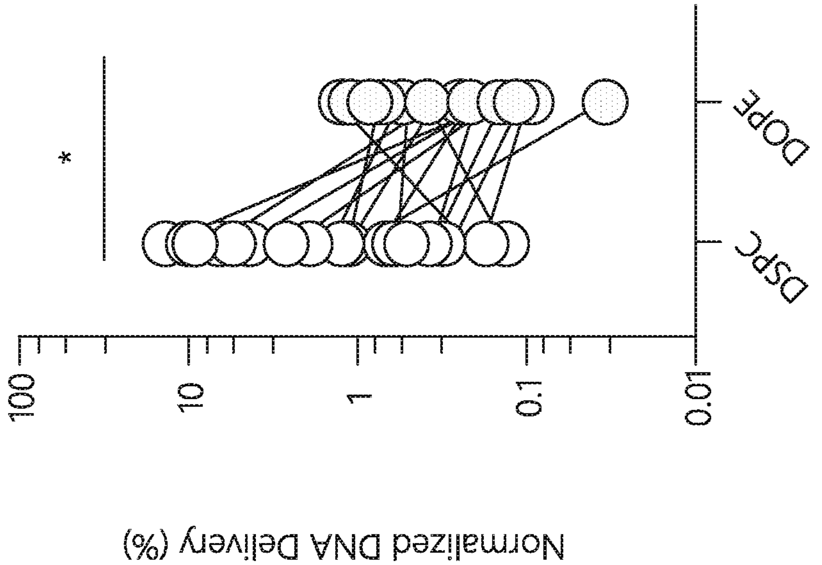
FIG. 2G is a dot plot showing normalized DNA delivery of LNPs plotted as a function of phospholipid. 2-way T test, $^{}P<0.01$.
FIG. 2**H is a paired analysis of normalized DNA delivery of LNPs containing DSPC or DOPE. Paired 2-way T test, $^{*}P<0.05$.
FIG. 2I is a bar graph showing enrichment for each of the 13 ionizable lipids.
FIG. 2J is a bar graph showing normalized DNA delivery of LNPs formulated with head group 11 and tail L, S, or A. One-way ANOVA, $^{*}P<0.05$, $^{**}P<0.01$.
Figure 2G:
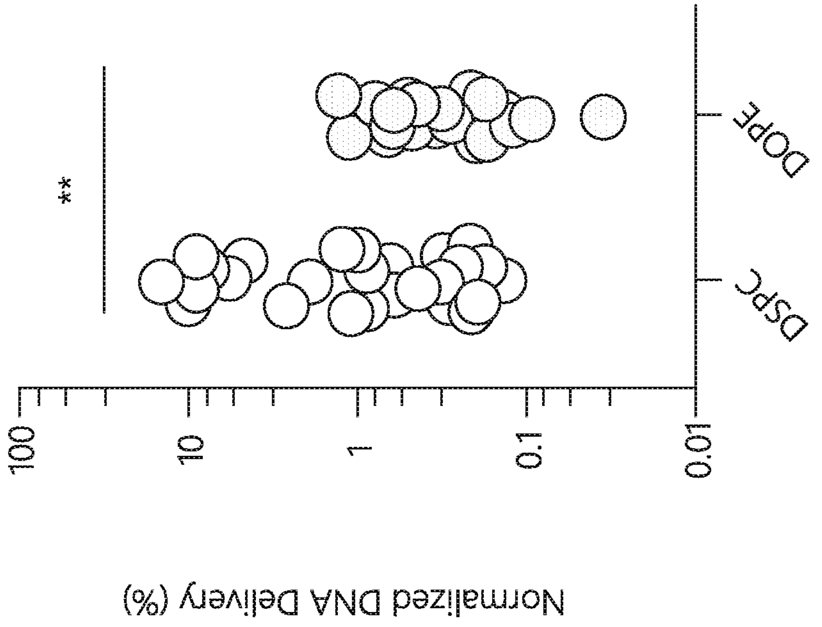

A large-scale in vivo structure function analysis using the DNA sequencing data was then performed to evaluate whether any nanoparticle material properties promoted delivery to splenic T cells. The enrichment for different nanoparticle properties was calculated. Enrichment is the odds a nanoparticle with a particular property would show up by chance in particles that (i) performed in the top 10%, and separately, (ii) particles that performed in the bottom 10% was calculated. Nanoparticles formulated with DSPC were enriched in effective particles, whereas nanoparticles formulated with DOPE were enriched in particles that performed poorly (FIG. 2F). To confirm these results, the normalized delivery for all LNPs formulated with DSPC and DOPE, respectively, was compared. DSPC-containing LNPs outperformed DOPE-containing LNPs (FIG. 2G). Finally, the normalized delivery of 'paired' LNPs was calculated, i.e., LNPs that had the same molar ratios and ionizable lipids (but different phospholipids). The specific DSPC LNPs that significantly outperformed their paired DOPE containing LNP were identified (FIG. 2H). Based on these data, it was concluded that the phospholipid contained within the LNP affected splenic T cell delivery. Having observed the impact of phospholipid, future chemical analysis was limited to DSPC containing formulations.

Figure 2I:
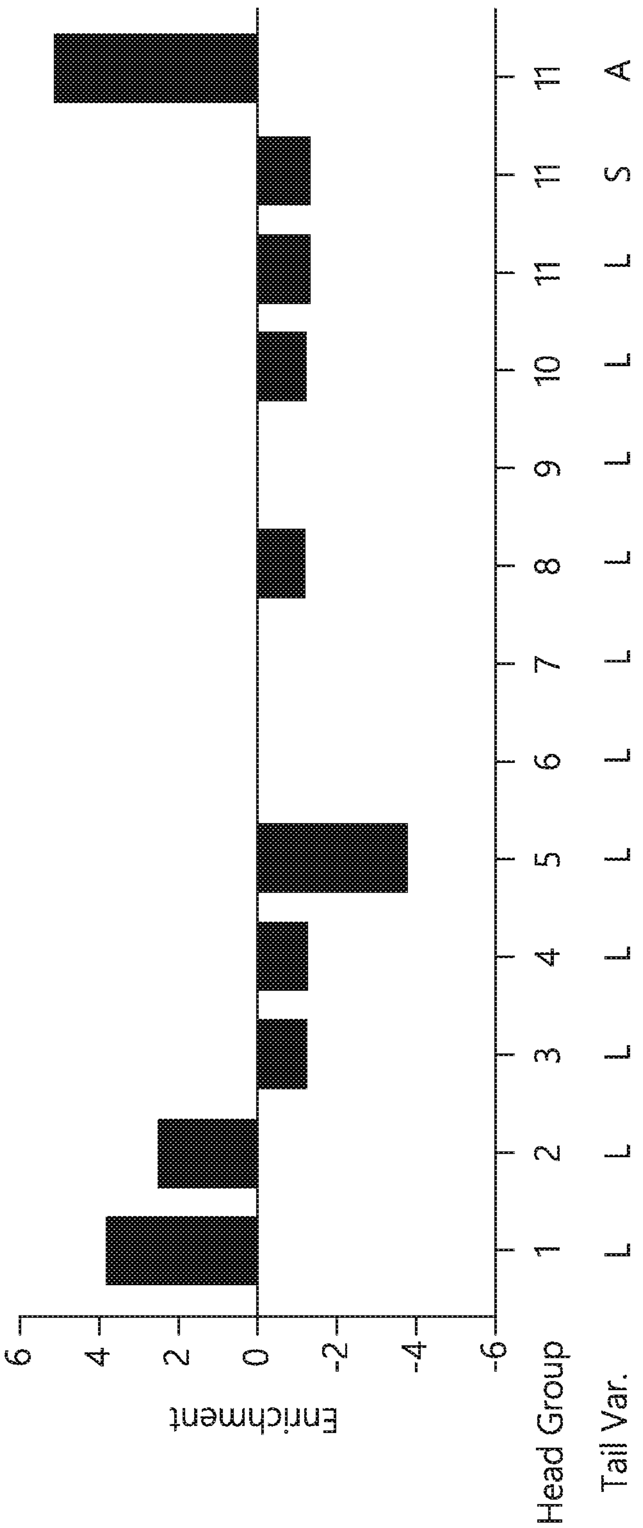
Figure 2J:
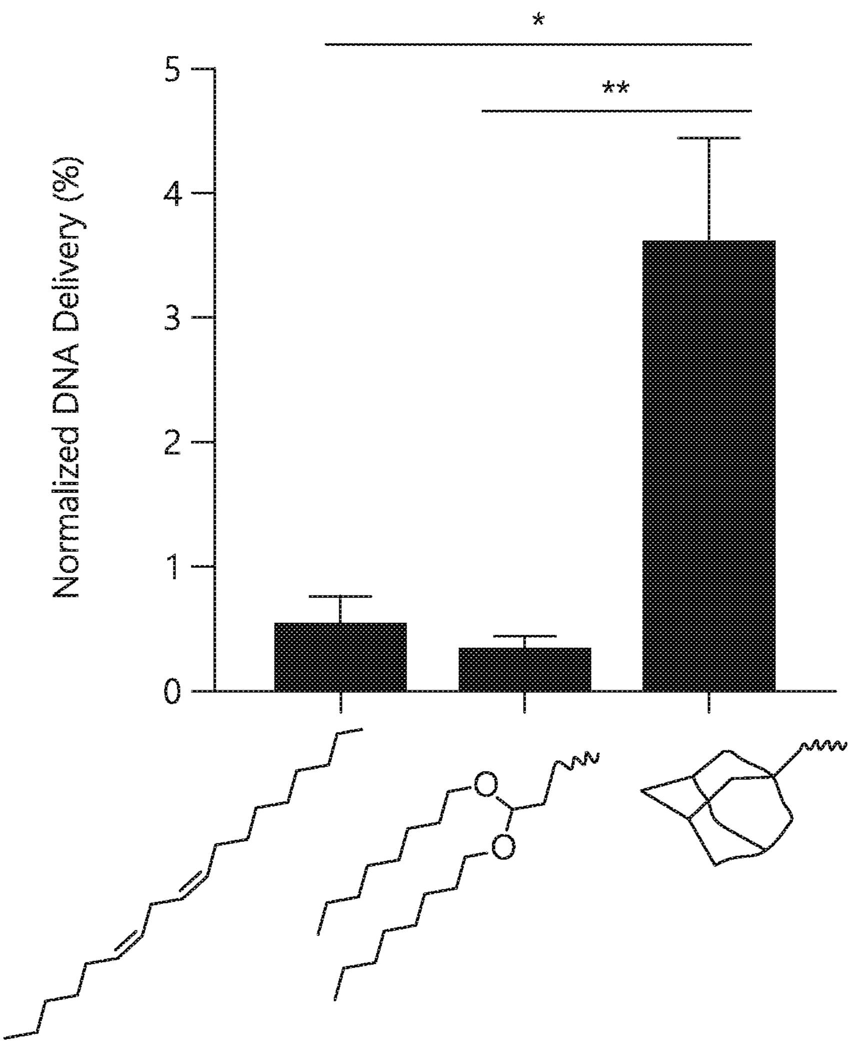
Figure 4A:
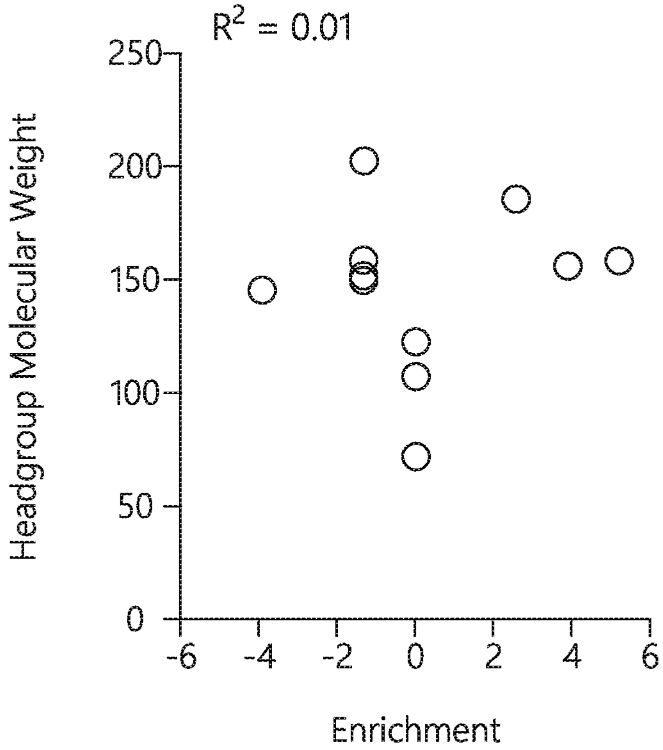
FIG. 4A shows a graph relating the molecular weight of the headgroup of the ionizable lipid to the enrichment in T-cells.
Figure 4B:
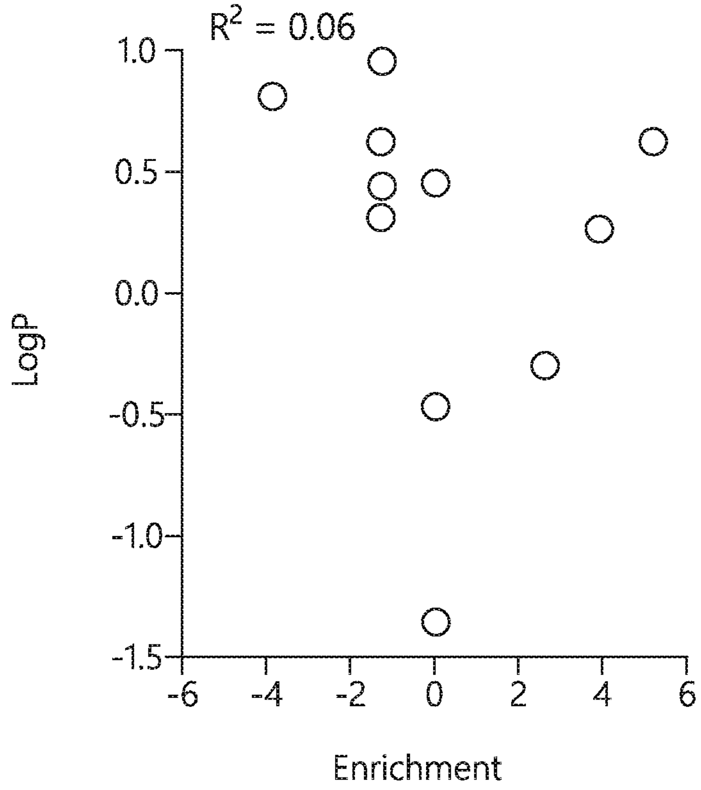
FIG. 4B shows a graph relating the Log P of the headgroup of the ionizable lipid to the enrichment in T-cells.
Figure 4C:
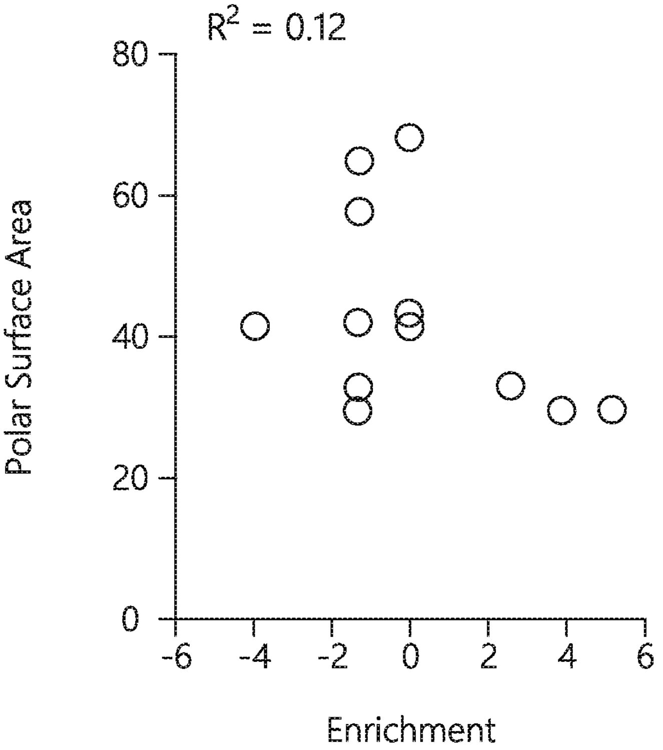
FIG. 4C shows a graph relating the Log P of the polar surface area of the headgroup on the ionizable lipid to the enrichment in T-cells.
Figure 4D:
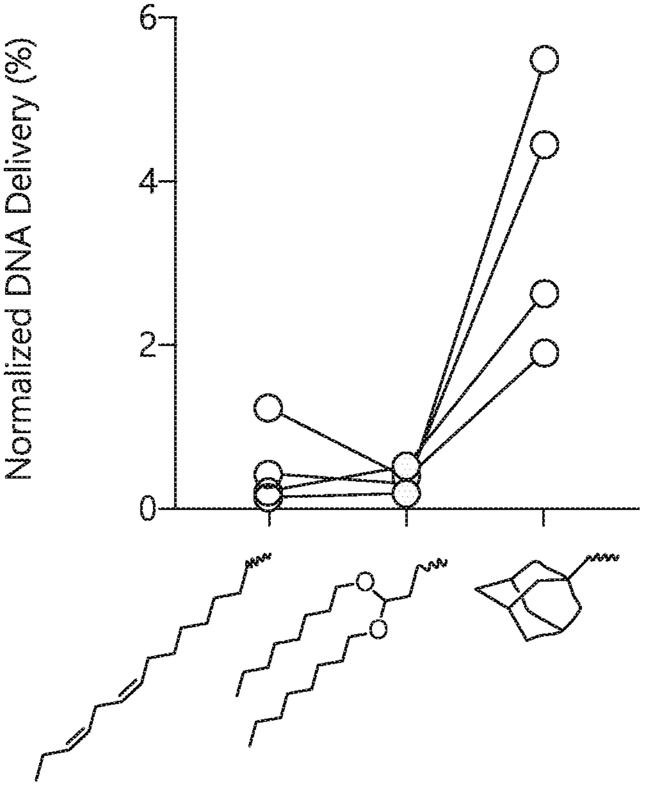
FIG. 4D shows a paired analysis of LNPs containing DSPC and ionizable lipids differing only by one tail.
Figure 4E:
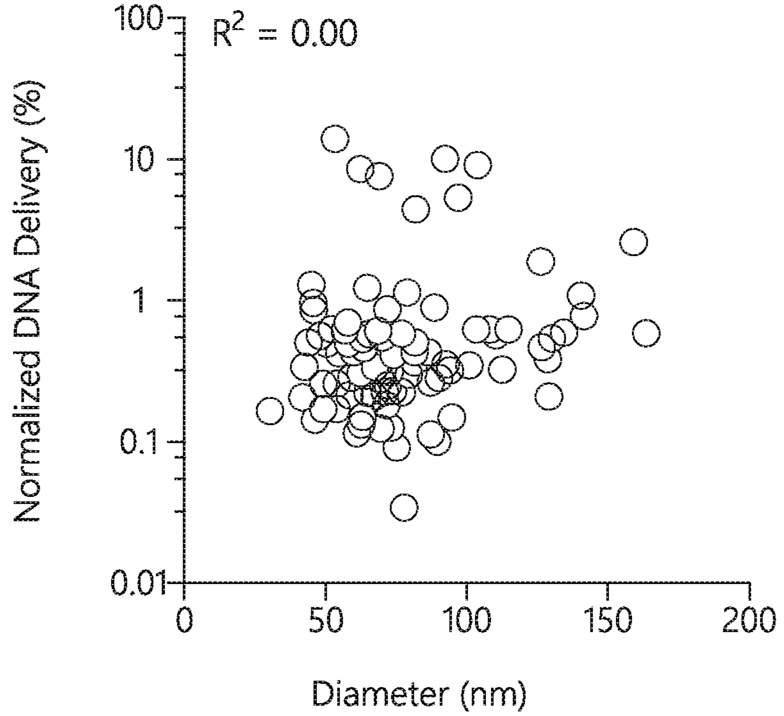
FIG. 4E shows a comparison of normalized DNA Delivery and LNP diameter.
Figure 5A:
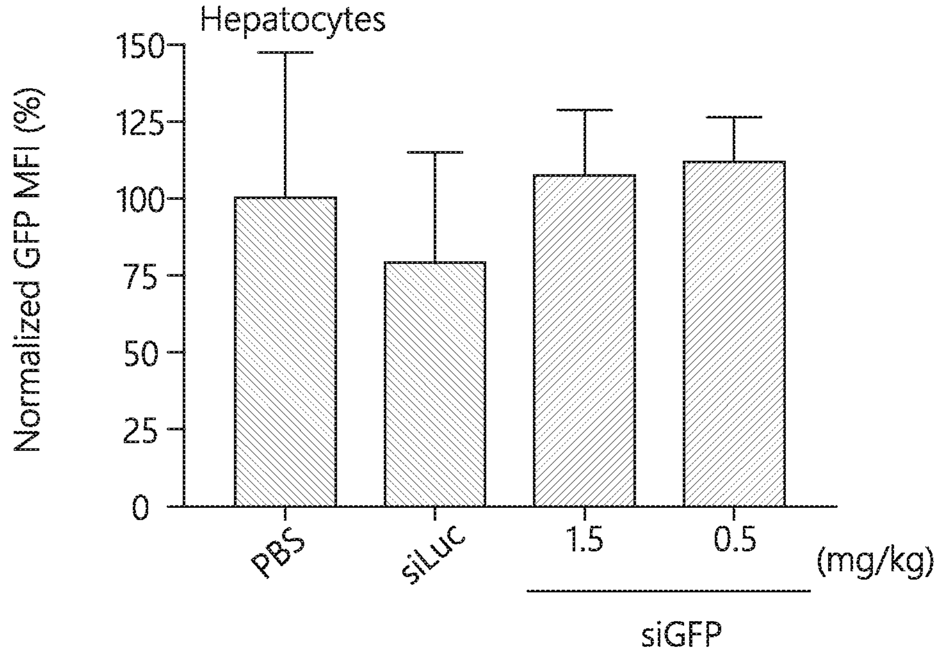
FIG. 5A-F are the normalized GFP protein MFI in PBS-treated mice as well as those dosed with LNP containing constrained lipid delivering siLuciferase, and siGFP (at 1.5 mg/kg and 0.5 mg/kg) to hepatocytes, liver immune cells, liver Kupffer cells, Liver Endothelial cells, Splenic monocytes, and Splenic B Cells.
Figure 5B:
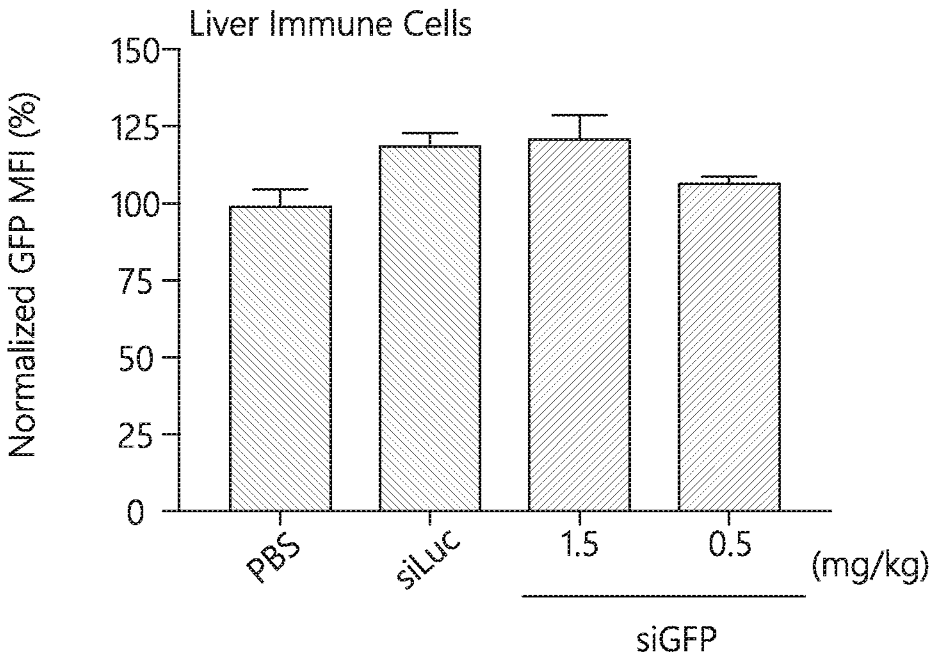
Figure 5C:
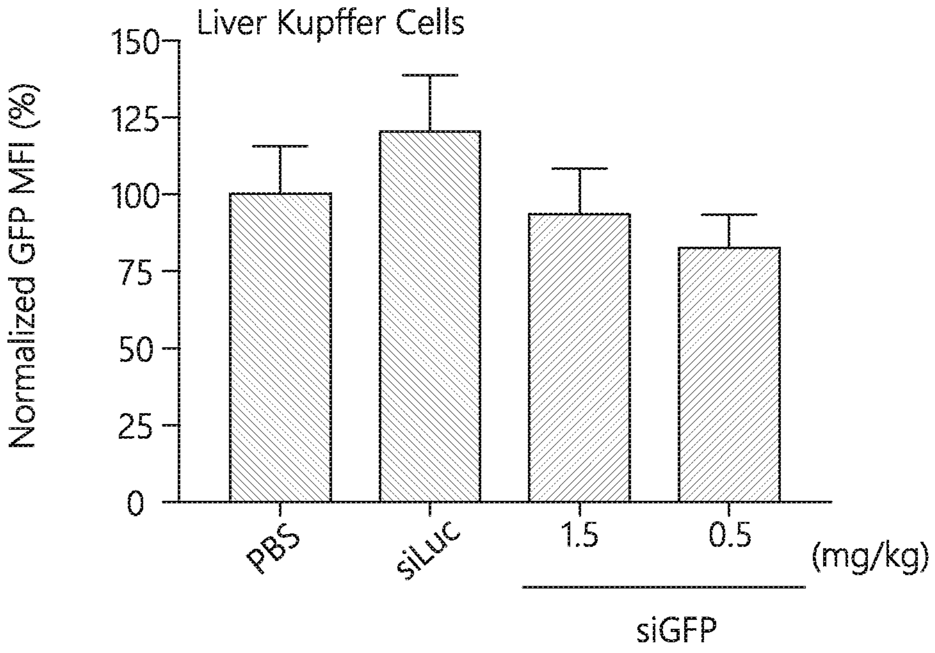
Figure 5D:
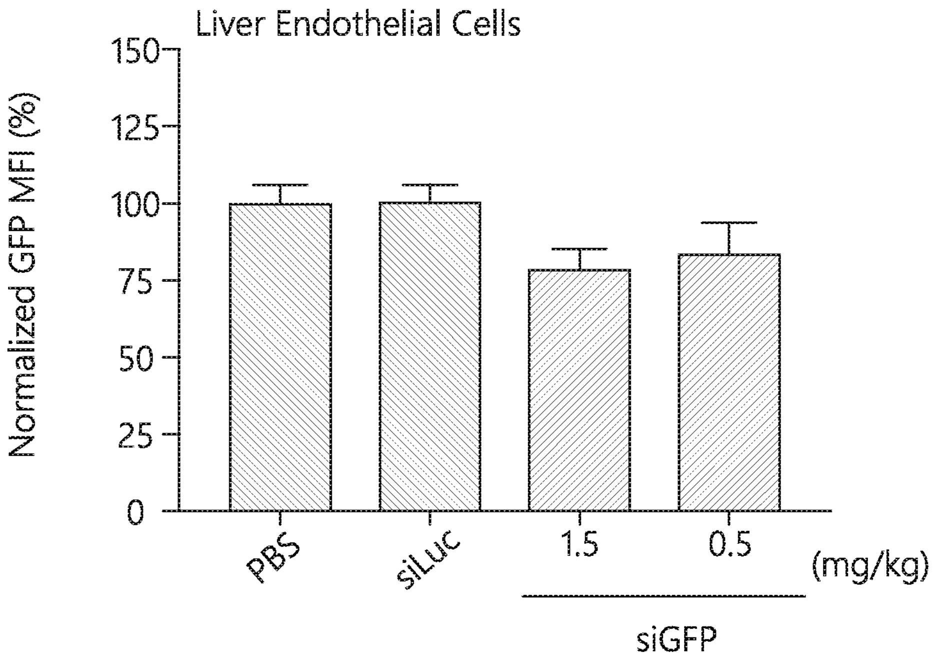
Figure 5E:
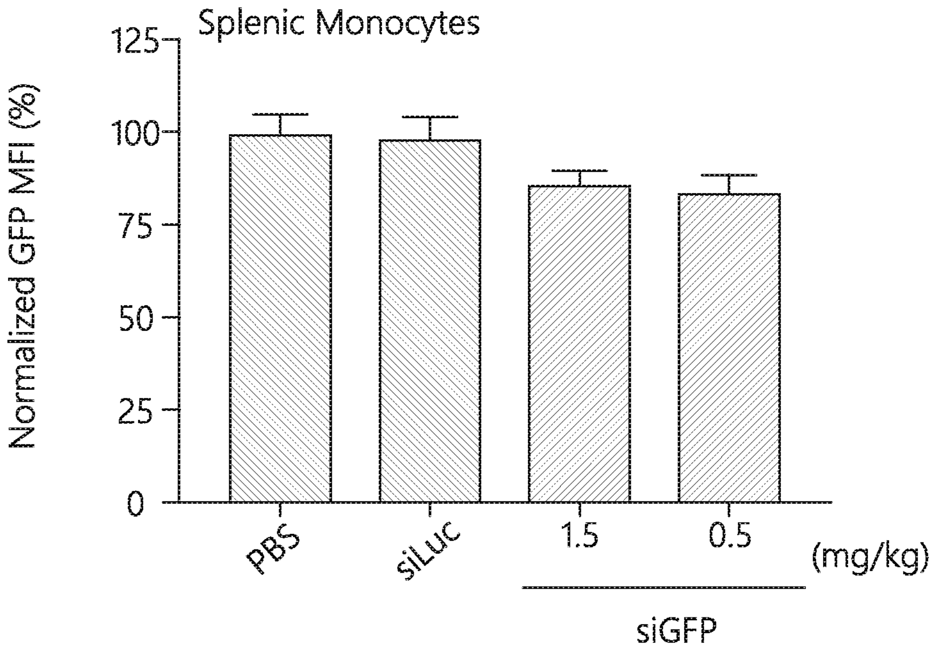
Figures 5F, 5G:
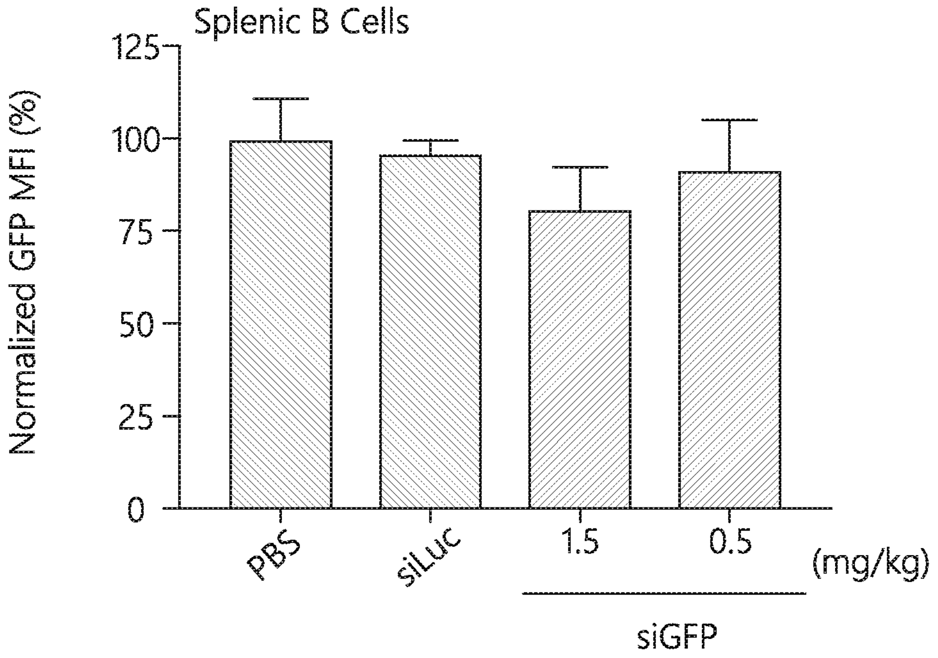
FIG. 5G is the sequence and chemical modification on sgGFP.

The same enrichment analyses were performed for the 13 ionizable lipids, for both the lipid tail and head group. 3 ionizable lipids were enriched (FIG. 2I). To elucidate if the headgroup of the ionizable lipid impacted enrichment, enrichment of each headgroup versus headgroup molecular weight, hydrophobicity (Log P), and polar surface area were plotted (FIGS. 4A-4C, Table 1). No correlations were observed between these chemical traits and enrichment. The lipid that was most enriched, 11-A, contained a conformationally constrained adamantane tail. The enrichment of 11-A was compared with 11-L and 11-S, two lipids with the same headgroup (11), but different second lipid tails. To determine if the difference in enrichment was due to the structural transformation of the second lipid tail, the normalized DNA delivery of each lipid was analyzed. 11-A resulted in significantly more delivery than 11-L and 11-S (FIG. 2J). A paired analysis was performed using compounds with the same molar ratio. Adamantane containing tails outperformed other tail structure (FIG. 4D). Normalized T cell delivery was plotted against LNP size, and no relationship was found (FIG. 4E). Taken together, these data suggest that for monodisperse LNPs with hydrodynamic diameters between 30 and 170 nm, LNP chemical structure affects delivery more than size.

TABLE 1

Enrichment of LNPs with Various Headgroups

| Lipomer | Molecular Weight of Head Group | LogP of Head Group | Total Polar Surface Area of Head Group | Enrichment in T Cells |
|---|---|---|---|---|
| Gan-1-105 | 158 | 0.62 | 29.5 | −1.3 |
| Gan-1-106 | 156 | 0.26 | 29.5 | 3.9 |
| Gan-1-107 | 185 | −0.3 | 32.8 | 2.6 |
| Gan-1-33 | 158 | 0.62 | 29.5 | −1.3 |
| Gan-2-10 | 72 | −1.36 | 43 | 0 |
| Gan-2-13 | 149 | 0.95 | 57.5 | −1.3 |
| Gan-2-2 | 158 | 0.62 | 29.5 | 5.2 |
| Gan-2-3 | 151 | 0.31 | 32.7 | −1.3 |
| Gan-2-5 | 202 | 0.44 | 64.6 | −1.3 |
| Gan-2-6 | 145 | 0.81 | 41.4 | −3.9 |
| Gan-2-7 | 122 | 0.45 | 67.8 | 0 |
| Gan-2-8 | 107 | −0.47 | 41.4 | 0 |
| Gan-2-9 | 157 | 0.95 | 41.8 | −1.3 |

Example 4. cLNPs Deliver Small RNAs that Change Gene Expression in CD8+ T Cells Materials and Methods:

See materials and methods sections above.

Figure 3A:
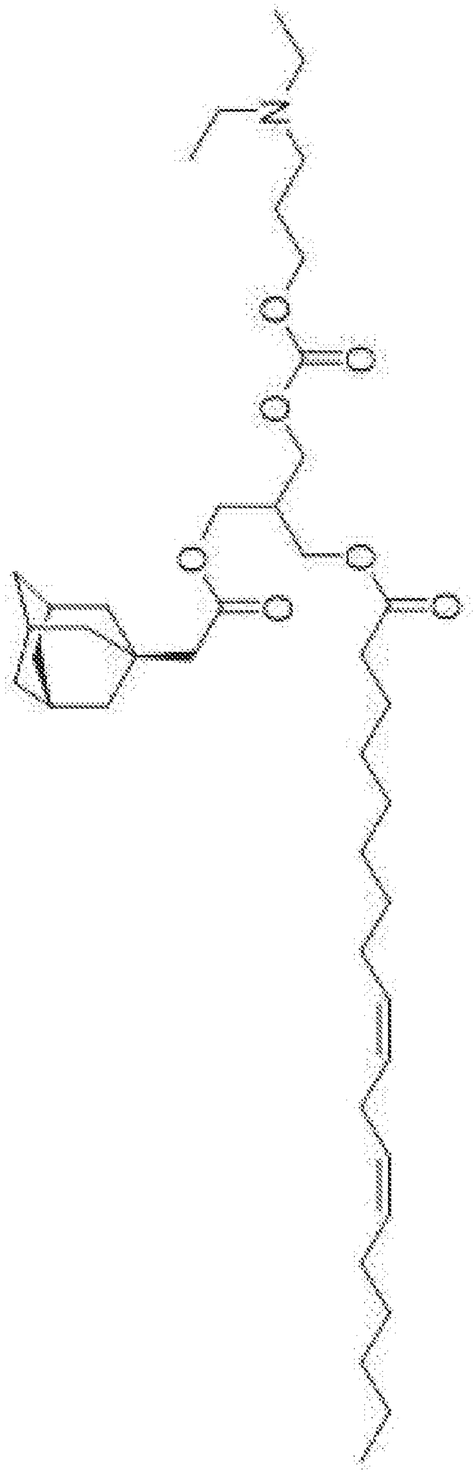
FIG. 3A shows the structure of ionizable lipid 11-A.
Figure 3C:
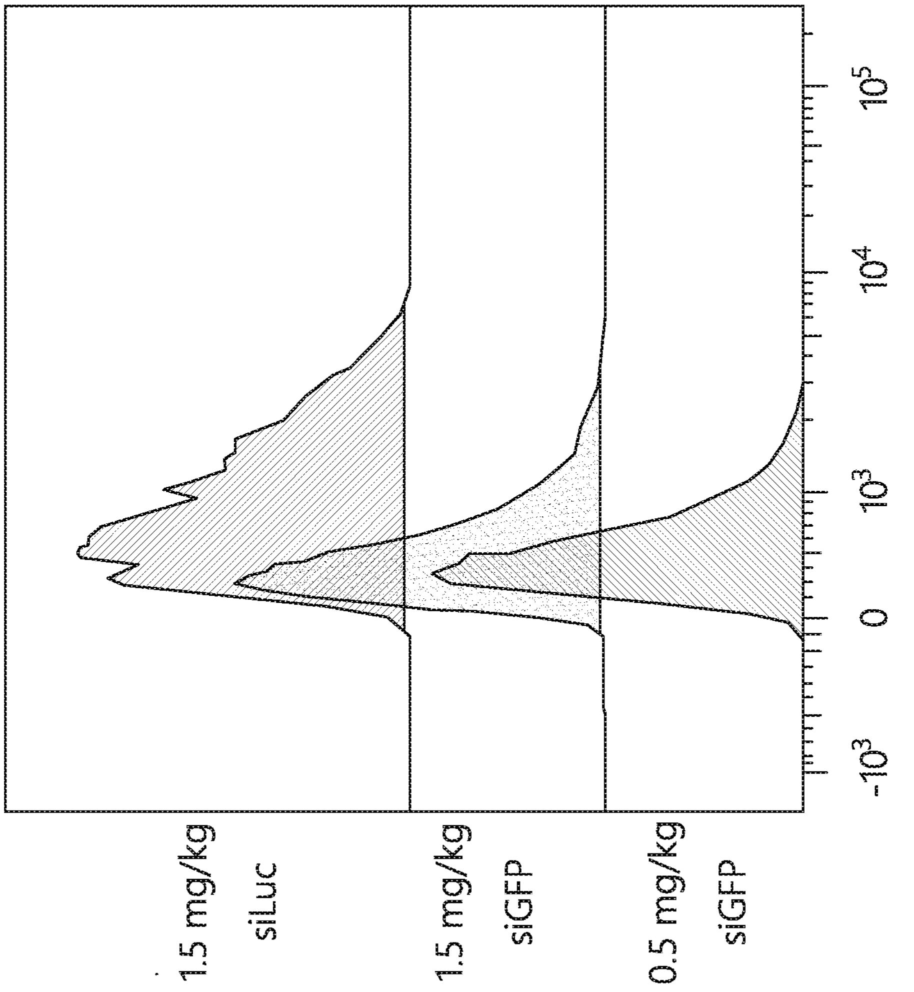
FIG. 3C is a flow cytometry histogram showing GFP expression in splenic $CD3^{+}$ T cells 72 hours after treatment of cLNP carrying siLuc at a dose of 1.5 mg/kg or siGFP at doses of 0.5 mg kg and 1.5 mg/kg.
Figure 3B:
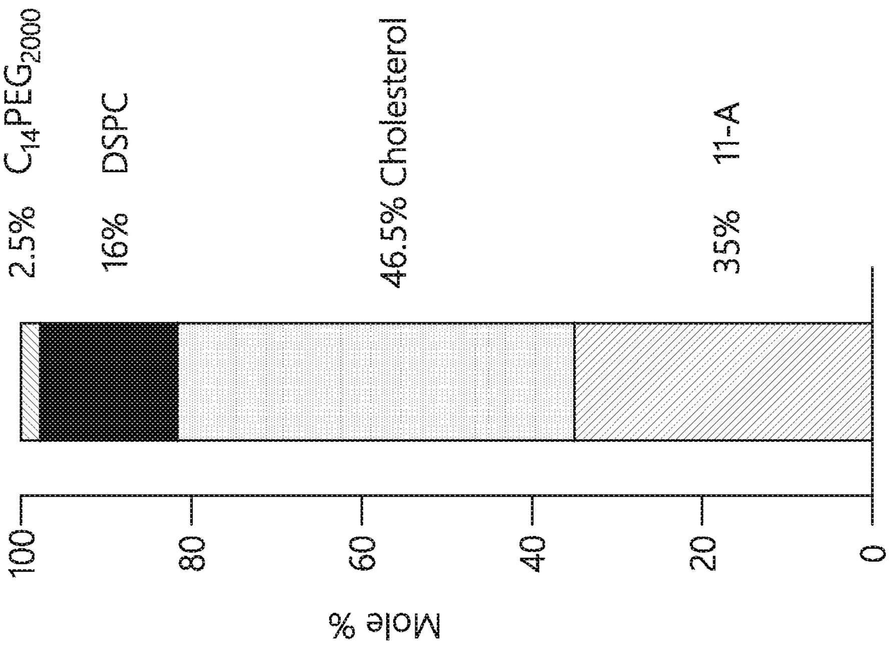
FIG. 3B shows the molar composition of top performing cLNP.
Figure 3D:
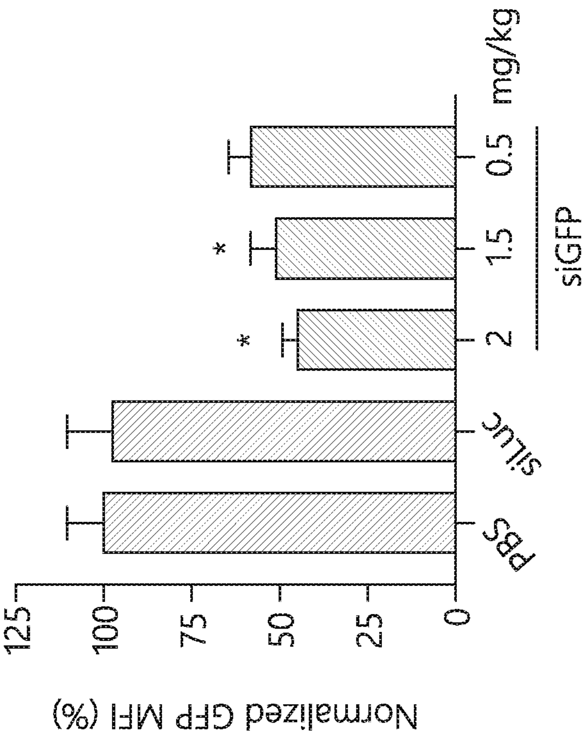
FIG. 3D is a bar graph showing normalized GFP MFI in splenic CD3+ T cells 72 hours after treatment of cLNP carrying either siLuc or siGFP at various doses.
Figure 3E:
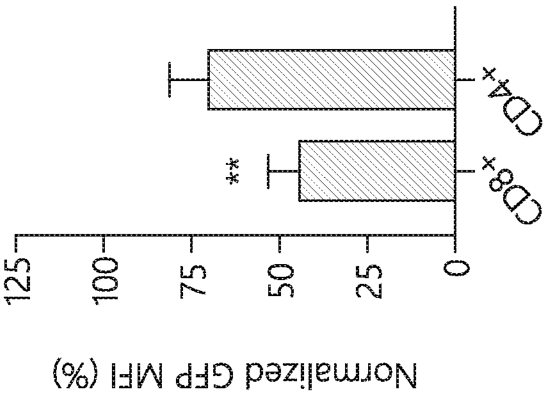
FIG. 3E is a bar graph showing normalized GFP MFI in splenic CD8+ and CD4+ T cells 72 hours after treatment of cLNP carrying siGFP at a dose of 2.0 mg/kg.

Results:

Like all high throughput screening systems, the value of the siGFP/DNA barcode assay is related to its ability to make predictions. Based on the sequencing data, a nanoparticle was selected for further investigation (FIGS. 3A-3B). Based on enrichment analysis, this cLNP contained a constrained lipid as well as DSPC. Over the course of several experiments, the LNP was formulated with a control siRNA targeting Luciferase (siLuc) or siGFP, and intravenously injected into mice at doses between 0.5 mg/kg and 2.0 mg/kg (FIG. 3C,D). Compared to T cells isolated from mice treated with PBS or siLuc, T cells isolated from mice treated with siGFP had reduced GFP expression. Notably, robust protein silencing was observed at doses as low as 0.5 mg/kg (FIG. 3C,D). GFP protein expression was measured in subsets of T cells, namely CD4+ and CD8+, observing more potent protein silencing in CD8+ T cells (FIG. 3E). Additionally, GFP silencing was quantified in 6 off-target cell types in the liver and the spleen. No significant silencing was observed at doses of 0.5 mg/kg and 1.5 mg/kg (FIGS. S4A-F), suggesting that these cLNPs preferentially silence genes in splenic CD8+ T cells.

Figure 3F:
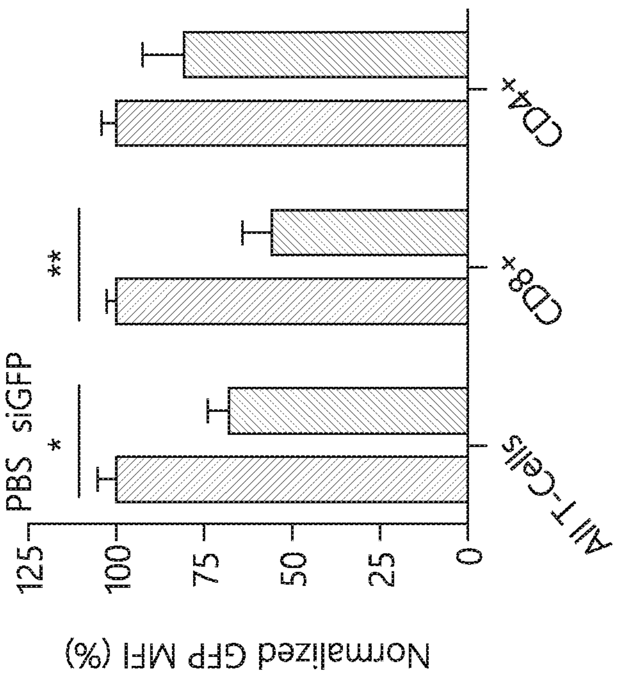
FIG. 3F is a bar graph showing normalized GFP MFI in splenic CD3+ T cells as well as CD8+ and CD4+ T cells after treatment of cLNPs carrying sgRNA at a dose of 2.0 mg/kg.
Figure 3G:
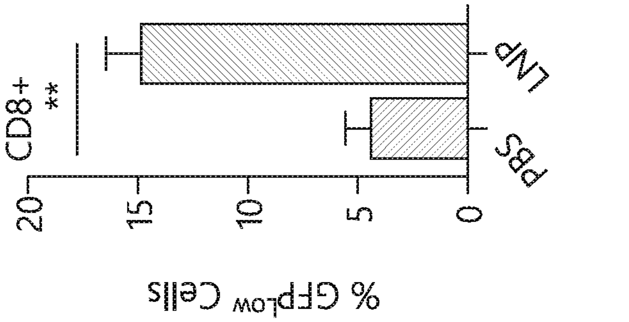
FIG. 3G is a bar graph showing percent $GFP^{Low}$ CD8+ T cells after treatment of cLNPs carrying sgRNA at a dose of 2.0 mg/kg.

To confirm the efficacy of the novel cLNP with a gene editing payload, the lead cLNP carrying sgRNA targeting GFP was injected into mice (Platt, R. J., et al., *Cell,* 159:440-445 (2014)) constitutively expressing Cas9 and GFP at a dose of 2.0 mg/kg. After five days, GFP expression was measured in CD3+ T cells as well as in CD4+ and CD8+ T cells. Similar to the observed CD8+ tropism with siRNA, more potent protein silencing was observed in CD8+ than in CD4+ T cells (FIG. 3F). Additionally, this decrease in GFP expression was coupled with an increase in % $GFP^{Low}$ CD8+ T cells (FIG. 3G). Taken together, these data led to the conclusion that cLNPs without targeting ligands can deliver siRNA to splenic T cells at doses below 1 mg/kg. cLNPs were well tolerated at doses of siRNA and sgRNA in all experiments as indicated by no observed weight loss 24 hrs after administration Nanoparticles targeting non-hepatocytes are notoriously difficult to design (Lorenzer, C., et al., *J Control Release,* 203:1-15 (2015)), in large part because there is no high throughput method to study nanoparticle siRNA delivery in vivo. This universal problem in nanomedicine slows the development of all RNA therapies, since scientists are forced to perform high throughput nanoparticle assays in vitro, even though cell culture does not recapitulate all the factors (heterogenous vasculature (Augustin, H. G., et al., *Science,* 357 (2017), complex microenvironment (MacParland, S. A., et al., *ACS Nano,* 11:2428-2443 (2017), off-target cells (Tavares, A. J., et al., *PNAS,* 114:E10871-e10880 (2017), differential blood flow rates (Tsoi, K. M. et al., *Nat Mater,* 15:1212-1221 (2016)) that affect delivery in vivo. Notably, the results from the screen predicted that preferential T cell delivery would occur; these data were confirmed with a LNP selected from the library. These data provide compelling evidence that high throughput in vivo siRNA screens can rapidly identify nanoparticles with novel tropism.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The subject matter described herein may be embodied in other specific forms without departing from the spirit or essential attributes thereof and, accordingly, reference should be made to the appended claims, rather than to the foregoing specification, as indicating the scope of the subject matter described herein.

We claim:

1. A lipid nanoparticle composition comprising:

an ionizable lipid having a structure according to

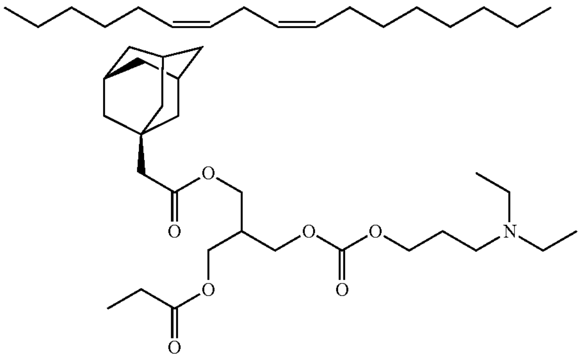

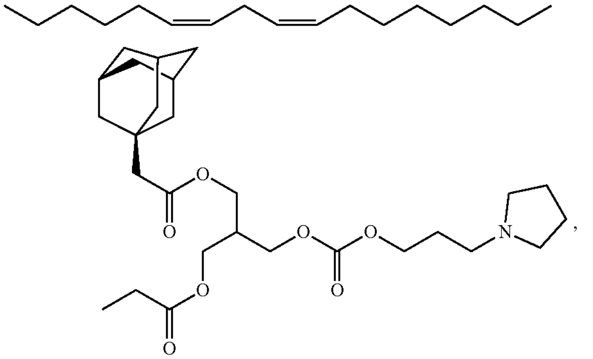

or a pharmaceutically acceptable salt thereof;

a phospholipid;

a polyethylene glycol-lipid;

a cholesterol; and optionally a nucleic acid.

2. The lipid nanoparticle composition of claim 1, wherein the amount of ionizable lipid present is in the range of about 35 to about 65 mole percent, based on total moles.

3. The lipid nanoparticle composition of claim 1, wherein the phospholipid is 1-2-distearoyl-sn-glycero-3-phosphocholine (DSPC).

4. The lipid nanoparticle composition of claim 1, wherein the polyethylene glycol-lipid is $C_{14}PEG_{2000}$ or $C_{18}PEG_{2000}$.

5. The lipid nanoparticle composition of claim 1, wherein the composition comprises about 30 mol % to about 70 mol % ionizable lipid, about 5 mol % to about 25 mol % phospholipid, about 25 mol % to about 45 mol % cholesterol, and about 0.1 mol % to about 5 mol % polyethylene glycol-lipid.

6. The lipid nanoparticle composition of claim 1, wherein the nucleic acid comprises RNA, DNA, single-stranded RNA, single-stranded DNA, double-stranded RNA, double stranded DNA, triple-stranded DNA, siRNA, shRNA, sgRNA, mRNA, miRNA, antisense DNA, or a combination thereof.

7. The lipid nanoparticle composition of claim 1, wherein the nucleic acid encodes a protein.

8. The lipid nanoparticle composition of claim 1, wherein the nucleic acid encodes an RNA-guided DNA endonuclease.

9. The lipid nanoparticle composition of claim 8, wherein the RNA-guided DNA endonuclease is Cas9, CasX, CasY, Cas13, or Cpf1.

10. The nanoparticle composition of claim 1, wherein the lipid nanoparticle has a hydrodynamic diameter in the range of from about 30 nm to about 170 nm.

11. A lipid nanoparticle composition comprising:

an ionizable lipid having a structure according to

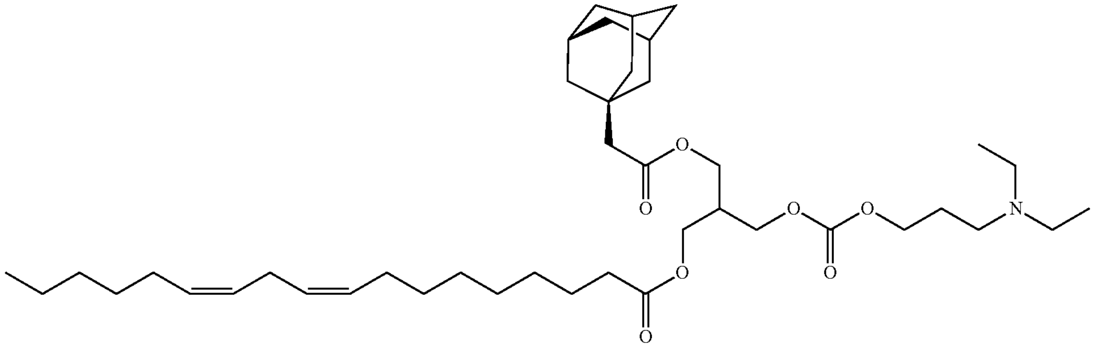

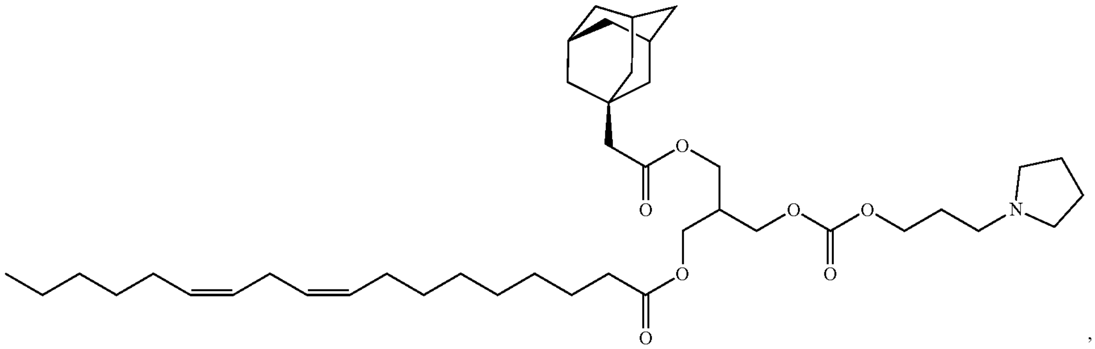

or a pharmaceutically acceptable salt thereof;

1-2-distearoyl-sn-glycero-3-phosphocholine (DSPC);

$C_{14}PEG_{2000}$;

cholesterol; and siRNA.

12. The lipid nanoparticle of claim 11, wherein the ionizable lipid is 3-[(1-Adamantanyl)acetoxy]-2-{[3-(diethylamino)propoxycarbonyloxy]methyl}propyl (9Z,12Z)-9,12-octadecadienoate, or a pharmaceutically acceptable salt thereof.

13. The lipid nanoparticle of claim 11, wherein $C_{14}PEG_{2000}$ is present at about 2.0 to about 3.0 mole percent, DSPC is present at about 15 to about 17 mole percent, cholesterol is present at about 45 to about 47 mole percent, the ionizable lipid is present at about 33 to about 36 mole percent, and the siRNA is present at 5 to 20 mass ratio of total lipid to siRNA.

14. The lipid nanoparticle of claim 11, wherein $C_{14}PEG_{2000}$ is present at about 2.5 mole percent, DSPC is present at about 16 mole percent, cholesterol is present at about 46.5 mole percent, and the ionizable lipid is present at about 35 mole percent.

3-[(1-Adamantanyl)acetoxy]-2-{[3-(diethylamino)propoxycarbonyloxy]methyl}propyl (9Z,12Z)-9,12-octadecadienoate, or a pharmaceutically acceptable salt thereof;

DSPC;

a polyethylene glycol-lipid;

a cholesterol; and a nucleic acid, wherein the lipid nanoparticle composition delivers the nucleic acid to the immune cell in the subject.

19. The method of claim 18, wherein the lipid nanoparticle composition does not contain a targeting ligand that targets the lipid nanoparticle composition to the immune cell.

20. The method of claim 18, wherein the immune cell is a T cell.

21. A method for increasing delivery of a nanoparticle composition to non-hepatocyte cells in a subject comprising formulating the nanoparticle composition to comprise an amount of an ionizable lipid that is effective to increase delivery of the nanoparticle composition to non-hepatocyte cells when administered to the subject, wherein the ionizable lipid has a structure according to either

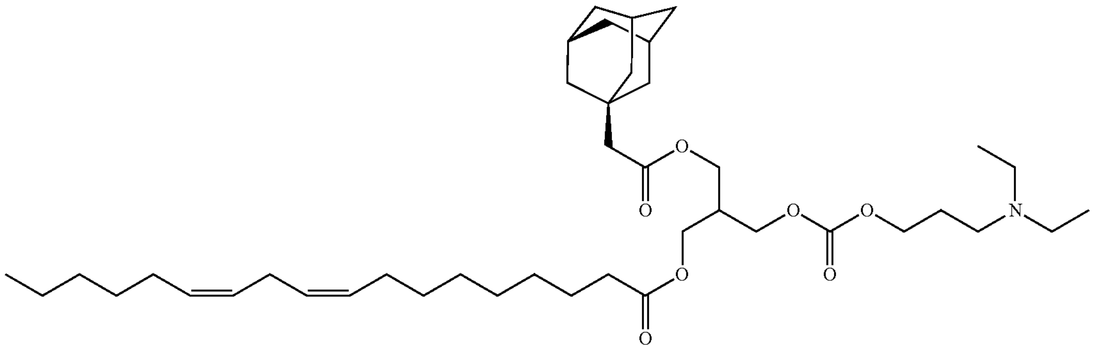

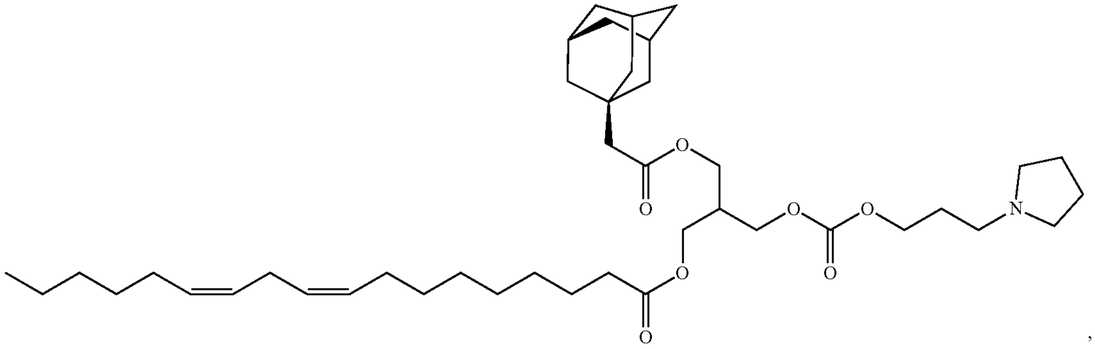

, or a pharmaceutically acceptable salt thereof.

15. A pharmaceutical composition comprising the lipid nanoparticle composition of claim 1, and a pharmaceutically acceptable excipient.

16. A method of delivering a nucleic acid to a subject in need thereof, comprising, administering to the subject the lipid nanoparticle composition of claim 1.

17. The method of claim 16, further comprising administering a second therapeutic agent to the subject.

18. A method of delivering a nucleic acid to an immune cell in a subject in need thereof, comprising:

administering to the subject a lipid nanoparticle composition consisting of

22. A method for reducing gene expression in an immune cell in a subject in need thereof, comprising:

administering to the subject a lipid nanoparticle composition consisting of

3-[(1-Adamantanyl)acetoxy]-2-{[3-(diethylamino)propoxycarbonyloxy]methyl}propyl (9Z,12Z)-9,12-octadecadienoate, or a pharmaceutically acceptable salt thereof;

DSPC;

a polyethylene glycol-lipid;

cholesterol; and an inhibitory nucleic acid, wherein the lipid nanoparticle composition delivers the inhibitory nucleic acid to the immune cell in the subject.

23. A method for editing a gene in an immune cell in a subject in need thereof, comprising:

administering to the subject a lipid nanoparticle composition comprising a first and second population of lipid nanoparticles, wherein the first population of lipid nanoparticles consists of 3-[(1-Adamantanyl)acetoxy]-2-{[3-(diethylamino) propoxycarbonyloxy]methyl}propyl (9Z,12Z)-9,12-octadecadienoate, or a pharmaceutically acceptable salt thereof, DSPC, a polyethylene glycol-lipid, cholesterol, and sgRNA specific for the gene, and wherein the second population of lipid nanoparticles consists of 3-[(1-Adamantanyl)acetoxy]-2-{[3-(diethylamino)propoxycarbonyloxy]methyl}propyl (9Z,12Z)-9,12-octadecadienoate, or a pharmaceutically acceptable salt thereof, DSPC, a polyethylene glycol-lipid, cholesterol, and mRNA encoding an RNA guided DNA endonuclease.

24. A compound having a structure that is

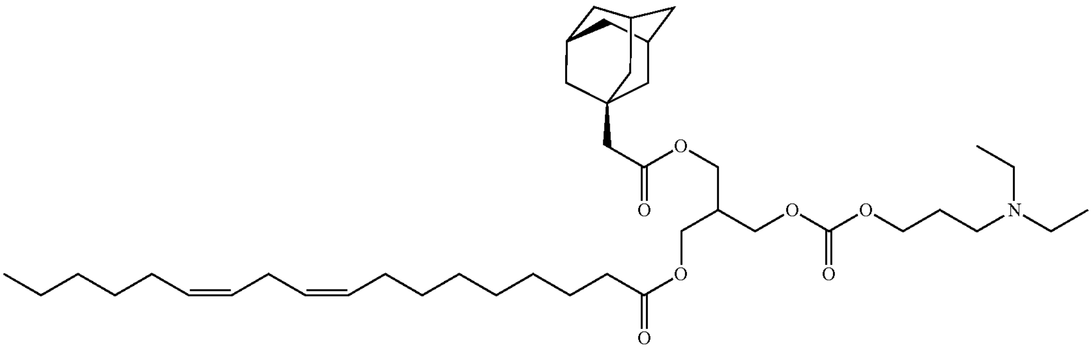

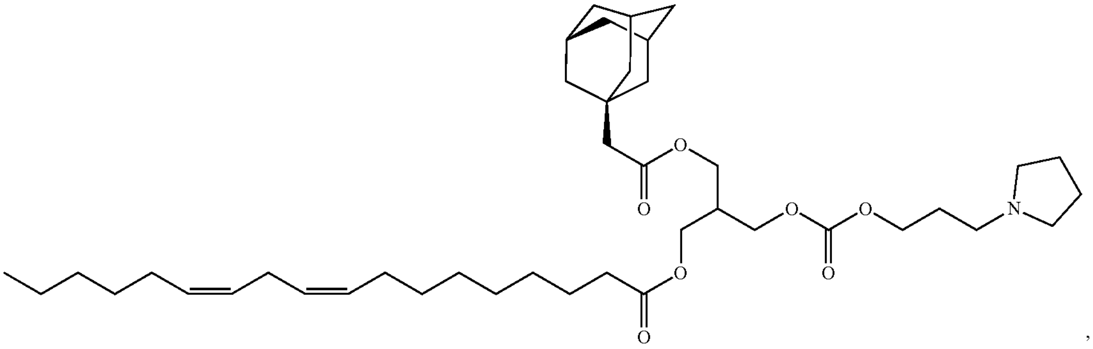

, or a pharmaceutically acceptable salt thereof.

25. The compound of claim 24, having a structure that is

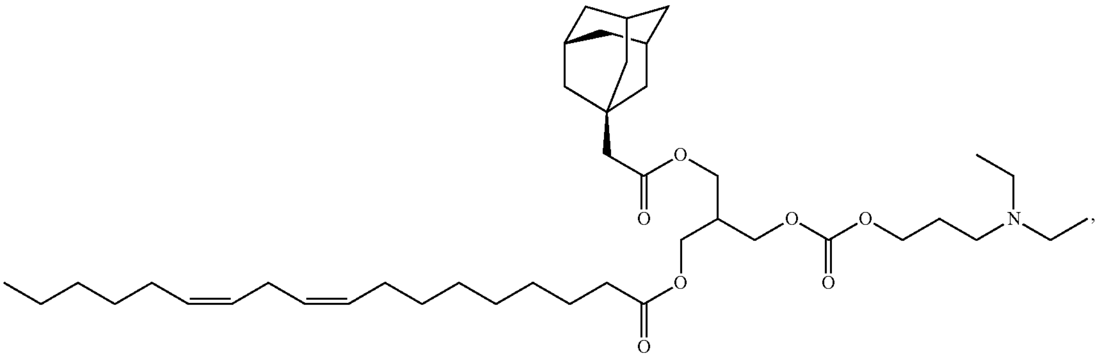 [SMILES: CCCCC/C=C\C/C=C\CCCCCCCC(=O)OCC(COC(=O)C[C@]12CC3CC(C[C@@H](C3)C1)C2)COC(=O)OCCCN(CC)CC]

, or a pharmaceutically acceptable salt thereof.

26. The compound of claim 24, having a structure that is
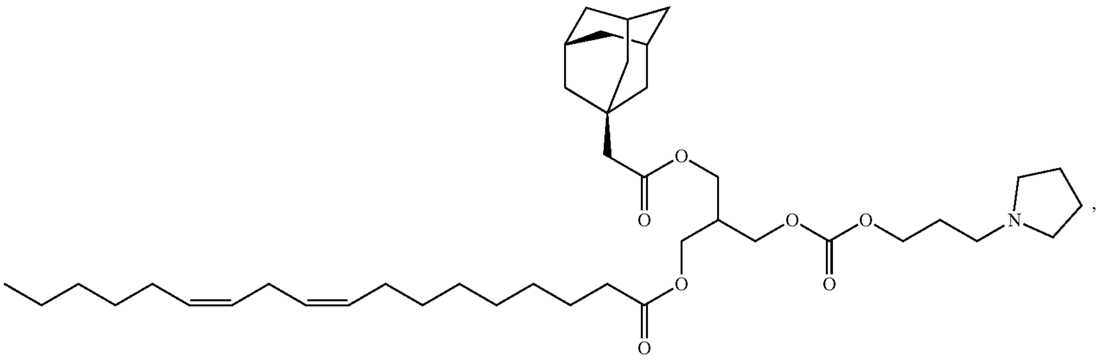 [SMILES: CCCCC/C=C\C/C=C\CCCCCCCC(=O)OCC(COC(=O)C[C@]12CC3CC(C[C@@H](C3)C1)C2)COC(=O)OCCCN1CCCC1]
,
or a pharmaceutically acceptable salt thereof.
* * * * *

SEQUENCE LISTING

```
<160> NUMBER OF SEQ ID NOS: 1

<210> SEQ ID NO 1
<211> LENGTH: 101
<212> TYPE: RNA
<213> ORGANISM: artificial sequence
<220> FEATURE:
```

<223> OTHER INFORMATION: synthetic; sgGFP
<220> FEATURE:
<221> NAME/KEY: misc_feature
<222> LOCATION: (1)..(1)
<223> OTHER INFORMATION: 2'-O-methyl guanosine with phosphorothioate
<220> FEATURE:
<221> NAME/KEY: misc_feature
<222> LOCATION: (2)..(2)
<223> OTHER INFORMATION: 2'-O-methyl guanosine with phosphorothioate
<220> FEATURE:
<221> NAME/KEY: misc_feature
<222> LOCATION: (3)..(3)
<223> OTHER INFORMATION: 2'-O-methyl guanosine with phosphorothioate
<220> FEATURE:
<221> NAME/KEY: misc_feature
<222> LOCATION: (6)..(6)
<223> OTHER INFORMATION: adenosine with phosphorothioate
<220> FEATURE:
<221> NAME/KEY: misc_feature
<222> LOCATION: (7)..(7)
<223> OTHER INFORMATION: guanosine with phosphorothioate
<220> FEATURE:
<221> NAME/KEY: misc_feature
<222> LOCATION: (8)..(8)
<223> OTHER INFORMATION: 2'-fluoro guanosine with phosphorothioate
<220> FEATURE:
<221> NAME/KEY: misc_feature
<222> LOCATION: (9)..(9)
<223> OTHER INFORMATION: 2'-fluoro adenosine with phosphorothioate
<220> FEATURE:
<221> NAME/KEY: misc_feature
<222> LOCATION: (10)..(10)
<223> OTHER INFORMATION: 2'-fluoro guanosine with phosphorothioate
<220> FEATURE:
<221> NAME/KEY: misc_feature
<222> LOCATION: (11)..(11)
<223> OTHER INFORMATION: 2'-fluoro cytidine
<220> FEATURE:
<221> NAME/KEY: misc_feature
<222> LOCATION: (13)..(13)
<223> OTHER INFORMATION: 2'-fluoro guanosine
<220> FEATURE:
<221> NAME/KEY: misc_feature
<222> LOCATION: (14)..(14)
<223> OTHER INFORMATION: 2'-fluoro uridine
<220> FEATURE:
<221> NAME/KEY: misc_feature
<222> LOCATION: (17)..(17)
<223> OTHER INFORMATION: 2'-fluoro adenosine
<220> FEATURE:
<221> NAME/KEY: misc_feature
<222> LOCATION: (18)..(18)
<223> OTHER INFORMATION: 2'-fluoro cytidine
<220> FEATURE:
<221> NAME/KEY: misc_feature
<222> LOCATION: (21)..(21)
<223> OTHER INFORMATION: 2'-O-methyl guanosine
<220> FEATURE:
<221> NAME/KEY: misc_feature
<222> LOCATION: (28)..(28)
<223> OTHER INFORMATION: 2'-O-methyl adenosine
<220> FEATURE:
<221> NAME/KEY: misc_feature
<222> LOCATION: (29)..(29)
<223> OTHER INFORMATION: 2'-O-methyl guanosine
<220> FEATURE:
<221> NAME/KEY: misc_feature
<222> LOCATION: (30)..(30)
<223> OTHER INFORMATION: 2'-O-methyl cytidine
<220> FEATURE:
<221> NAME/KEY: misc_feature
<222> LOCATION: (31)..(31)
<223> OTHER INFORMATION: 2'-O-methyl uridine
<220> FEATURE:
<221> NAME/KEY: misc_feature
<222> LOCATION: (32)..(32)
<223> OTHER INFORMATION: 2'-O-methyl adenosine
<220> FEATURE:
<221> NAME/KEY: misc_feature
<222> LOCATION: (33)..(33)
<223> OTHER INFORMATION: 2'-O-methyl guanosine
<220> FEATURE:
<221> NAME/KEY: misc_feature
<222> LOCATION: (34)..(34)
<223> OTHER INFORMATION: 2'-O-methyl adenosine
<220> FEATURE:
<221> NAME/KEY: misc_feature
<222> LOCATION: (35)..(35)
<223> OTHER INFORMATION: 2'-O-methyl adenosine
<220> FEATURE:
<221> NAME/KEY: misc_feature
<222> LOCATION: (36)..(36)
<223> OTHER INFORMATION: 2'-O-methyl adenosine
<220> FEATURE:
<221> NAME/KEY: misc_feature
<222> LOCATION: (37)..(37)
<223> OTHER INFORMATION: 2'-O-methyl uridine
<220> FEATURE:
<221> NAME/KEY: misc_feature
<222> LOCATION: (38)..(38)
<223> OTHER INFORMATION: 2'-O-methyl adenosine
<220> FEATURE:
<221> NAME/KEY: misc_feature
<222> LOCATION: (39)..(39)
<223> OTHER INFORMATION: 2'-O-methyl guanosine
<220> FEATURE:
<221> NAME/KEY: misc_feature
<222> LOCATION: (40)..(40)
<223> OTHER INFORMATION: 2'-O-methyl cytidine
<220> FEATURE:
<221> NAME/KEY: misc_feature
<222> LOCATION: (41)..(41)
<223> OTHER INFORMATION: 2'-O-methyl adenosine
<220> FEATURE:
<221> NAME/KEY: misc_feature
<222> LOCATION: (42)..(42)
<223> OTHER INFORMATION: 2'-O-methyl adenosine
<220> FEATURE:
<221> NAME/KEY: misc_feature
<222> LOCATION: (46)..(46)
<223> OTHER INFORMATION: 2'-O-methyl adenosine
<220> FEATURE:
<221> NAME/KEY: misc_feature
<222> LOCATION: (48)..(48)
<223> OTHER INFORMATION: 2'-O-methyl adenosine
<220> FEATURE:
<221> NAME/KEY: misc_feature
<222> LOCATION: (50)..(50)
<223> OTHER INFORMATION: 2'-O-methyl uridine
<220> FEATURE:
<221> NAME/KEY: misc_feature
<222> LOCATION: (52)..(52)
<223> OTHER INFORMATION: 2'-O-methyl adenosine
<220> FEATURE:
<221> NAME/KEY: misc_feature
<222> LOCATION: (53)..(53)
<223> OTHER INFORMATION: 2'-O-methyl guanosine
<220> FEATURE:
<221> NAME/KEY: misc_feature
<222> LOCATION: (54)..(54)
<223> OTHER INFORMATION: 2'-O-methyl guanosine
<220> FEATURE:
<221> NAME/KEY: misc_feature
<222> LOCATION: (55)..(55)
<223> OTHER INFORMATION: 2'-O-methyl cytidine
<220> FEATURE:
<221> NAME/KEY: misc_feature
<222> LOCATION: (56)..(56)
<223> OTHER INFORMATION: 2'-O-methyl uridine
<220> FEATURE:
<221> NAME/KEY: misc_feature
<222> LOCATION: (57)..(57)
<223> OTHER INFORMATION: 2'-O-methyl adenosine
<220> FEATURE:
<221> NAME/KEY: misc_feature
<222> LOCATION: (60)..(60)
<223> OTHER INFORMATION: 2'-O-methyl cytidine
<220> FEATURE:

<221> NAME/KEY: misc_feature
<222> LOCATION: (61)..(61)
<223> OTHER INFORMATION: 2'-O-methyl cytidine
<220> FEATURE:
<221> NAME/KEY: misc_feature
<222> LOCATION: (66)..(66)
<223> OTHER INFORMATION: 2'-O-methyl uridine
<220> FEATURE:
<221> NAME/KEY: misc_feature
<222> LOCATION: (67)..(67)
<223> OTHER INFORMATION: 2'-O-methyl cytidine
<220> FEATURE:
<221> NAME/KEY: misc_feature
<222> LOCATION: (70)..(70)
<223> OTHER INFORMATION: 2'-O-methyl cytidine with phosphorothioate
<220> FEATURE:
<221> NAME/KEY: misc_feature
<222> LOCATION: (71)..(71)
<223> OTHER INFORMATION: 2'-O-methyl uridine with phosphorothioate
<220> FEATURE:
<221> NAME/KEY: misc_feature
<222> LOCATION: (72)..(72)
<223> OTHER INFORMATION: 2'-O-methyl uridine with phosphorothioate
<220> FEATURE:
<221> NAME/KEY: misc_feature
<222> LOCATION: (73)..(73)
<223> OTHER INFORMATION: 2'-O-methyl guanosine with phosphorothioate
<220> FEATURE:
<221> NAME/KEY: misc_feature
<222> LOCATION: (74)..(74)
<223> OTHER INFORMATION: 2'-O-methyl adenosine with phosphorothioate
<220> FEATURE:
<221> NAME/KEY: misc_feature
<222> LOCATION: (75)..(75)
<223> OTHER INFORMATION: 2'-O-methyl adenosine with phosphorothioate
<220> FEATURE:
<221> NAME/KEY: misc_feature
<222> LOCATION: (76)..(76)
<223> OTHER INFORMATION: 2'-O-methyl adenosine with phosphorothioate
<220> FEATURE:
<221> NAME/KEY: misc_feature
<222> LOCATION: (77)..(77)
<223> OTHER INFORMATION: 2'-O-methyl adenosine with phosphorothioate
<220> FEATURE:
<221> NAME/KEY: misc_feature
<222> LOCATION: (78)..(78)
<223> OTHER INFORMATION: 2'-O-methyl adenosine with phosphorothioate
<220> FEATURE:
<221> NAME/KEY: misc_feature
<222> LOCATION: (79)..(79)
<223> OTHER INFORMATION: 2'-O-methyl guanosine
<220> FEATURE:
<221> NAME/KEY: misc_feature
<222> LOCATION: (80)..(80)
<223> OTHER INFORMATION: 2'-O-methyl uridine
<220> FEATURE:
<221> NAME/KEY: misc_feature
<222> LOCATION: (81)..(81)
<223> OTHER INFORMATION: 2'-O-methyl guanosine
<220> FEATURE:
<221> NAME/KEY: misc_feature
<222> LOCATION: (82)..(82)
<223> OTHER INFORMATION: guanosine with phosphorothioate
<220> FEATURE:
<221> NAME/KEY: misc_feature
<222> LOCATION: (83)..(83)
<223> OTHER INFORMATION: 2'-O-methyl cytidine
<220> FEATURE:
<221> NAME/KEY: misc_feature
<222> LOCATION: (84)..(84)
<223> OTHER INFORMATION: 2'-O-methyl adenosine with phosphorothioate
<220> FEATURE:
<221> NAME/KEY: misc_feature
<222> LOCATION: (85)..(85)
<223> OTHER INFORMATION: 2'-O-methyl cytidine with phosphorothioate
<220> FEATURE:
<221> NAME/KEY: misc_feature
<222> LOCATION: (86)..(86)
<223> OTHER INFORMATION: 2'-O-methyl cytidine with phosphorothioate -continued
<220> FEATURE:
<221> NAME/KEY: misc_feature
<222> LOCATION: (87)..(87)
<223> OTHER INFORMATION: 2'-O-methyl guanosine with phosphorothioate
<220> FEATURE:
<221> NAME/KEY: misc_feature
<222> LOCATION: (88)..(88)
<223> OTHER INFORMATION: 2'-O-methyl adenosine with phosphorothioate
<220> FEATURE:
<221> NAME/KEY: misc_feature
<222> LOCATION: (89)..(89)
<223> OTHER INFORMATION: 2'-O-methyl guanosine with phosphorothioate
<220> FEATURE:
<221> NAME/KEY: misc_feature
<222> LOCATION: (90)..(90)
<223> OTHER INFORMATION: 2'-O-methyl uridine with phosphorothioate
<220> FEATURE:
<221> NAME/KEY: misc_feature
<222> LOCATION: (91)..(91)
<223> OTHER INFORMATION: 2'-O-methyl cytidine
<220> FEATURE:
<221> NAME/KEY: misc_feature
<222> LOCATION: (92)..(92)
<223> OTHER INFORMATION: 2'-O-methyl guanosine with phosphorothioate
<220> FEATURE:
<221> NAME/KEY: misc_feature
<222> LOCATION: (93)..(93)
<223> OTHER INFORMATION: 2'-O-methyl guanosine with phosphorothioate
<220> FEATURE:
<221> NAME/KEY: misc_feature
<222> LOCATION: (94)..(94)
<223> OTHER INFORMATION: 2'-O-methyl uridine with phosphorothioate
<220> FEATURE:
<221> NAME/KEY: misc_feature
<222> LOCATION: (95)..(95)
<223> OTHER INFORMATION: 2'-O-methyl guanosine with phosphorothioate
<220> FEATURE:
<221> NAME/KEY: misc_feature
<222> LOCATION: (96)..(96)
<223> OTHER INFORMATION: 2'-O-methyl cytidine with phosphorothioate
<220> FEATURE:
<221> NAME/KEY: misc_feature
<222> LOCATION: (97)..(97)
<223> OTHER INFORMATION: 2'-O-methyl uridine with phosphorothioate
<220> FEATURE:
<221> NAME/KEY: misc_feature
<222> LOCATION: (98)..(98)
<223> OTHER INFORMATION: 2'-O-methyl uridine with phosphorothioate
<220> FEATURE:
<221> NAME/KEY: misc_feature
<222> LOCATION: (99)..(99)
<223> OTHER INFORMATION: 2'-O-methyl uridine with phosphorothioate
<220> FEATURE:
<221> NAME/KEY: misc_feature
<222> LOCATION: (100)..(100)
<223> OTHER INFORMATION: 2'-O-methyl uridine with phosphorothioate
<220> FEATURE:
<221> NAME/KEY: misc_feature
<222> LOCATION: (101)..(101)
<223> OTHER INFORMATION: 2'-O-methyl uridine

<400> SEQUENCE: 1
nnncgnnnnn nunnucnncg nuuuuagnnn nnnnnnnnnn nnguunanan annnnnngun 60
nguuannaan nnnnnnnnnn nnnnnnnnnn nnnnnnnnnn n 101